US012606862B2

(12) United States Patent
Chun et al.

(10) Patent No.: US 12,606,862 B2
(45) Date of Patent: *Apr. 21, 2026

(54) DETECTION OF TARGET NUCLEIC ACID SEQUENCES BY PTO CLEAVAGE AND EXTENSION ASSAY

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 373 days.

This patent is subject to a terminal disclaimer.

(21) Appl. No.: 17/698,230

(22) Filed: Mar. 18, 2022

(65) Prior Publication Data

US 2022/0213535 A1 Jul. 7, 2022

Related U.S. Application Data

(60) Division of application No. 16/700,229, filed on Dec. 2, 2019, now Pat. No. 11,306,349, which is a
(Continued)

(30) Foreign Application Priority Data

| | | |
|---|---|---|
| Jan. 11, 2011 | (KR) | ........................ 10-2011-0002840 |
| Mar. 16, 2011 | (KR) | ........................ 10-2011-0023465 |
| Jun. 17, 2011 | (WO) | ................ PCT/KR2011/004452 |

(51) Int. Cl.
*C12Q 1/68* (2018.01)
*C12Q 1/6818* (2018.01)
(Continued)

(52) U.S. Cl.
CPC ......... *C12Q 1/6837* (2013.01); *C12Q 1/6818* (2013.01); *C12Q 1/6851* (2013.01);
(Continued)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,487,972 | A | 1/1996 | Gelfand et al. |

(Continued)

FOREIGN PATENT DOCUMENTS

| | | |
|---|---|---|
| EP | 1548635 A1 | 6/2005 |
| EP | 1564306 A2 | 8/2005 |

(Continued)

OTHER PUBLICATIONS

Rickert et al, Refinement of single-nucleotide polymorphism genotyping methods on human genomic DNA: amplifluor allele-specific polymerase chain reaction versus ligation detection reaction-TaqMan, Anal Biochem. Jul. 15, 2004;330(2):288-97. doi: 10.1016/j.ab.2004.03.035.*

(Continued)

*Primary Examiner* — Aaron A Priest
(74) *Attorney, Agent, or Firm* — Gianna Julian Arnold; Saul Ewing LLP

(57) ABSTRACT

The present invention relates to the detection of a target nucleic acid sequence by a PTOCE (PTO Cleavage and Extension) assay. The present invention detects a target nucleic acid sequence in which the PTO (Probing and Tagging Oligonucleotide) hybridized with the target nucleic acid sequence is cleaved to release a fragment and the fragment is hybridized with the CTO (Capturing and Templating Oligonucleotide) to form an extended duplex, followed by detecting the presence of the extended duplex. The extended duplex provides signals (generation, increase, extinguishment or decrease of signals) from labels indicating the presence of the extended duplex and has adjustable (Continued)

A. Hybridization

B. Primer extension & Cleavage of PTO

C. Hybridization of PTO fragment to CTO

D. Extension of PTO fragment

E. Melting analysis $T_m$ value, which are well adoptable for detection of the presence of the target nucleic acid sequence.

4 Claims, 30 Drawing Sheets

Specification includes a Sequence Listing.

Related U.S. Application Data continuation of application No. 15/363,025, filed on Nov. 29, 2016, now Pat. No. 10,519,489, which is a continuation of application No. 15/184,412, filed on Jun. 16, 2016, now Pat. No. 10,280,453, which is a continuation of application No. 14/337,493, filed on Jul. 22, 2014, now Pat. No. 9,540,681, which is a continuation of application No. 13/702,546, filed as application No. PCT/KR2012/000287 on Jan. 11, 2012, now Pat. No. 8,809,239.

(51) Int. Cl.

| | | |
|---|---|---|
| *C12Q 1/6837* | (2018.01) | |
| *C12Q 1/6851* | (2018.01) | |
| *C12Q 1/6853* | (2018.01) | |
| *C12Q 1/6858* | (2018.01) | |
| *C12Q 1/6869* | (2018.01) | |
| *C12Q 1/683* | (2018.01) | |

(52) U.S. Cl.

CPC ......... *C12Q 1/6853* (2013.01); *C12Q 1/6858* (2013.01); *C12Q 1/6869* (2013.01); *C12Q 1/683* (2013.01); *C12Q 2525/161* (2013.01)

(56) References Cited

U.S. PATENT DOCUMENTS

| | | | |
|---|---|---|---|
| 5,538,848 A | 7/1996 | Livak et al. | |
| 5,631,129 A * | 5/1997 | Chu ..................... | C12Q 1/6867 536/25.4 |
| 5,691,142 A | 11/1997 | Dahlberg et al. | |
| 5,994,069 A | 11/1999 | Hall et al. | |
| 6,326,145 B1 | 12/2001 | Whitcombe et al. | |
| 6,893,819 B1 | 5/2005 | Sorge | |
| 7,381,532 B2 | 6/2008 | Sorge | |
| 7,422,850 B2 * | 9/2008 | Marshall .............. | C12Q 1/6832 435/6.12 |
| 8,017,327 B2 * | 9/2011 | Wang ................... | C12Q 1/6827 435/6.12 |
| 2002/0045738 A1 | 4/2002 | Singh et al. | |
| 2003/0152942 A1 * | 8/2003 | Fors ..................... | C12Q 1/6883 435/5 |
| 2003/0152971 A1 * | 8/2003 | Lyamichev .............. | C12N 9/22 435/5 |
| 2003/0186238 A1 * | 10/2003 | Allawi ..................... | C12N 9/22 435/5 |
| 2004/0191823 A1 | 9/2004 | Virgos et al. | |
| 2005/0003355 A1 * | 1/2005 | Lu .......................... | B82Y 15/00 506/17 |
| 2005/0142595 A1 | 6/2005 | Maletta et al. | |
| 2005/0221315 A1 | 10/2005 | Braven et al. | |
| 2006/0110748 A1 * | 5/2006 | Sorge ................... | C12Q 1/6844 435/6.1 |
| 2006/0246469 A1 | 11/2006 | Sorge | |
| 2007/0099211 A1 * | 5/2007 | Aivazachvili ...... | G01N 27/3277 435/5 |
| 2007/0231815 A1 | 10/2007 | Sorge | |
| 2008/0131890 A1 | 6/2008 | Allawi et al. | |
| 2008/0160535 A1 | 7/2008 | Gold et al. | |
| 2008/0187910 A1 | 8/2008 | Nilsen | |
| 2008/0193940 A1 | 8/2008 | Aivazachvili et al. | |
| 2008/0241838 A1 | 10/2008 | Scaboo et al. | |
| 2009/0305237 A1 | 12/2009 | Cantor et al. | |
| 2010/0041049 A1 | 2/2010 | Smith et al. | |
| 2010/0105572 A1 * | 4/2010 | Kris ..................... | C12Q 1/6837 506/10 |
| 2011/0171649 A1 | 7/2011 | Kutyavin | |
| 2011/0281266 A1 | 11/2011 | Sergeev et al. | |
| 2013/0116130 A1 * | 5/2013 | Fu ........................ | C12Q 1/6809 506/4 |
| 2013/0295688 A1 | 11/2013 | Bailey | |

FOREIGN PATENT DOCUMENTS

| | | |
|---|---|---|
| EP | 2256216 A1 | 1/2010 |
| JP | 2003334097 | 11/2003 |
| JP | 2004305219 A | 11/2004 |
| KR | 1020090067334 A | 6/2009 |
| WO | 1998023774 A1 | 6/1998 |
| WO | 2004084125 A1 | 9/2004 |
| WO | 2005010199 A2 | 2/2005 |
| WO | 2005059548 A1 | 6/2005 |
| WO | 2006004949 A1 | 1/2006 |
| WO | 2006005081 A2 | 1/2006 |
| WO | 2008076948 A1 | 6/2008 |
| WO | 2008094902 A2 | 8/2008 |
| WO | 2008102057 A1 | 8/2008 |
| WO | 2009117327 A2 | 10/2009 |
| WO | 2010055134 A1 | 5/2010 |
| WO | 2010128041 A1 | 11/2010 |
| WO | 2011028041 A2 | 3/2011 |
| WO | 2011078441 A1 | 6/2011 |
| WO | 2012096523 A2 | 7/2012 |
| WO | 2012134195 A2 | 10/2012 |
| WO | 2013115442 A1 | 8/2013 |

OTHER PUBLICATIONS

Olivier et al., The Invader assay for SNP genotyping, Mutat Res. Jun. 3, 2005;573(1-2):103-10. doi: 10.1016/j.mrfmmm.2004.08.016.*
Allawi, H., et al.; Quantitation of microRNAs using a modified Invader assay; RNA Society, vol. 10, 2004, pp. 1153-1161.
Hessner et al. Genotyping of Factor V G1691A (Leiden) without the Use of PCR by Invasive Cleavage of Oligonucleotide Probes. Clinical Chemistry. vol. 46, No. 8, pp. 1051-1056.
Lambda Exonuclease from thermofisher.com/order/catalog/product/EN0561 (U.S. Appl. No. 14/114,253).
Lohmann et al. A new enzymatic route for production of long 5'-phosphorylated oligonucleotides using suicide cassettes and rolling circle DNA synthesis. BMC Biotechnology. 2007, vol. 7, No. 49.
Lyamichev, V., et al.; Polymorphism identification and quantitative detection of genomic DNA by invasive cleavage of oligonucleotide probes; 1999 Nature America Inc., Nature Biotechnology, vol. 17, Mar. 1999, pp. 292-296.
Nurmi, et al., A new label technology for the detection of specific polymerase chain reaction products in a closed tube. Nucleic Acids Research, 28, e280, 2000 (U.S. Appl. No. 14/114,253).
Olivier, M.; The Invader® assay of SNP genotyping; Elsevier, Mutation Research, vol. 573, 2005, pp. 103-110.
Roux, P., et al.; Direct Measurement of Multiple mRNAs in Nerve Growth Factor-Induced PC12 Cells Using Electrophoretic Tags to Monitor Biomarkers of Neuronal Differentiation in 96-Well Format; Assay and Drug Development Technologies, vol. 2, No. 6, 2004, pp. 637-646.
Stratagene (Gene Characterization Kits; 1988).
Weiner, M., et al.; Kits and their unique role in molecular biology: a brief retrospective; BioTechniques 44: 701-704, Apr. 2008.
Virus (Wikipedia.com) (U.S. Appl. No. 14/114,253).
How many species of bacteria are there (wisegeek.com) (U.S. Appl. No. 14/114,253).
Fungus (Wikipedia.com) (U.S. Appl. No. 14/114,253).
Plant (Wikipedia.com) (U.S. Appl. No. 14/114,253).
Mammal (Wikipedia.com) (U.S. Appl. No. 14/114,253).
Murinae (Wikipedia.com) (U.S. Appl. No. 14/114,253).

(56)          References Cited

OTHER PUBLICATIONS

Fish (Wikipedia.com) (U.S. Appl. No. 14/114,253).
List of sequenced bacterial genomes (Wikipedia.com) (U.S. Appl. No. 14/114,253).
Yuan, Y., et al.; Establishment of a Modified High Resolution Melting Assay Based on Allele-specific-extension to Determine Single Nucleotide Polymorphism; Journal of Capital Medical University, vol. 31, No. 6, Dec. 2010, pp. 742-747 [Abstract].
International Search Report and Written Opinion, dated Sep. 27, 2012, issued in priority International Application No. PCT/KR2012/000287.

\* cited by examiner

Fig. 1
A. Probing and Tagging Oligonucleotide (PTO)
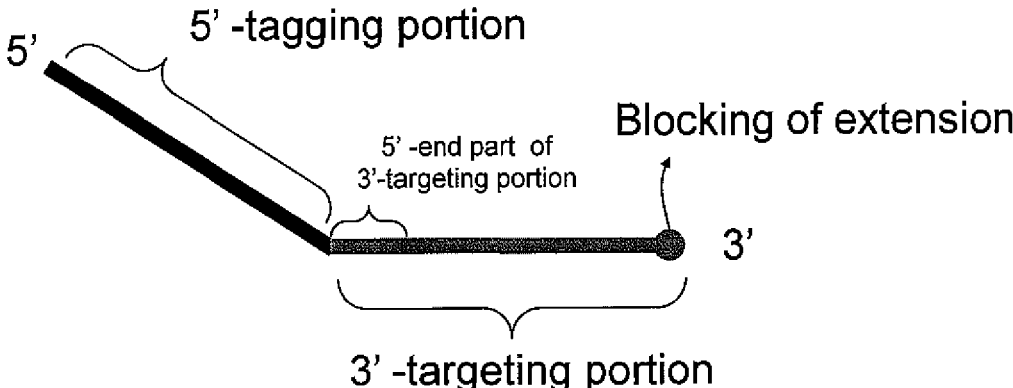
B. Capturing and Templating Oligonucleotide (CTO)
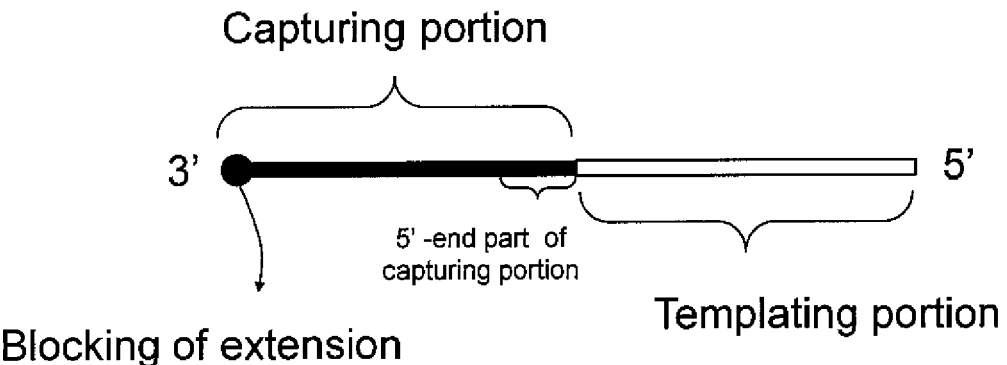

Fig. 2
A. Hybridization
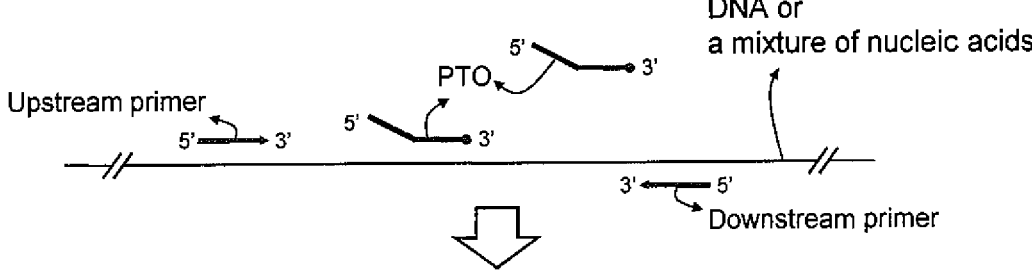
B. Primer extension & Cleavage of PTO
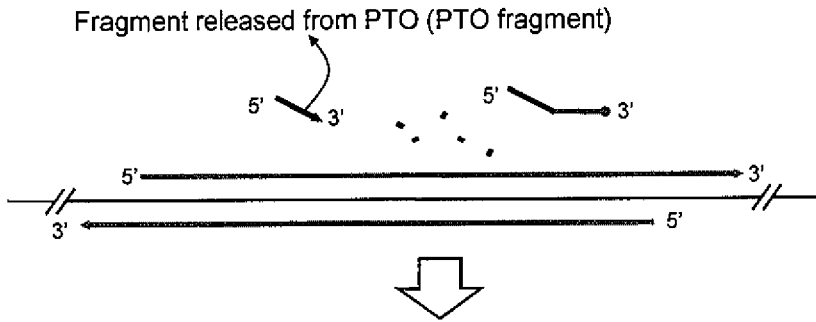
C. Hybridization of PTO fragment to CTO
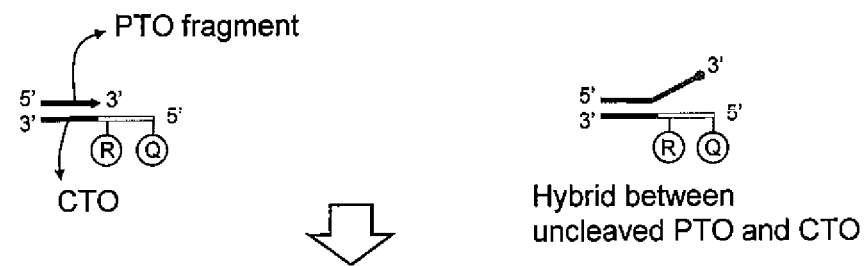
D. Extension of PTO fragment
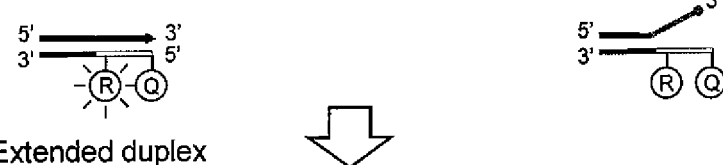
E. Melting analysis

Fig. 3
A. Hybridization
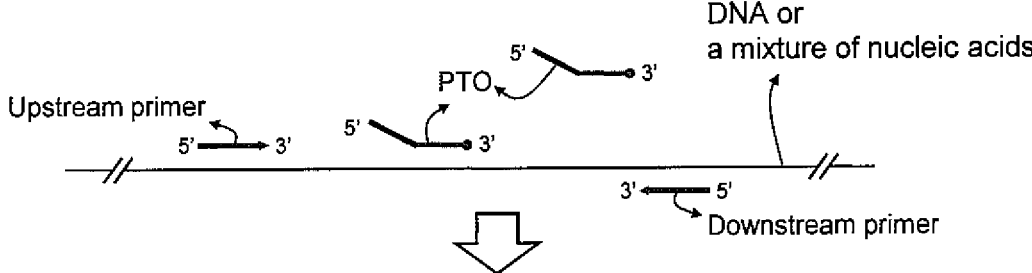
B. Primer extension & Cleavage of PTO
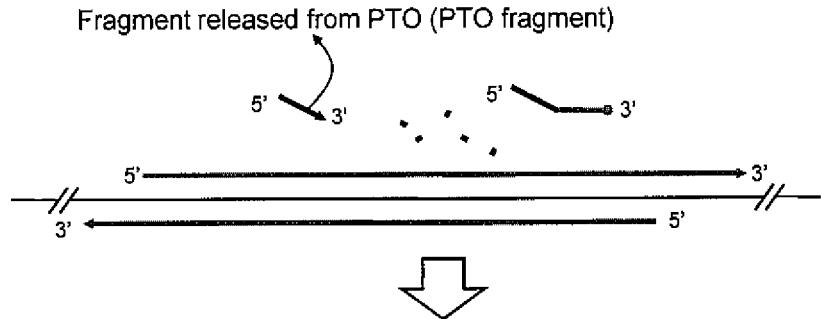
C. Hybridization of PTO fragment to CTO
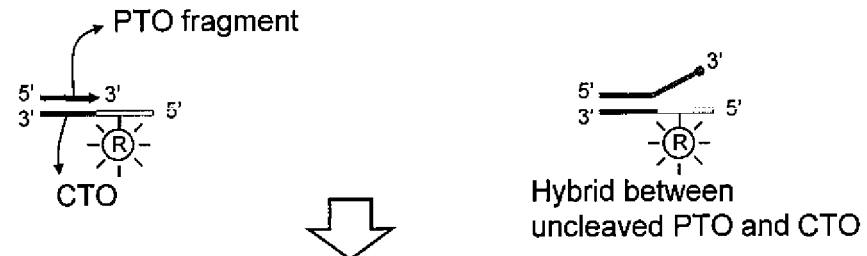
D. Extension of PTO fragment
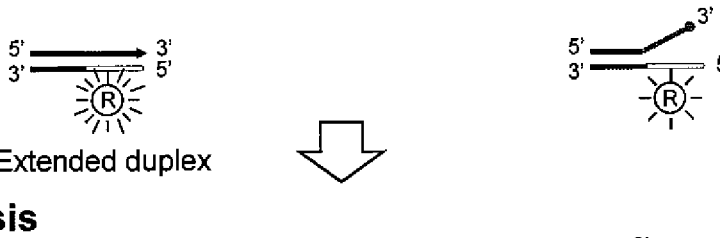
E. Melting analysis

Fig. 4
A. Hybridization
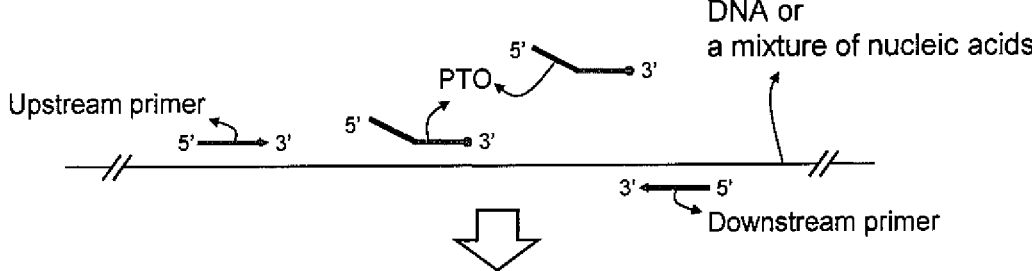
B. Primer extension & Cleavage of PTO
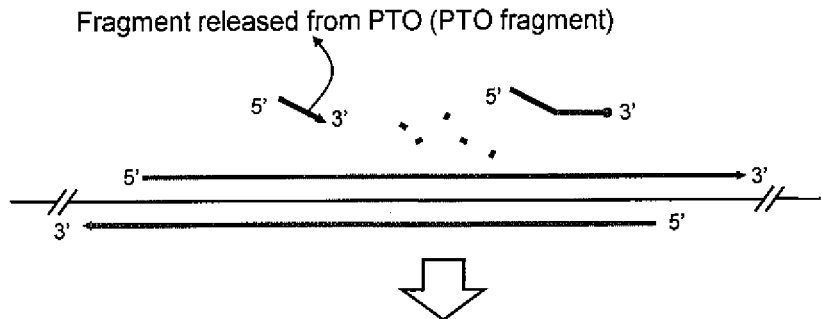
C. Hybridization of PTO fragment to CTO
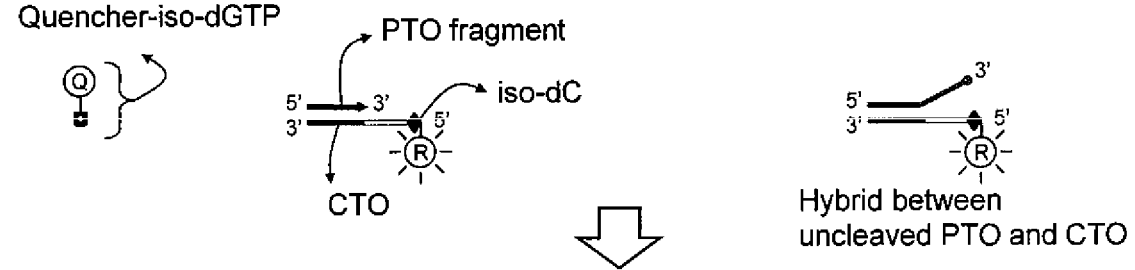
D. Extension of PTO fragment
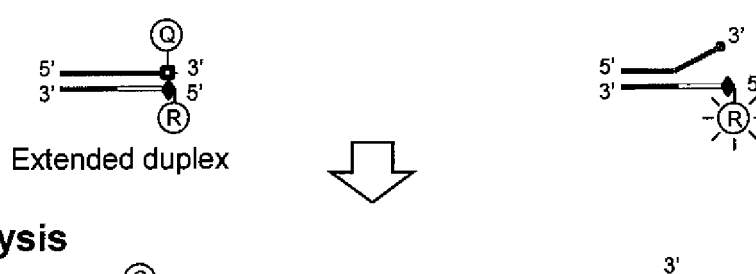
E. Melting analysis

Fig. 5
A. Hybridization
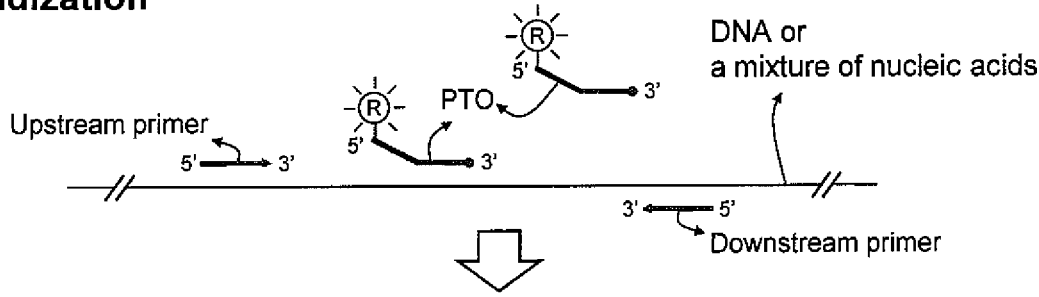
B. Primer extension & Cleavage of PTO
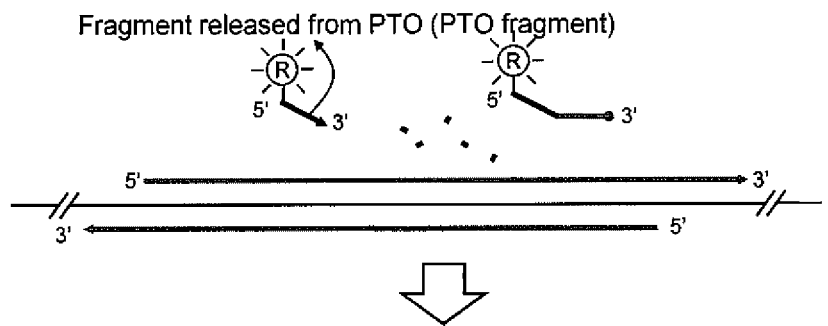
C. Hybridization of PTO fragment to CTO
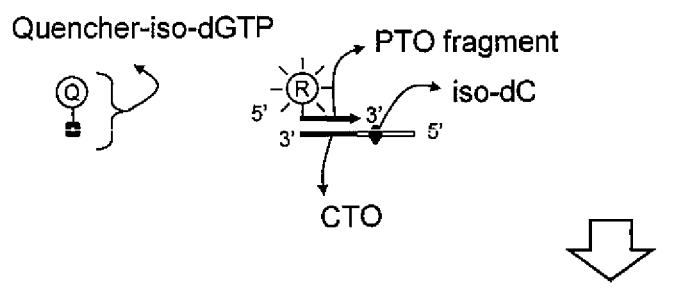
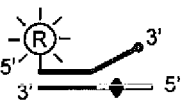
Hybrid between
uncleaved PTO and CTO
D. Extension of PTO fragment
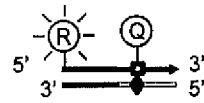
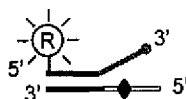
Extended duplex
E. Melting analysis
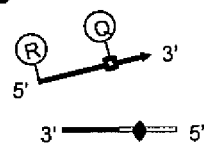
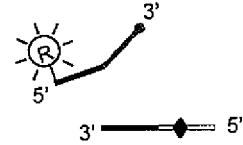

Fig. 6
A. Hybridization
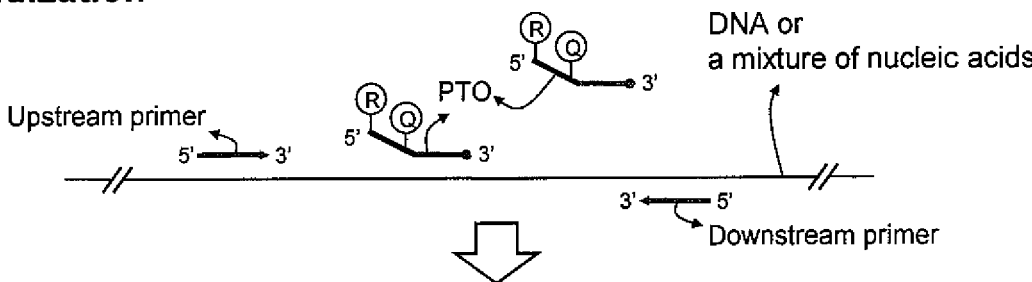
B. Primer extension & Cleavage of PTO
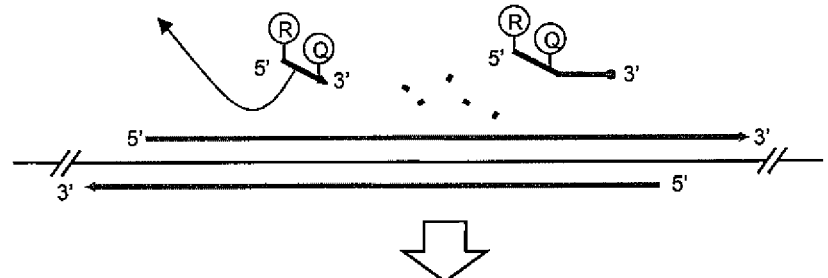
C. Hybridization of PTO fragment to CTO
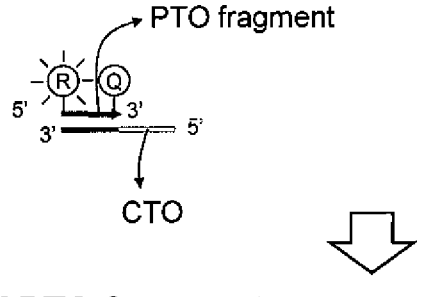
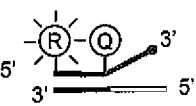
D. Extension of PTO fragment
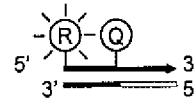
E. Melting analysis
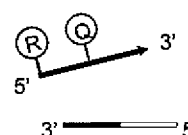
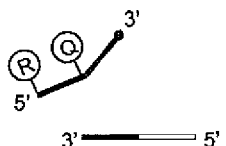

Fig. 7
A. Hybridization
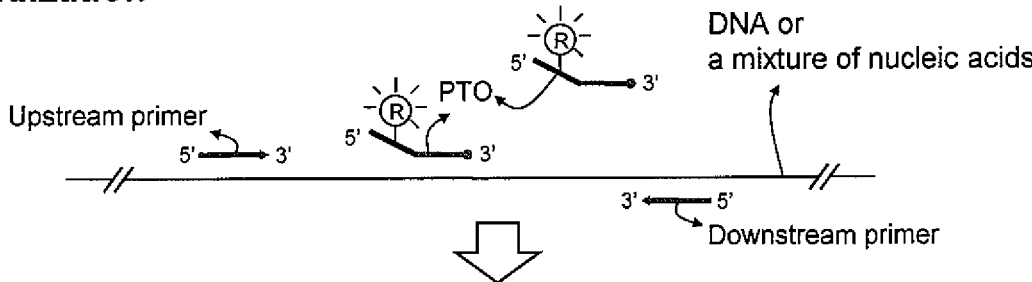
DNA or
a mixture of nucleic acids
PTO
Upstream primer
Downstream primer
B. Primer extension & Cleavage of PTO
Fragment released from PTO (PTO fragment)
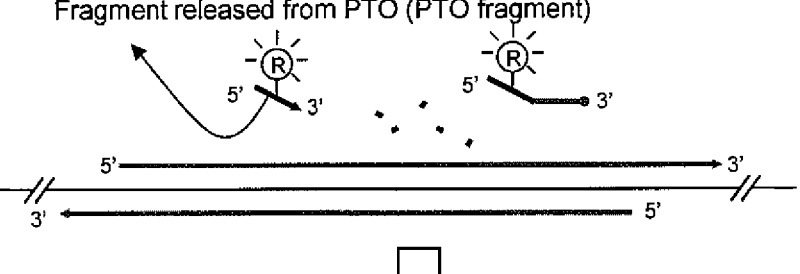
C. Hybridization of PTO fragment to CTO
PTO fragment
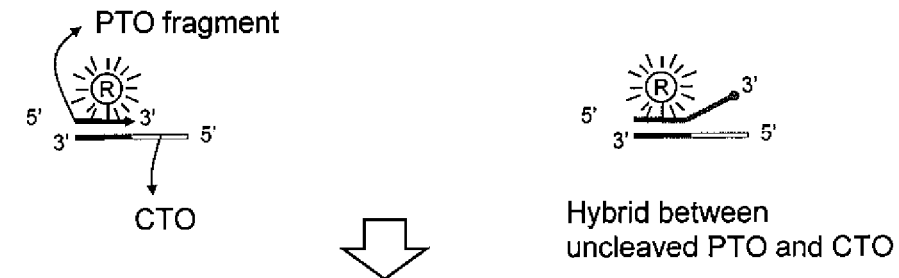
CTO
Hybrid between
uncleaved PTO and CTO
D. Extension of PTO fragment
Extended duplex
E. Melting analysis
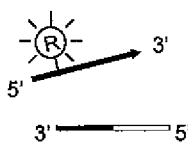
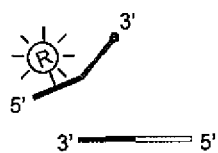

Fig. 8
A. Hybridization
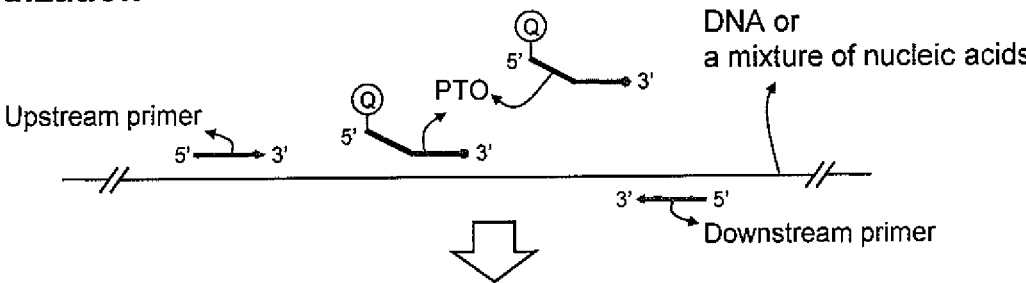
B. Primer extension & Cleavage of PTO
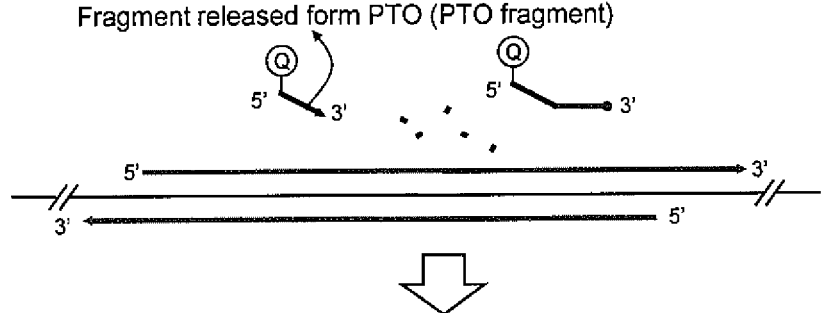
C. Hybridization of PTO fragment to CTO
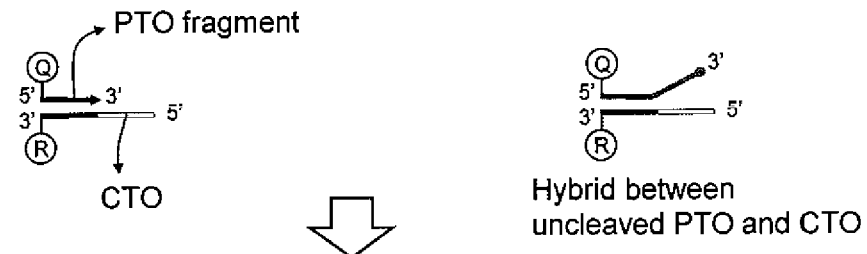
D. Extension of PTO fragment
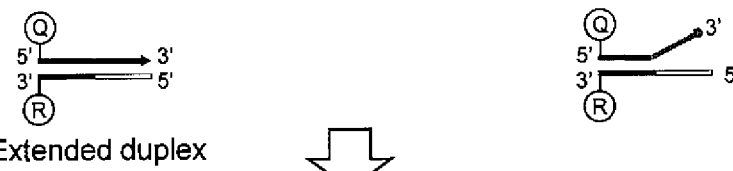
E. Melting analysis

Fig. 9
A. Hybridization
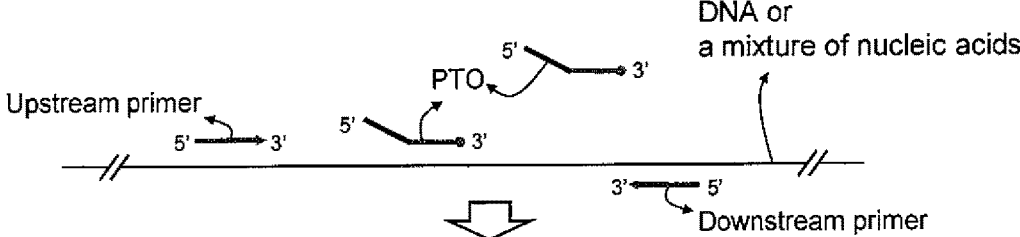
B. Primer extension & Cleavage of PTO
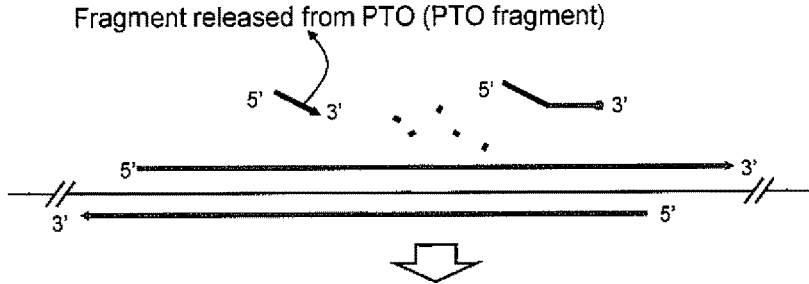
C. Hybridization of PTO fragment to CTO
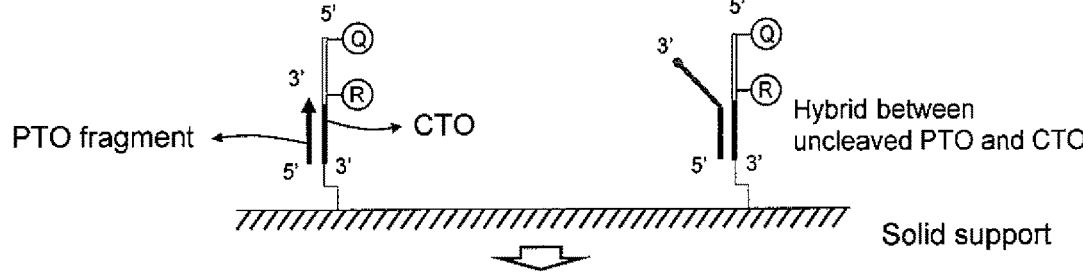
D. Extension of PTO fragment
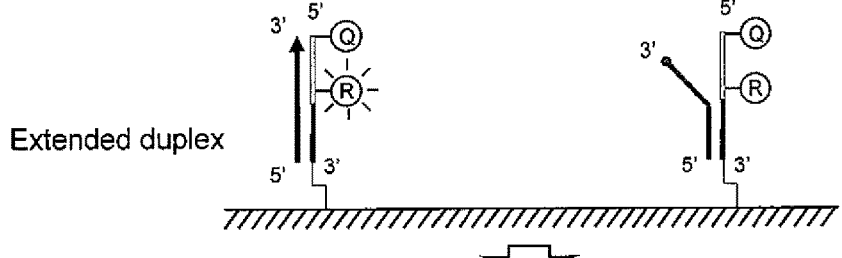
E. Detection at a pre-determined temperature
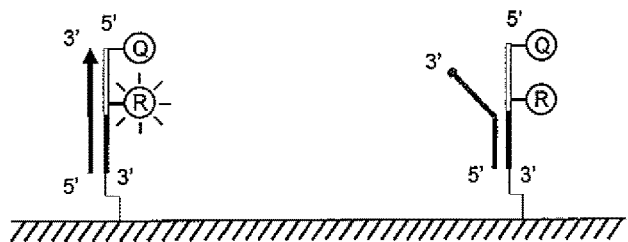

Fig. 10
A. Hybridization
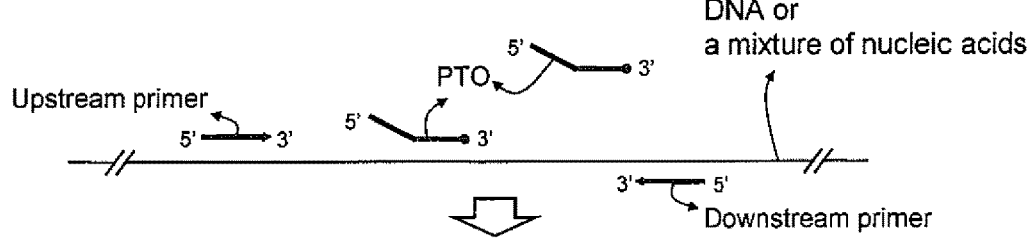
B. Primer extension & Cleavage of PTO
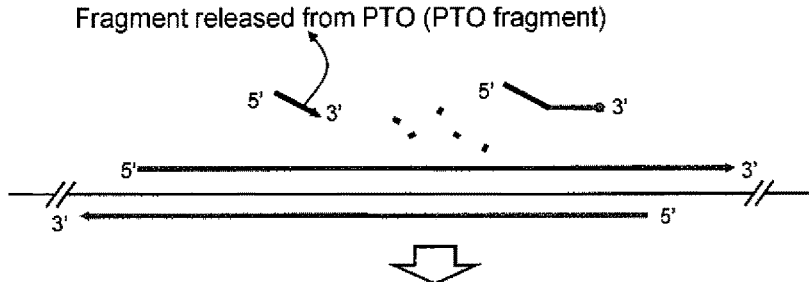
C. Hybridization of PTO fragment to CTO
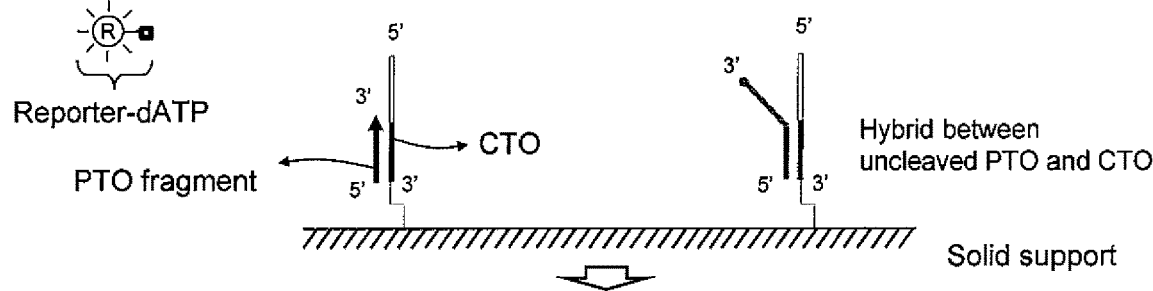
D. Extension of PTO fragment
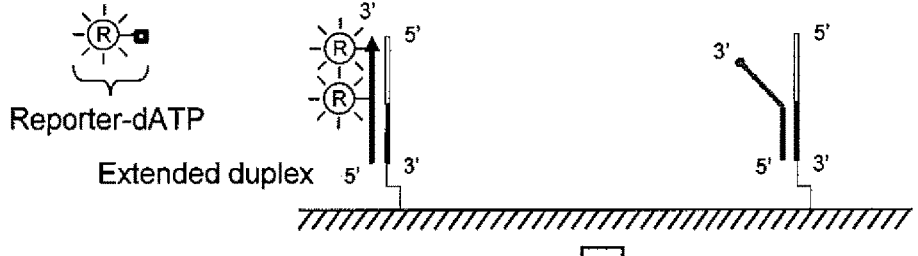
E. Detection at a pre-determined temperature
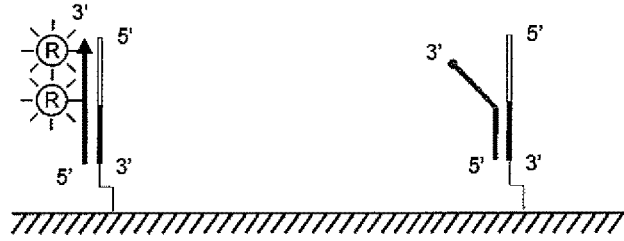

Fig. 11
A. Hybridization
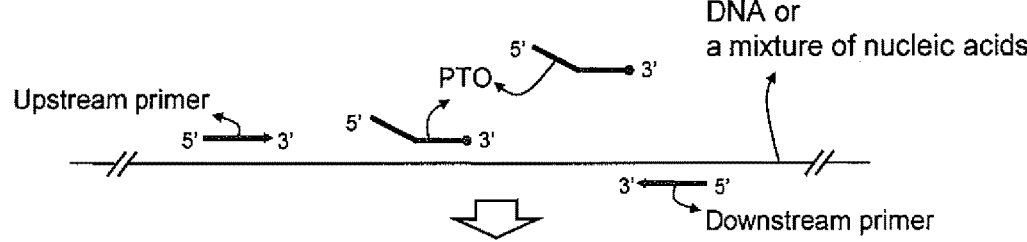
B. Primer extension & Cleavage of PTO
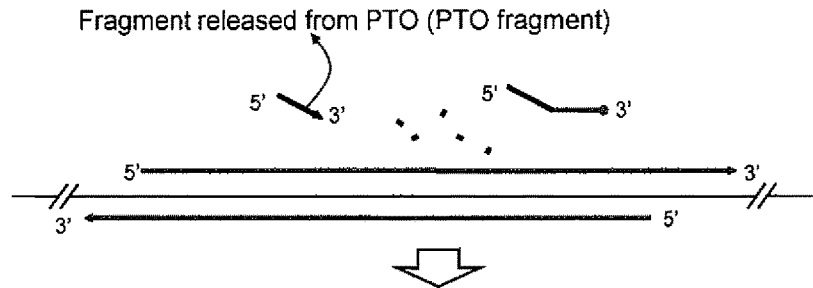
C. Hybridization of PTO fragment to CTO
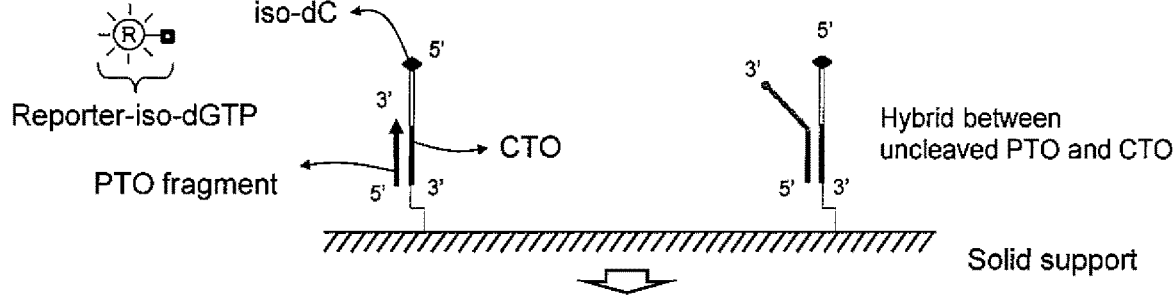
D. Extension of PTO fragment
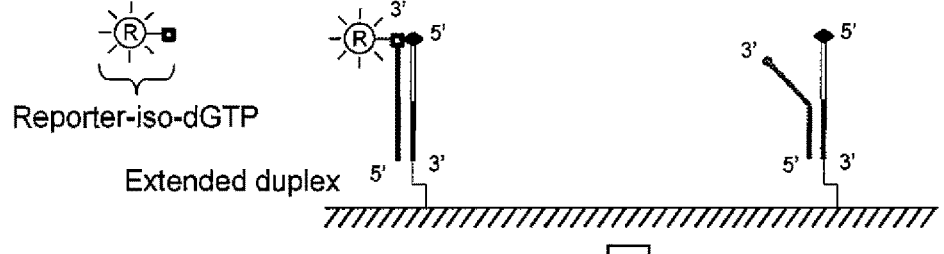
E. Detection at a pre-determined temperature
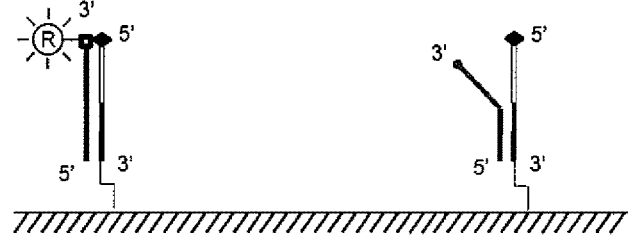

Fig. 12
A. Hybridization
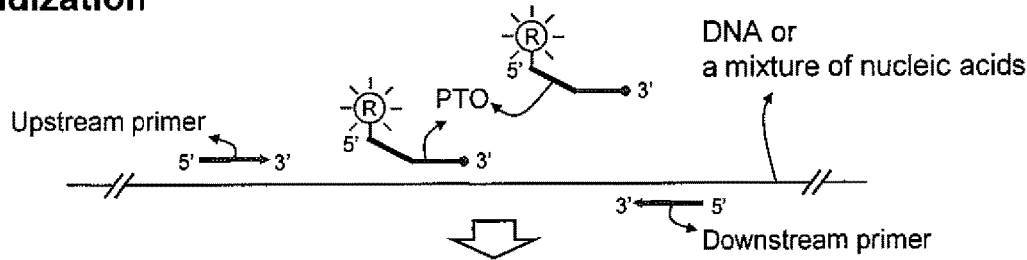
B. Primer extension & Cleavage of PTO
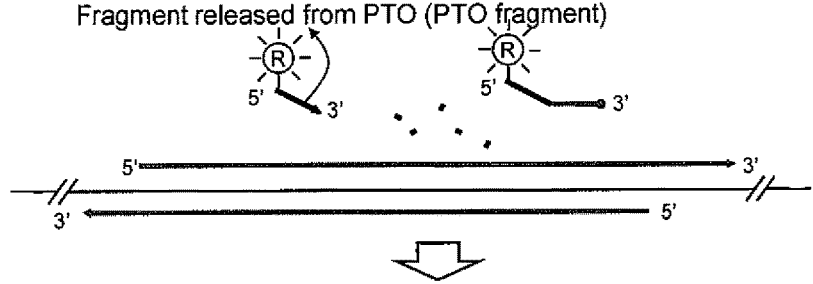
C. Hybridization of PTO fragment to CTO
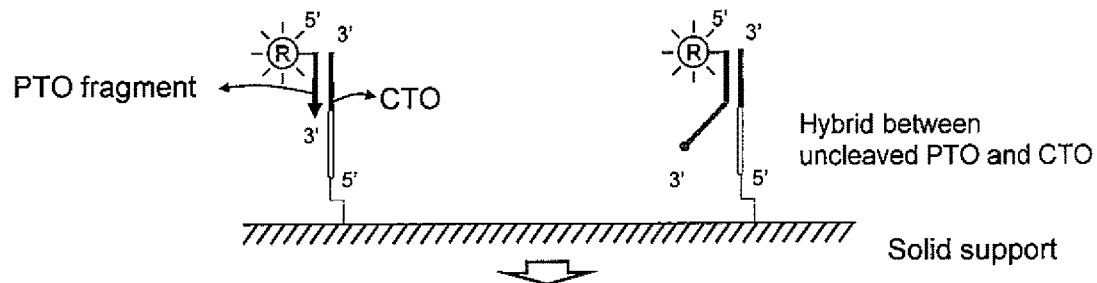
D. Extension of PTO fragment
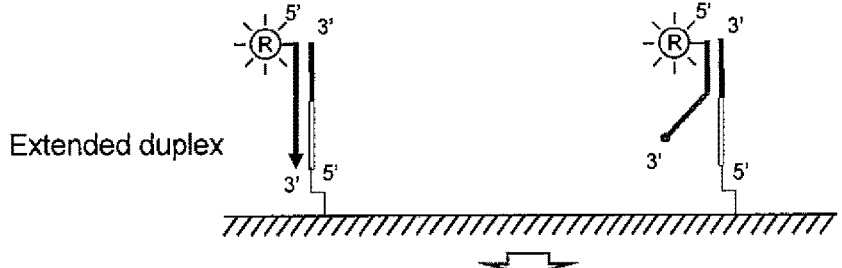
E. Detection at a pre-determined temperature
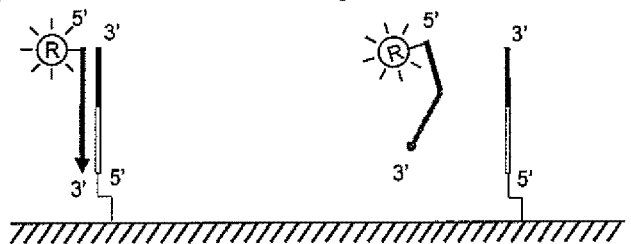

Fig. 13
A. Hybridization
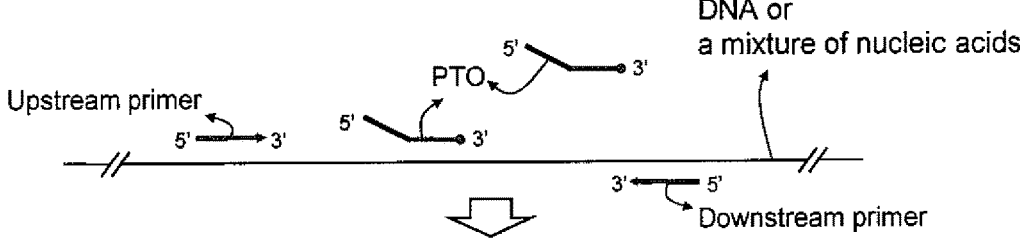
B. Primer extension & Cleavage of PTO
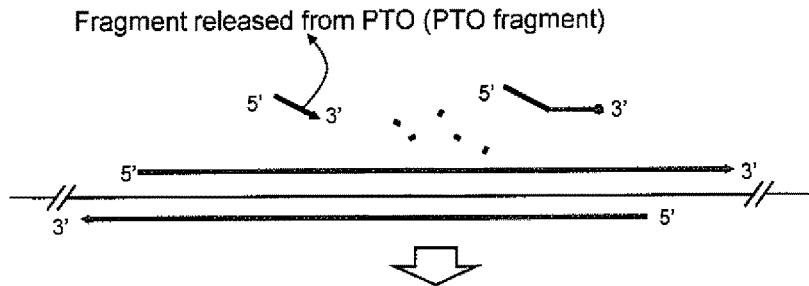
C. Hybridization of PTO fragment to CTO
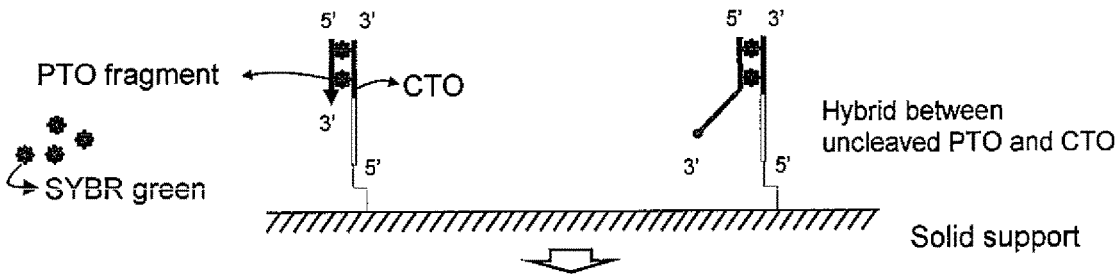
D. Extension of PTO fragment
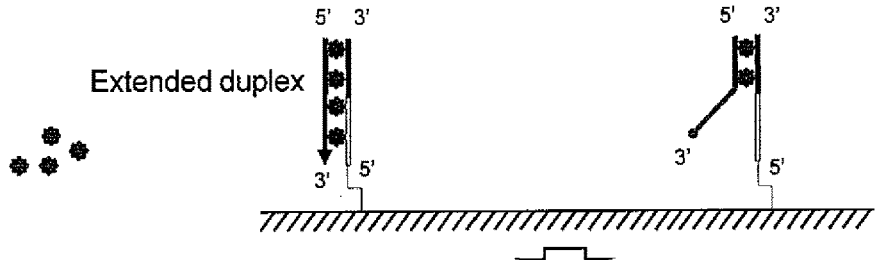
E. Detection at a pre-determined temperature
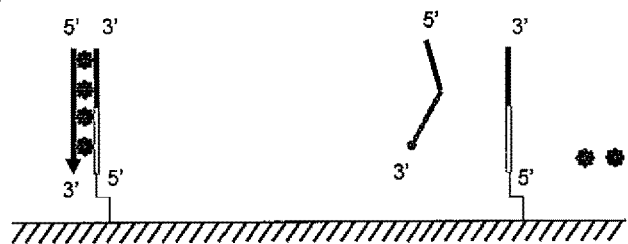

Fig. 14

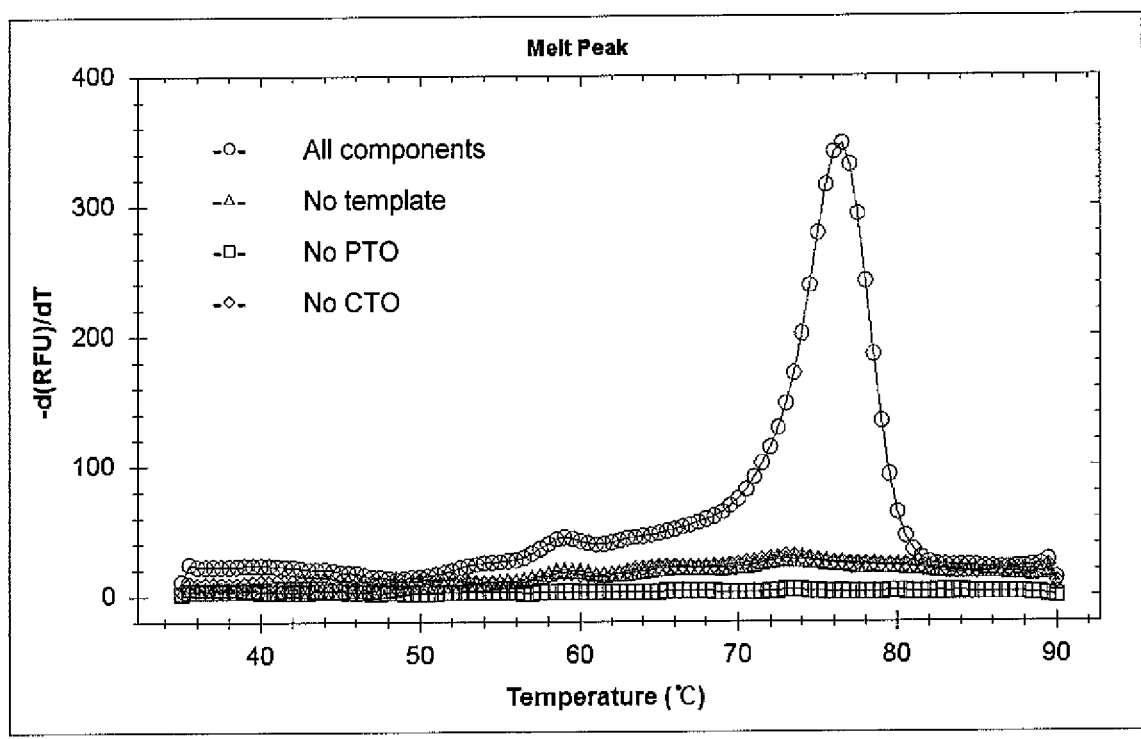

| Template [1] | Upstream primer | PTO [2] | CTO [3] | Tm (°C) | |
|---|---|---|---|---|---|
| | | | | Target [4] | Non-target [5] |
| + | + | + | + | 76.5 | - |
| - | + | + | + | - | - |
| + | + | - | + | - | - |
| + | + | + | - | - | - |

[1] Template is a synthetic oligonucleotide for *Neisseria gonorrhoeae* gene.
[2] PTO has no label.
[3] CTO has a quencher molecule and a fluorescent reporter molecule in the templating portion.
[4] Target represents a target signal which is Tm of the extended duplex.
[5] Non-target represents a non-target signal which is Tm of the hybrid between uncleaved PTO and CTO.

Fig. 15

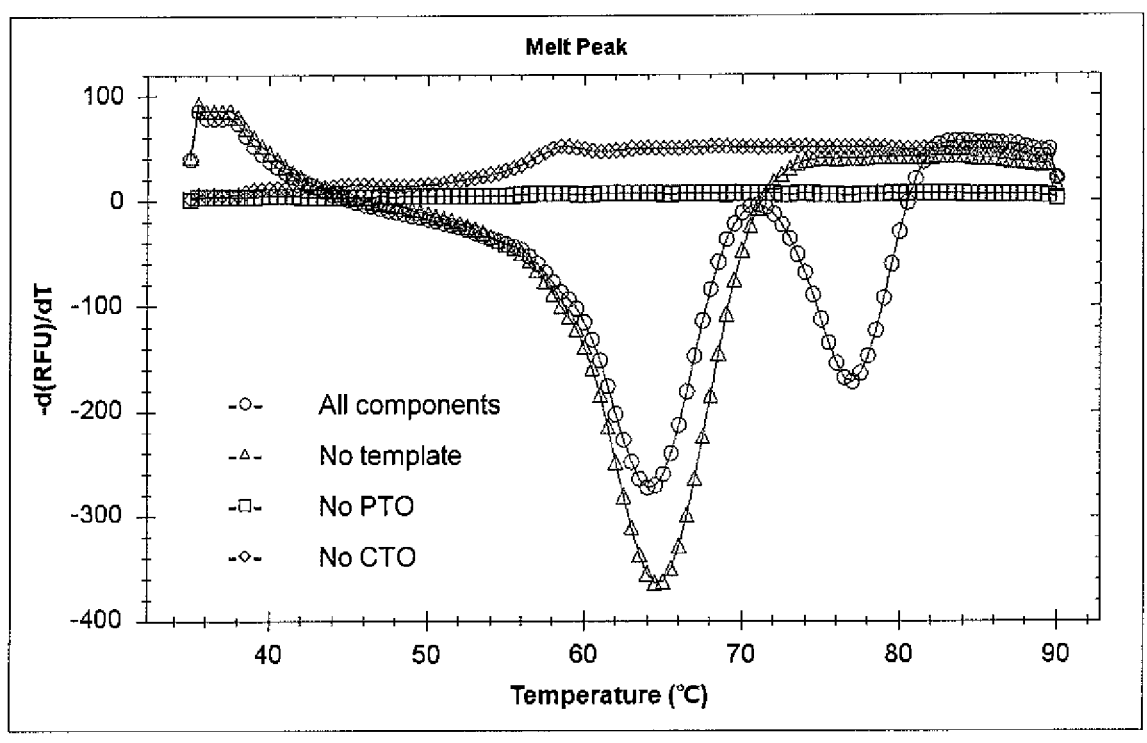

| Template [1] | Upstream primer | PTO [2] | CTO [3] | Tm (°C) | |
|---|---|---|---|---|---|
| | | | | Target [4] | Non-target [5] |
| + | + | + | + | 77.0 | 64.0 |
| - | + | + | + | - | 64.5 |
| + | + | - | + | - | - |
| + | + | + | - | - | - |

[1] Template is a synthetic oligonucleotide for *Neisseria gonorrhoeae* gene.
[2] PTO has a quencher molecular at its 5'-end.
[3] CTO has a fluorescent reporter molecule at its 3'-end.
[4] Target represents a target signal which is Tm of the extended duplex.
[5] Non-target represents a non-target signal which is Tm of the hybrid between uncleaved PTO and CTO .

Fig. 16

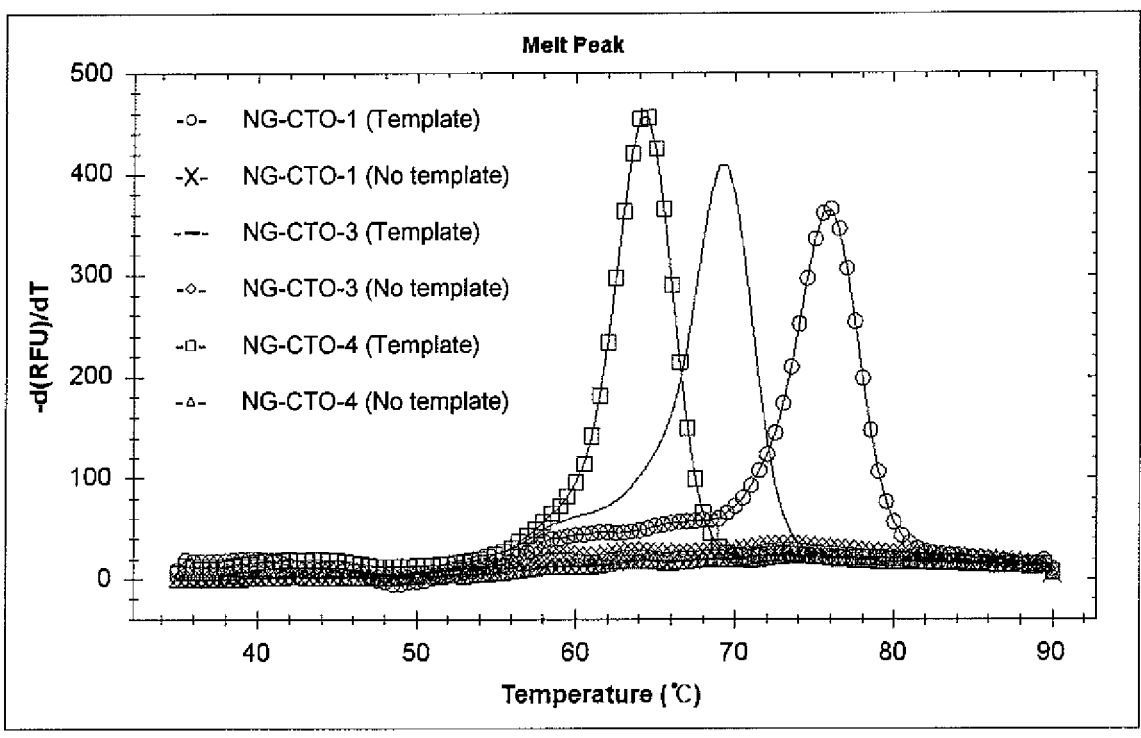

| Template [1] | Upstream primer | PTO [2] | CTO [3] | Tm (°C) [4] |
|---|---|---|---|---|
| + | + | + | NG-CTO-1 | 76.0 |
| - | + | + | NG-CTO-1 | - |
| + | + | + | NG-CTO-3 | 69.0 |
| - | + | + | NG-CTO-3 | - |
| + | + | + | NG-CTO-4 | 64.5 |
| - | + | + | NG-CTO-4 | - |

[1]    Template is a synthetic oligonucleotide for *Neisseria gonorrhoeae* gene.
[2]    PTO has no label.
[3]    CTO has a quencher molecule and a fluorescent reporter molecule in the templating portion. Three CTOs have three different sequences in their templating portions.
[4]    Tm represents melting temperature of the extended duplex.

| Template [1] | Upstream primer | Downstream primer | PTO [2] | CTO [3] | Ct |
|---|---|---|---|---|---|
| + | + | + | + | + | 31.36 |
| - | + | + | + | + | - |

[1] Template is a genomic DNA of *Neisseria gonorrhoeae*.
[2] PTO has no label.
[3] CTO has a quencher molecule and a fluorescent reporter molecule in the templating portion.

| Template [1] | Upstream primer | Downstream primer | PTO [2] | CTO [3] | Tm (°C) [4] |
|---|---|---|---|---|---|
| + | + | + | + | + | 76.0 |
| - | + | + | + | + | - |

[1]  Template is a genomic DNA of *Neisseria gonorrhoeae.*

[2]  PTO has no label.

[3]  CTO has a quencher molecule and a fluorescent reporter molecule in the templating portion.

[4]  Tm represents melting temperature of the extended duplex.

| Template [1] | Upstream Primer | Downstream primer | PTO [2] | CTO [3] | Ct |
|---|---|---|---|---|---|
| + | + | + | + | + | 33.03 |
| - | + | + | + | + | - |

[1] Template is a genomic DNA of *Neisseria gonorrhoeae*.

[2] PTO has no label.

[3] CTO has a non-natural nucleotide (iso-dC) labeled with a fluorescence reporter molecule at its 5'-end.

| Template [1] | Upstream Primer | Downstream primer | PTO [2] | CTO [3] | Tm(°C) [4] |
|---|---|---|---|---|---|
| + | + | + | + | + | 70.0 |
| - | + | + | + | + | - |

[1]  Template is a genomic DNA of *Neisseria gonorrhoeae*.

[2]  PTO has no label.

[3]  CTO has a non-natural nucleotide (iso-dC) and a fluorescence reporter molecule at its 5'-end.

[4]  Tm represents melting temperature of the extended duplex.

| Template [1] | Upstream primer | Downstream primer | PTO [2] | CTO [3] | Ct |
|---|---|---|---|---|---|
| + | + | + | + | + | 29.79 |
| - | + | + | + | + | - |

[1] Template is a genomic DNA of *Neisseria gonorrhoeae.*
[2] PTO has a quencher molecular at its 5'- end.
[3] CTO has a fluorescent reporter molecule at its 3'-end.

Fig. 19B

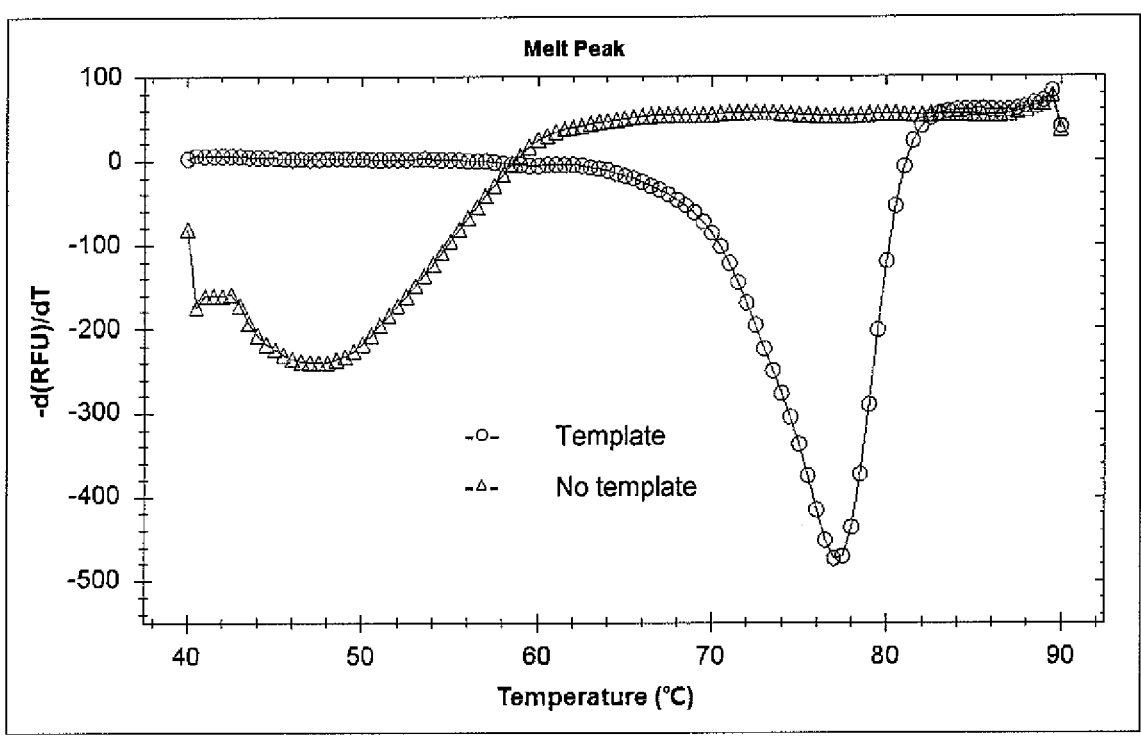

| Template [1] | Upstream primer | Downstream primer | PTO [2] | CTO [3] | Tm (°C) | |
|:---:|:---:|:---:|:---:|:---:|:---:|:---:|
| | | | | | Target [4] | Non-target [5] |
| + | + | + | + | + | 76.5 | - |
| - | + | + | + | + | - | 48.0 |

[1] Template is a genomic DNA of *Neisseria gonorrhoeae*.
[2] PTO has a quencher molecular at its 5'- and.
[3] CTO has a fluorescent reporter molecule at its 3'-end.
[4] Target represents a target signal which is Tm of the extended duplex.
[5] Non-target represents a non-target signal which is Tm of the hybrid between uncleaved PTO and CTO .

Fig. 20

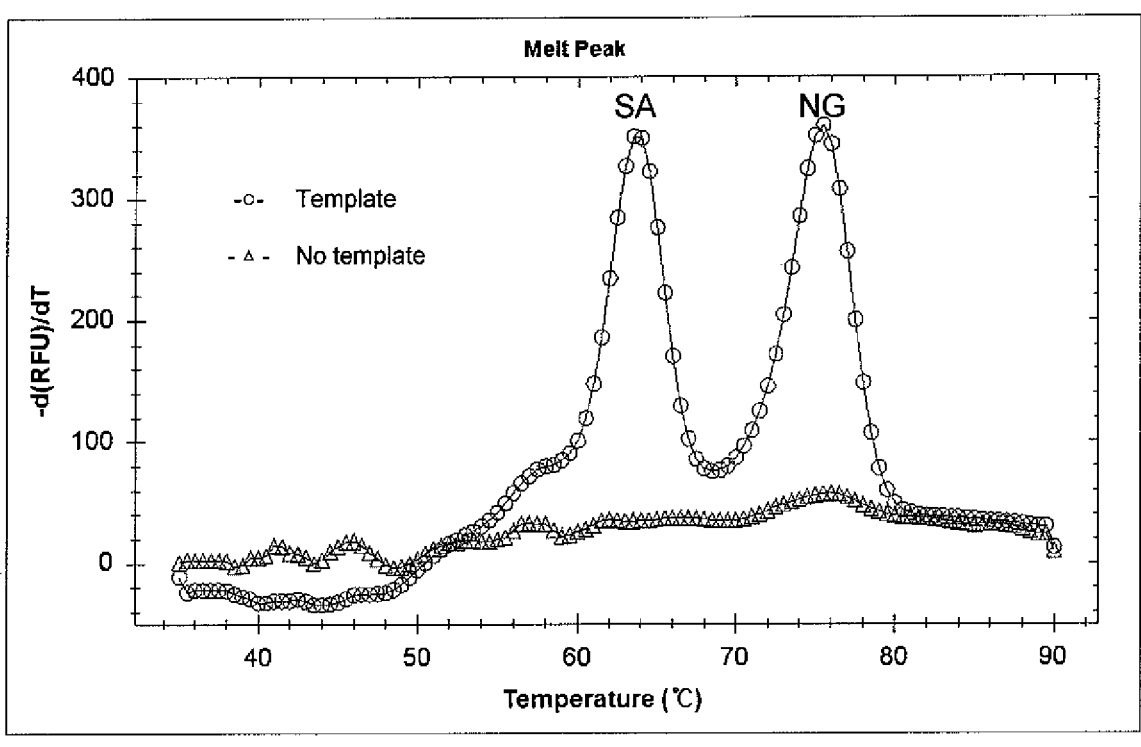

| Templates [1] | Upstream primer | Downstream primer | PTO [2] | CTO [3] | Tm (°C) [4] |
|---|---|---|---|---|---|
| NG and SA | + | + | + | + | 75.5 and 63.5 |
| - | + | + | + | + | - |

[1] Templates are genomic DNAs of *Neisseria gonorrhoeae* (NG) and *Staphylococcus aureus* (SA).

[2] PTO has no label.

[3] CTO has a quencher molecule and a fluorescent reporter molecule in the templating portion. The CTOs for NG and SA have the same type of a fluorescent reporter molecule (FAM).

[4] Tm represents melting temperature of the extended duplex.

Fluorescent image depending temperaute on microarray

Fig. 21B

Fluorescent intensity depending on temperature on microarray

| Template[1] | Upstream primer | PTO [2] | CTO [3] | Relative Fluorescent Units | | | | | |
|---|---|---|---|---|---|---|---|---|---|
| | | | | 44°C | 52°C | 60°C | 68°C | 76°C | 84°C |
| - | + | + | + | 65,438 (±1.4) | 58,761 (±2,249.3) | 9,989 (±473.1) | 1,728 (±188.1) | 862 (±184.6) | 303 (±82.7) |
| + | + | + | + | 65,434 (±3.5) | 65,424 (±11.3) | 65,397 (±9.9) | 65,393 (±12.7) | 40,184 (±3,297.9) | 3,490 (±246.8) |

[1] Template is a synthetic oligonucleotide for *Neisseria gonorrhoeae* gene.

[2] PTO has a fluorescent reporter molecule at its 5'-end.

[3] CTO is immobilized on the surface of solid substrate by using an amino group at its 5'-end.

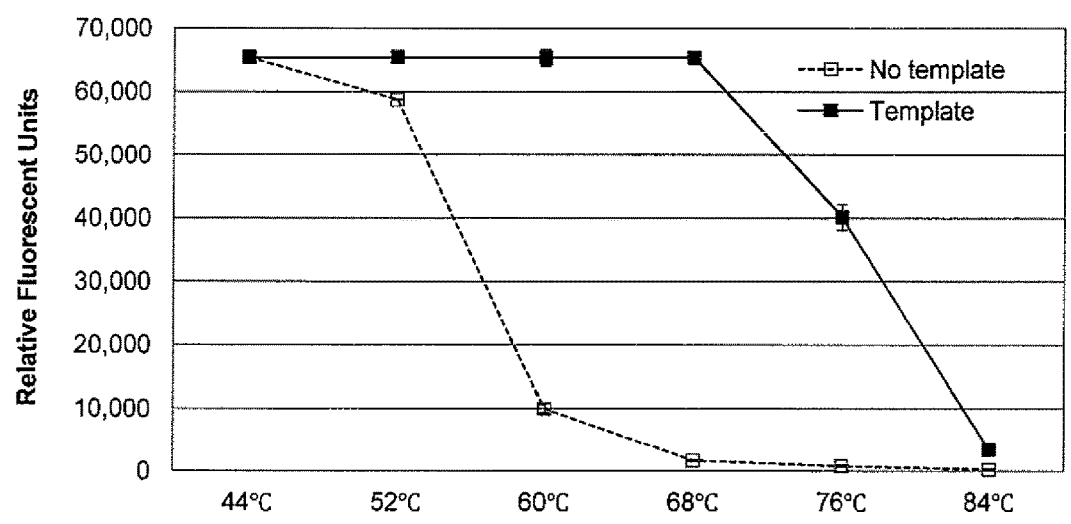

Fluorescent images depending on cycle numbers on microarray

Fig. 22B

Change of fluorescence intensity depending on cycle numbers on microarray

| Template[1] | Upstream primer | PTO[2] | CTO[3] | Relative Fluorescent Units | | | | |
| --- | --- | --- | --- | --- | --- | --- | --- | --- |
| | | | | No. of cycles : 0 | 5 | 10 | 20 | 30 |
| - | + | + | + | 1,216 (±86.3) | 3,012 (±929.1) | 1,988 (±276.5) | 1,961 (±25.5) | 3,261 (±279.3) |
| + | + | + | + | 1,304 (±0.7) | 18,939 (±1,342.1) | 30,619 (±285.0) | 56,248 (±2,208.3) | 64,645 (±1,110.2) |

[1] Template is a synthetic oligonucleotide for *Neisseria gonorrhoeae* gene.

[2] PTO has a fluorescent reporter molecule at its 5'-end.

[3] CTO is immobilized on the surface of solid substrate by using an amino group at its 5'-end.

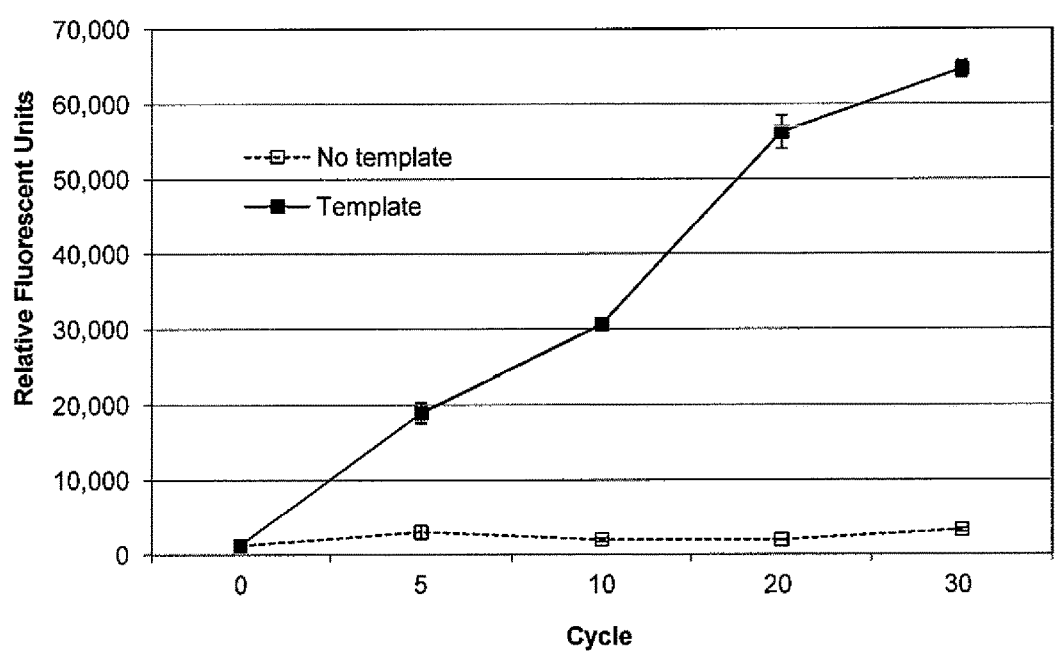

Fluorescent images depending on cycle numbers on microarray

Fig. 23B

Change of fluorescence intensity depending on cycle numbers on microarray

| Template[1] | Upstream primer | PTO [2] | CTO [3] | Relative Fluorescent Units | | | | |
|---|---|---|---|---|---|---|---|---|
| | | | | No. of cycles : | 0 | 5 | 10 | 20 | 30 |
| - | + | + | + | | 21,047 (±334.5) | 17,867 (±478.7) | 19,739 (±82.0) | 19,144 (±176.8) | 21,259 (±1,130.7) |
| + | + | + | + | | 28,078 (±460.3) | 35,967 (±555.1) | 44,674 (±186.0) | 65,423 (±2.1) | 65,426 (±2.8) |

[1] Template is a synthetic oligonucleotide for *Neisseria gonorrhoeae* gene.

[2] PTO has no label.

[3] CTO has a quencher molecule and a fluorescent reporter molecule in the templating portion . CTO is immobilized on the surface of solid substrate by using an amino group at its 3'-end.

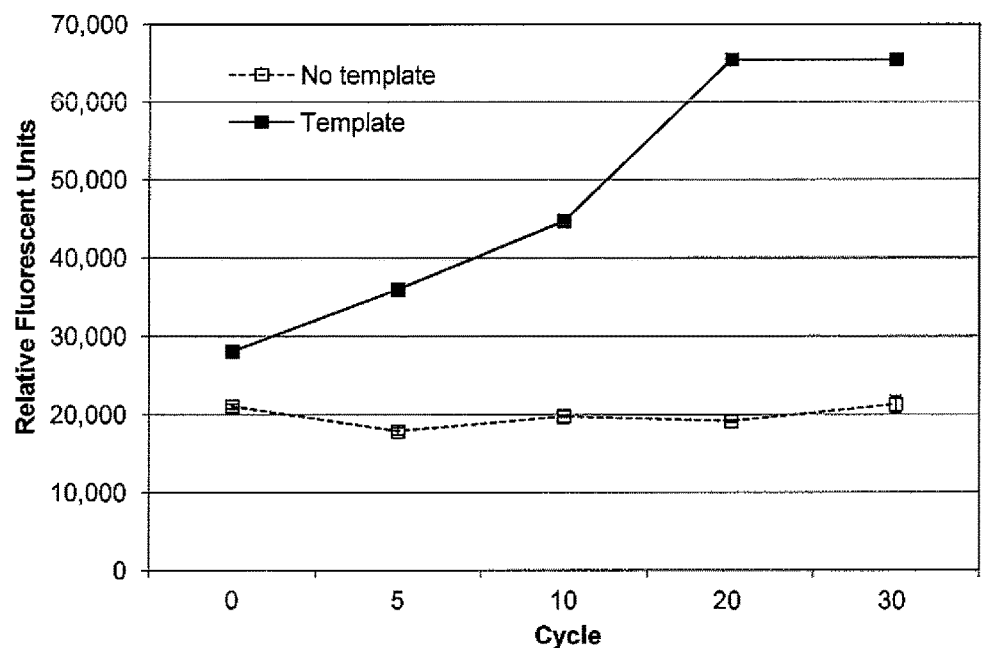

Fig. 24

Fluorescent image on microarray

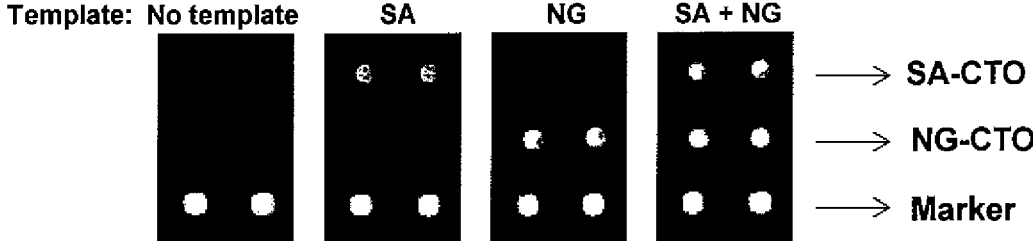

Fluorescent intensity on microarray

| Template [1] | Primers [2] | PTO [3] | CTO [4] | Relative Fluorescent Units | |
|---|---|---|---|---|---|
| | | | | SA | NG |
| - | + | + | + | 448 (±29.7) | 2,522 (±116.0) |
| SA | + | + | + | 65,192 (±198.7) | 4,183 (±323.9) |
| NG | + | + | + | 603 (±36.8) | 65,332 (±1.4) |
| SA and NG | + | + | + | 65,302 (±0.7) | 65,302 (±0.7) |

[1] Template is a genomic DNA of *Staphylococcus aureus* (SA) or/and a genomic DNA of *Neisseria gonorrhoeae* (NG).

[2] Primers are a upstream and a downstream primer for PCR.

[3] PTO has a fluorescent reporter molecule at its 5'-end.

[4] CTO is immobilized on the surface of solid substrate by using an amino group at its 5'-end.

DETECTION OF TARGET NUCLEIC ACID SEQUENCES BY PTO CLEAVAGE AND EXTENSION ASSAY

CROSS-REFERENCE TO RELATED APPLICATIONS

This application is a divisional of and claims priority to U.S. application Ser. No. 16/700,229, filed Dec. 2, 2019, which is a continuation of U.S. application Ser. No. 15/363, 025, filed Nov. 29, 2016, which is a continuation of U.S. application Ser. No. 15/184,412, filed Jun. 16, 2016, which is a continuation of U.S. application Ser. No. 14/337,493, filed Jul. 22, 2014, which is a continuation of U.S. application Ser. No. 13/702,546, filed Dec. 6, 2012, now U.S. Pat. No. 8,809,239, issued Aug. 19, 2014, which is a national phase of PCT/KR2012/000287, filed on Jan. 11, 2012, which claims the benefit of priority to Korean Application Nos. 10-2011-0002840, filed Jan. 11, 2011; 10-2011-0023465, filed Mar. 16, 2011; and PCT Application No. PCT/KR2011/ 004452, filed Jun. 17, 2011, the entire contents of each of which are hereby incorporated in total by reference.

SEQUENCE

This application incorporates by reference the Sequence Listing contained in an ASCII text file named "361406_00051_SeqList.txt" submitted via EFS-Web. The text file was created on Mar. 18, 2022, and is 5.44 kb in size.

FIELD OF THE INVENTION

The present invention relates to the detection of a target nucleic acid sequence by a PTOCE (PTO Cleavage and Extension) assay.

DESCRIPTION OF THE RELATED ART

DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis.

However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected.

By hybridization of fluorescence-labeled probes in a liquid phase, a plurality of target nucleic acid sequences may be simultaneously detected using even a single type of a fluorescent label by melting curve analysis. However, the conventional technologies for detection of target sequences by 5' nuclease-mediated cleavage of interactive-dual labeled probes require different types of fluorescent labels for different target sequences in multiplex target detection, which limits the number of target sequences to be detected due to limitation of the number of types of fluorescent labels.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, preferably multiple target sequences, in a liquid phase and on a solid phase by not only hybridization but also enzymatic reactions such as 5' nucleolytic reaction in a more convenient, reliable and reproducible manner. Furthermore, a novel target detection method not limited by the number of types of labels (particularly, fluorescent labels) is also needed in the art.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences, in which target detection is accomplished by probe hybridization, enzymatic probe cleavage, extension and detection of an extended duplex. The present protocols are well adopted to liquid phase reactions as well as solid phase reactions, and ensure detection of multiple target sequences with more improved accuracy and convenience.

Therefore, it is an object of this invention to provide a method for detecting a target nucleic acid sequence from a DNA or a mixture of nucleic acids by a PTOCE (PTO Cleavage and Extension) assay.

It is another object of this invention to provide a kit for detecting a target nucleic acid sequence from a DNA or a mixture of nucleic acids by a PTOCE (PTO Cleavage and Extension) assay.

Other objects and advantages of the present invention will become apparent from the detailed description to follow taken in conjugation with the appended claims and drawings.

BRIEF DESCRIPTION OF THE DRAWINGS

FIG. 1 shows the schematic structures of PTO (Probing and Tagging Oligonucleotide) and CTO (Capturing and Templating Oligonucleotide) used in PTO cleavage and extension assay (PTOCE assay). Preferably, the 3-ends of the PTO and CTO are blocked to prohibit their extension.

FIG. 2 represents schematically PTOCE assay comprising melting analysis. CTO has a reporter molecule and a quencher molecule at its templating portion.

FIG. 3 represents schematically PTOCE assay comprising melting analysis. CTO has a reporter molecule at its templating portion. The reporter molecule is required to show different signal intensity depending on its presence on a single-stranded form or a double-stranded form.

FIG. 4 represents schematically PTOCE assay comprising melting analysis. CTO has an iso-dC residue and a reporter molecule at its templating portion. Quencher-iso-dGTP is incorporated into the extended duplex during extension reaction.

FIG. 5 represents schematically PTOCE assay comprising melting analysis. PTO has a reporter molecule at its 5'-tagging portion and CTO has an iso-dC residue at its templating portion. Quencher-iso-dGTP is incorporated into the extended duplex during extension reaction.

FIG. 6 represents schematically PTOCE assay comprising melting analysis. PTO has a reporter molecule and a quencher molecule at its 5'-tagging portion.

FIG. 7 represents schematically PTOCE assay comprising melting analysis. PTO has a reporter molecule at its 5'-tagging portion. The reporter molecule is required to show different signal intensity depending on its presence on a single-stranded form or a double-stranded form.

FIG. 8 represents schematically PTOCE assay comprising melting analysis. PTO has a quencher molecule at its 5'-tagging portion and CTO has a reporter molecule at its capturing portion.

FIG. 9 represents schematically PTOCE assay comprising detection at a pre-determined temperature. CTO has a reporter molecule and a quencher molecule at its templating portion. CTO is immobilized on a solid substrate through its 3'-end.

FIG. 10 represents schematically PTOCE assay comprising detection at a pre-determined temperature. A reporter-labeled dATP is incorporated into the extended duplex during extension reaction. CTO is immobilized on a solid substrate through its 3'-end.

FIG. 11 represents schematically PTOCE assay comprising detection at a pre-determined temperature. CTO has an iso-dC residue at its templating portion and a reporter-iso-dGTP is incorporated into the extended duplex during extension reaction. CTO is immobilized on a solid substrate through its 3'-end.

FIG. 12 represents schematically PTOCE assay comprising detection at a pre-determined temperature. PTO has a reporter molecule at its 5'-tagging portion. CTO is immobilized on a solid substrate through its 5'-end.

FIG. 13 represents schematically PTOCE assay comprising detection at a pre-determined temperature with an intercalating dye. CTO is immobilized on a solid substrate through its 5'-end.

FIG. 14 shows the results of the detection of *Neisseria gonorrhoeae* gene by PTOCE assay comprising melting analysis. CTO has a reporter molecule and a quencher molecule at its templating portion.

FIG. 15 shows the results of the detection of *Neisseria gonorrhoeae* gene by PTOCE assay comprising melting analysis. PTO has a quencher molecule at its 5'-end and CTO has a reporter molecule at its 3'-end.

FIG. 16 shows the results that Tm values of extended duplexes are adjusted by CTO sequences.

FIG. 17A shows the results of PTOCE assay comprising real-time PCR detection and FIG. 17B shows the results of PTOCE assay comprising post-PCR melting analysis.

FIG. 18A shows the results of PTOCE assay comprising real-time PCR detection and FIG. 18B shows the results of PTOCE assay comprising post-PCR melting analysis.

FIG. 19A and FIG. 19B show the results of the detection of *Neisseria gonorrhoeae* gene by PTOCE assay with PCR amplification. PTO has a quencher molecule at its 5'-end and CTO has a reporter molecule at its 3'-end. FIG. 19A shows the results of PTOCE assay comprising real-time PCR detection and FIG. 19B show the results of PTOCE assay comprising post-PCR melting analysis.

FIG. 20 shows the results of the simultaneous detection of *Neisseria gonorrhoeae* (NG) gene and *Staphylococcus aureus* (SA) gene by PTOCE assay comprising post-PCR melting analysis. CTO has a reporter molecule and a quencher molecule at its templating portion.

FIG. 21A and FIG. 21B show the results of the detection of *Neisseria gonorrhoeae* gene by PTOCE assay comprising melting analysis on microarray. CTO is immobilized through its 5'-end. PTO has a reporter molecule at its 5'-tagging portion. FIG. 21A depicts the fluorescent image depending on temperature on microarray. FIG. 21B depicts the fluorescent intensity depending on temperature on microarray.

FIG. 22A and FIG. 22B show the results of the detection of *Neisseria gonorrhoeae* gene by PTOCE assay comprising real-time detection at a pre-determined temperature on microarray. CTO is immobilized through its 5'-end. PTO has a reporter molecule at its 5'-tagging portion. FIG. 22A depicts the fluorescent images depending on cycle numbers on microarray. FIG. 22B depicts the change of fluorescence intensity depending on cycle numbers on microarray.

FIG. 23A and FIG. 23B show the results of the detection of *Neisseria gonorrhoeae* gene by PTOCE assay comprising real-time detection at a pre-determined temperature on microarray. CTO is immobilized through its 3'-end and has a reporter molecule and a quencher molecule at its templating portion. FIG. 23A depicts the fluorescent images depending on cycle numbers on microarray. FIG. 23B depicts the change of fluorescence intensity depending on cycle numbers on microarray.

FIG. 24 shows the results of the single or multiple target detection by PTOCE assay comprising end point detection at a pre-determined temperature on microarray. CTO is immobilized through its 5'-end. PTO has a reporter molecule at its 5'-tagging portion. *Neisseria gonorrhoeae* (NG) gene and *Staphylococcus aureus* (SA) gene were used as target nucleic acid sequences.

DETAILED DESCRIPTION OF THIS INVENTION

Figure 17A:
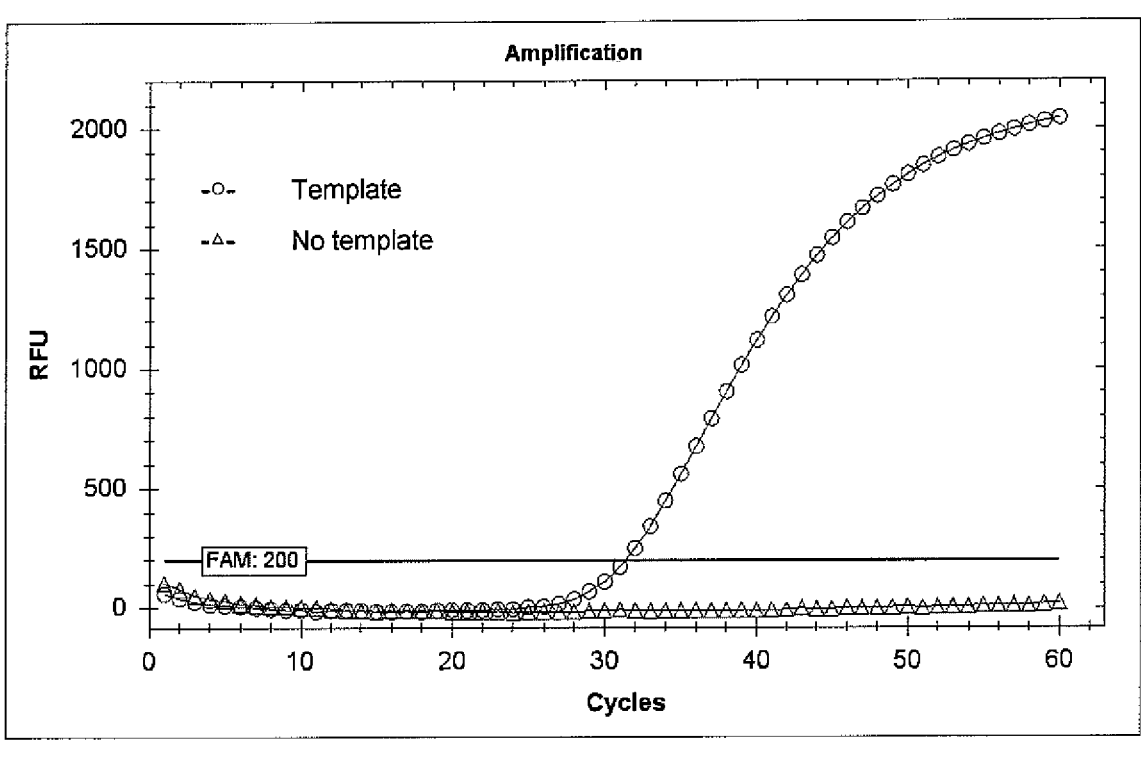
FIG. 17A and FIG. 17B show the results of the detection of *Neisseria gonorrhoeae* gene by PTOCE assay with PCR amplification. CTO has a reporter molecule and a quencher molecule at its templating portion.

The present invention is directed to a novel method for detecting a target nucleic acid sequence by a PTOCE (PTO Cleavage and Extension) assay and a kit for detecting a target nucleic acid sequence by a PTOCE assay.

The present invention involves not only hybridization reactions but also enzymatic reactions that occur depending on the presence of a target nucleic acid sequence.

I. Target Detection Process by PTOCE Comprising Melting Analysis

In one aspect of the present invention, there is provided a method for detecting a target nucleic acid sequence from a DNA or a mixture of nucleic acids by a PTOCE (PTO Cleavage and Extension) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended and an extended duplex is formed; wherein the extended duplex has a T$_m$ value adjustable by (i) a sequence and/or length of the fragment, (ii) a sequence and/or length of the CTO or (iii) the sequence and/or length of the fragment and the sequence and/or length of the CTO;

(e) melting the extended duplex over a range of temperatures to give a target signal indicative of the presence of the extended duplex; wherein the target signal is provided by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) an intercalating label; and (f) detecting the extended duplex by measuring the target signal; whereby the presence of the extended duplex indicates the presence of the target nucleic acid sequence.

The present inventors have made intensive researches to develop novel approaches to detect target sequences with more improved accuracy and convenience, inter alia, in a multiplex manner. As a result, we have established novel protocols for detection of target sequences, in which target detection is accomplished by probe hybridization, enzymatic probe cleavage, extension and detection of an extended duplex. The present protocols are well adopted to liquid phase reactions as well as solid phase reactions, and ensure detection of multiple target sequences with more improved accuracy and convenience.

The present invention employs successive events followed by probe hybridization; cleavage of PTO (Probing and Tagging Oligonucleotide) and extension; formation of a target-dependent extended duplex; and detection of the extended duplex. Therefore, it is named as a PTOCE (PTO Cleavage and Extension) assay.

In the present invention, the extended duplex is characterized to have a label(s) providing a signal indicating the presence of the extended duplex by melting analysis or by detection at a pre-determined temperature. Furthermore, the extended duplex is characterized to have an adjustable T$_m$ value, which plays a critical role in multiple target detection or discrimination from non-target signal.

As the extended duplex is produced only if the target nucleic acid exists, the presence of the extended duplex indicates the presence of the target nucleic acid.

The PTOCE assay comprising melting analysis will be described in more detail as follows:

Step (a): Hybridization of an Upstream Oligonucleotide and a PTO with a Target Nucleic Acid Sequence According to the present invention, a target nucleic acid sequence is first hybridized with an upstream oligonucleotide and a PTO (Probing and Tagging Oligonucleotide).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

Preferably, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with the upstream oligonucleotide and the PTO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press,

8

Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The 5'-tagging portion of the PTO has a nucleotide sequence non-complementary to the target nucleic acid sequence. The templating portion of the CTO (Capturing and Templating Oligonucleotide) has a nucleotide sequence non-complementary to the 5'-tagging portion and the 3'-targeting portion of the PTO. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

The term used herein "PTO (Probing and Tagging Oligonucleotide)" means an oligonucleotide comprising (i) a 3'-targeting portion serving as a probe and (ii) a 5'-tagging portion with a nucleotide sequence non-complementary to the target nucleic acid sequence, which is nucleolytically released from the PTO after hybridization with the target nucleic acid sequence. The 5'-tagging portion and the 3'-targeting portion in the PTO have to be positioned in a 5' to 3' order. The PTO is schematically illustrated in FIG. 1.

Preferably, the hybridization in step (a) is preformed under stringent conditions that the 3'-targeting portion is hybridized with the target nucleic acid sequence and the 5'-tagging portion is not hybridized with the target nucleic acid sequence.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the templating portion of the CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. Preferably, the 3'-end of the PTO is "blocked" to prohibit its extension.

The blocking may be achieved in accordance with conventional methods. For instance, the blocking may be performed by adding to the 3-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3-hydroxyl group of the last nucleotide or using a nucleotide with no 3-hydroxyl group such as dideoxynucleotide.

Alternatively, the PTO may be designed to have a hairpin structure.

The non-hybridization between the 5'-tagging portion of the PTO and the target nucleic acid sequence refers to non-formation of a stable double-strand between them under certain hybridization conditions. According to a preferred embodiment, the 5'-tagging portion of the PTO not involved in the hybridization with the target nucleic acid sequence forms a single-strand.

The upstream oligonucleotide is located upstream of the PTO.

In addition, the upstream oligonucleotide or its extended strand hybridized with the target nucleic acid sequence induces cleavage of the PTO by an enzyme having a 5' nuclease activity.

The induction of the PTO cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO sufficient to induce the PTO cleavage by an enzyme having a 5' nuclease activity, the enzyme bound to the upstream oligonucleotide digests the PTO with no extension reaction. In contrast, where the upstream oligonucleotide is positioned distantly to the PTO, an enzyme having a polymerase activity (e.g., template-dependent polymerase) catalyzes extension of the upstream oligonucleotide (e.g., upstream primer) and an enzyme having a 5' nuclease activity bound to the extended product digests the PTO.

Therefore, the upstream oligonucleotide may be located relatively to the PTO in two fashions. The upstream oligonucleotide may be located adjacently to the PTO sufficient to induce the PTO cleavage in an extension-independent manner. Alternatively, the upstream oligonucleotide may be located distantly to the PTO sufficient to induce the PTO cleavage in an extension-dependent manner.

The term used herein "adjacent" with referring to positions or locations means that the upstream oligonucleotide is located adjacently to the 3'-targeting portion of the PTO to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to a preferred embodiment, the upstream oligonucleotide is located distantly to the PTO sufficient to induce the PTO cleavage in an extension-dependent manner.

According to a preferred embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-part of the 3'-targeting portion of the PTO. Preferably, the overlapped sequence is 1-10 nucleotides, more preferably 1-5 nucleotides, still more preferably 1-3 nucleotides in length. Where the upstream oligonucleotide has a partial-overlapped sequence with the 5'-part of the 3'-targeting portion of the PTO, the 3'-targeting portion is partially digested along with the 5'-tagging portion in the cleavage reaction of the step (b). In addition, the overlapped sequence permits to cleave a desired site of the 3'-targeting portion.

According to a preferred embodiment, the upstream primer induces through its extended strand the cleavage of the PTO by the enzyme having the 5' nuclease activity.

The conventional technologies for cleavage reactions by upstream oligonucleotides may be applied to the present invention, so long as the upstream oligonucleotide induces cleavage of the PTO hybridized with the target nucleic acid sequence to release a fragment comprising the 5'-tagging portion or a part of the 5'-tagging portion of the PTO. For example, U.S. Pat. Nos. 5,210,015, 5,487,972, 5,691,142, 5,994,069 and 7,381,532 and U.S. Appln. Pub. No. 2008-0241838 may be applied to the present invention.

According to a preferred embodiment, the method is performed in the presence of a downstream primer. The downstream primer generates additionally a target nucleic acid sequence to be hybridized with the PTO, enhancing sensitivity in a target detection.

According to a preferred embodiment, when the upstream primer and the downstream primer are used, a template-dependent nucleic acid polymerase is additionally employed for extension of the primers.

According to a preferred embodiment, the upstream oligonucleotide (upstream primer or upstream probe), the downstream primer and/or 5'-tagging portion of the PTO have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, Nucleic Acid Research, 35:6e40(2007)).

According to a preferred embodiment, the 3'-targeting portion of the PTO has a modified dual specificity oligonucleotide (mDSO) structure developed by the present inventor. The modified dual specificity oligonucleotide (mDSO) structure shows significantly improved target specificity compared with conventional probes (see WO 2011/028041).

Step (b): Release of a Fragment from the PTO

Afterwards, the resultant of the step (a) is contacted to an enzyme having a 5' nuclease activity under conditions for cleavage of the PTO. The PTO hybridized with the target nucleic acid sequence is digested by the enzyme having the 5' nuclease activity to release a fragment comprising the 5'-tagging portion or a part of the 5'-tagging portion of the PTO.

The term used herein "conditions for cleavage of the PTO" means conditions sufficient to digest the PTO hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, MgCl$_2$ and temperature.

When the PTO is hybridized with the target nucleic acid sequence, its 3'-targeting portion is involved in the hybridization and the 5'-tagging portion forms a single-strand with no hybridization with the target nucleic acid sequence (see FIG. 2). As such, an oligonucleotide comprising both single-stranded and double-stranded structures may be digested using an enzyme having a 5' nuclease activity by a variety of technologies known to one of skill in the art.

The cleavage sites of the PTO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO, releasing a fragment comprising the 5'-tagging portion or a part of the 5'-tagging portion.

Briefly, there may be three sites of cleavage in the step (b). Firstly, the cleavage site is a junction site between a hybridization portion of the PTO (3'-targeting portion) and a non-hybridization portion (5'-tagging portion). The second cleavage site is a site located several nucleotides in a 3'-direction apart from the 3'-end of the 5'-tagging portion of the PTO. The second cleavage site is located at the 5'-end part of the 3'-targeting portion of the PTO. The third cleavage site is a site located several nucleotides in a 5'-direction apart from the 3'-end of the 5'-tagging portion of the PTO.

According to a preferred embodiment, the initial site for the cleavage of the PTO by the template-dependent polymerase having the 5' nuclease activity upon extension of the upstream primer is a starting point of the double strand between the PTO and the target nucleic acid sequence or a site 1-3 nucleotides apart from the starting point.

In this regard, the term used herein "a fragment comprising the 5'-tagging portion or a part of the 5'-tagging portion of the PTO" in conjunction with cleavage of the PTO by the enzyme having the 5' nuclease activity is used to encompass (i) the 5'-tagging portion, (ii) the 5'-tagging portion and the 5'-end part of the 3'-targeting portion and (iii) a part of the 5'-tagging portion. In this application, the term "a fragment comprising the 5'-tagging portion or a part of the 5'-tagging portion of the PTO" may be also described as "PTO fragment".

The term "part" used in conjunction with the PTO or CTO such as the part of the 5'-tagging portion of the PTO, the 5'-end part of the 3'-targeting portion of the PTO and the 5'-end part of the capturing portion of the CTO refers to a nucleotide sequence composed of 1-40, 1-30, 1-20, 1-15, 1-10 or 1-5 nucleotides, preferably 1, 2, 3 or 4 nucleotides.

According to a preferred embodiment, the enzyme having the 5' nuclease activity is DNA polymerase having a 5' nuclease activity or FEN nuclease, more preferably a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis, Thermis flavus, Thermococcus literalis, Thermus antranikianii, Thermus caldophilus, Thermus chliarophilus, Thermus flavus, Thermus igniterrae, Thermus lacteus, Thermus oshimai, Thermus ruber, Thermus rubens, Thermus*

*scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosipho africanus, Pyrococcus woesei, Pyrococcus horikoshii, Pyrococcus abyssi, Pyrodictium occultum, Aquifex pyrophilus* and *Aquifex aeolieus.* Most preferably, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataricus, Pyrobaculum aerophilum, Thermococcus litoralis, Archaeaglobus venefificus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii, Aeropyrum pernix,* and *Archaeaglobus veneficus.*

Where the upstream primer is used in the step (a), it is preferable that the conditions for cleavage of the PTO comprise extension reaction of the upstream primer.

According to a preferred embodiment, the upstream primer is used in the step (a), a template-dependent polymerase is used for extension of the upstream primer and the template-dependent polymerase is identical to the enzyme having the 5' nuclease activity.

Optionally, the upstream primer is used in the step (a), a template-dependent polymerase is used for extension of the upstream primer and the template-dependent polymerase is different from the enzyme having the 5' nuclease activity.

Step (c): Hybridization of the Fragment Released from the PTO with CTO

The fragment released from the PTO is hybridized with a CTO (Capturing and Templating Oligonucleotide).

The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The CTO is acted as a template for extension of the fragment released from the PTO. The fragment serving as a primer is hybridized with the CTO and extended to form an extended duplex.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

As described above, when the fragment having the 5'-tagging portion of the PTO is released, it is preferred that the capturing portion of the CTO is designed to comprise a nucleotide sequence complementary to the 5'-tagging portion. When the fragment having the 5'-tagging portion and a 5'-end part of the 3'-targeting portion is released, it is preferred that the capturing portion of the CTO is designed to comprise a nucleotide sequence complementary to the 5'-tagging portion and the 5'-end part of the 3'-targeting portion. When the fragment having a part of the 5'-tagging portion of the PTO is released, it is preferred that the capturing portion of the CTO is designed to comprise a nucleotide sequence complementary to the part of the 5'-tagging portion.

Moreover, it is possible to design the capturing portion of the CTO with anticipating cleavage sites of the PTO. For example, where the capturing portion of the CTO is designed to comprise a nucleotide sequence complementary to the 5'-tagging portion, either the fragment having a part of the 5'-tagging portion or the fragment having the 5'-tagging portion can be hybridized with the capturing portion and then extended. Where the fragment comprising the 5'-tagging portion and a 5'-end part of the 3'-targeting portion is released, it may be hybridized with the capturing portion of the CTO designed to comprise a nucleotide sequence complementary to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-3 mismatch nucleotides).

When the fragment comprising the 5'-tagging portion and a 5'-end part of the 3'-targeting portion is released, the 5'-end part of the capturing portion of the CTO may be designed to have a nucleotide sequence complementary to the cleaved 5'-end part of the 3'-targeting portion, overcoming problems associated with mismatch nucleotides (see FIG. 1).

Preferably, the nucleotide sequence of the 5'-end part of the capturing portion of the CTO complementary to the cleaved 5'-end part of the 3'-targeting portion may be selected depending on anticipated cleavage sites on the 3'-targeting portion of the PTO. It is preferable that the nucleotide sequence of the 5'-end part of the capturing portion of the CTO complementary to the cleaved 5'-end part of the 3'-targeting portion is 1-10 nucleotides, more preferably 1-5 nucleotides, still more preferably 1-3 nucleotides.

The 3'-end of the CTO may comprise additional nucleotides not involved in hybridization with the fragment. Moreover, the capturing portion of the CTO may comprise a nucleotide sequence complementary only to a part of the fragment (e.g., a part of the fragment containing its 3'-end portion) so long as it is stably hybridized with the fragment.

The term used "capturing portion comprising a nucleotide sequence complementary to the 5'-tagging portion or a part of the 5'-tagging portion" is described herein to encompass various designs and compositions of the capturing portion of the CTO as discussed above.

The CTO may be designed to have a hairpin structure.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. Preferably, the 3'-end of the CTO is blocked to prohibit its extension. The non-extendible blocking of the CTO may be achieved in accordance with conventional methods. For instance, the blocking may be performed by adding to the 3-hydroxyl group of the last nucleotide of the CTO a chemical moiety such as biotin, labels, a phosphate group, alkyl group, non-nucleotide linker, phosphorothioate or alkane-diol. Alternatively, the blocking may be carried out by removing the 3-hydroxyl group of the last nucleotide or using a nucleotide with no 3-hydroxyl group such as dideoxynucleotide.

The fragment released from the PTO is hybridized with the CTO, providing a form suitable in extension of the fragment. Although an undigested PTO is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

Step (d): Extension of the Fragment

The extension reaction is carried out using the resultant of the step (c) and a template-dependent nucleic acid polymerase. The fragment hybridized with the capturing portion of the CTO is extended to form an extended duplex. In contrast, uncleaved PTO hybridized with the capturing portion of the CTO is not extended such that no extended duplex is formed.

The term used herein "extended duplex" means a duplex formed by extension reaction in which the fragment hybridized with the capturing portion of the CTO is extended using the templating portion of the CTO as a template and the template-dependent nucleic acid polymerase.

The extended duplex has different $T_m$ value from that of the hybrid between the uncleaved PTO and the CTO.

Preferably, the extended duplex has higher $T_m$ value than the hybrid between the uncleaved PTO and the CTO.

The $T_m$ value of the extended duplex is adjustable by (i) a sequence and/or length of the fragment, (ii) a sequence and/or length of the CTO or (iii) the sequence and/or length of the fragment and the sequence and/or length of the CTO.

It is a striking feature of the present invention that the adjustable $T_m$ value of the extended duplex is employed to give a target signal indicative of the presence of the extended duplex by melting the extended duplex in the step (e).

The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$ value may be calculated by conventional methods such as Wallace rule (R. B. Wallace, et al., *Nucleic Acids Research,* 6:3543-3547(1979)) and nearest-neighbor method (SantaLucia J. Jr., et al., *Biochem-*

*istry*, 35:3555-3562(1996)); Sugimoto N., et al., *Nucleic Acids Res.*, 24:4501-4505(1996)).

According to a preferred embodiment, the $T_m$ value refers to actual $T_m$ values under reaction conditions actually practiced.

The template-dependent nucleic acid polymerase used in the step (d) may include any nucleic acid polymerases, for example, Klenow fragment of *E. coli* DNA polymerase I, a thermostable DNA polymerase and bacteriophage T7 DNA polymerase. Preferably, the polymerase is a thermostable DNA polymerase which may be obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosipho africanus*, *Pyrococcus furiosus*(Pfu), *Pyrococcus woesei*, *Pyrococcus horikoshii*, *Pyrococcus abyssi*, *Pyrodictium occultum*, *Aquifex pyrophilus* and *Aquifex aeolieus*. Most preferably, the template-dependent nucleic acid polymerase is Taq polymerase.

According to a preferred embodiment, the enzyme having the 5' nuclease activity used in the step (b) is identical to the template-dependent nucleic acid polymerase used in the step (d). More preferably, the enzyme having the 5' nuclease activity used in the step (b), the template-dependent nucleic acid polymerase used for extension of the upstream primer and the template-dependent nucleic acid polymerase used in the step (d) are identical to one another.

The extended duplex has a label originated from (i) at least one label linked to the PTO fragment and/or the CTO, (ii) a label incorporated into the extended duplex during the extension reaction, (iii) a label incorporated into the extended duplex during the extension reaction and a label linked to the PTO fragment and/or the CTO, or (iv) an intercalating label.

The presence of the extended duplex can indicate the presence of the target nucleic acid sequence because the extended duplex is formed when the target nucleic acid sequence is present. For detecting the presence of the extended duplex in a direct fashion, an extended duplex having a label providing a detectable signal is formed in the step (d). The label used on the extended duplex provides a signal change depending on whether the extended duplex is in a double strand or single strand, finally giving the target signal indicative of the presence of the extended duplex by melting of the extended duplex.

Step (e): Melting of the Extended Duplex

Following the extension reaction, the extended duplex is melted over a range of temperatures to give a target signal indicative of the presence of the extended duplex The target signal is provided by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) an intercalating label.

The term used herein "target signal" means any signal capable of indicating the presence of the extended duplex. For example, the target signal includes a signal from labels (signal generation or extinguishment), a signal change from labels (signal increase or decrease), a melting curve, a melting pattern and a melting temperature (or $T_m$ value).

According to a preferred embodiment, the target signal is a signal change from the label on the extended duplex in the melting step. The signal change may be obtained by measuring signals at not less than two different temperatures. Alternatively, the target signal is a melting curve, a melting pattern and a melting temperature (or $T_m$ value) obtained by measuring signals from the label on the extended duplex over a range of temperatures. Preferably, the range of temperatures is a range of temperatures for a melting curve analysis or temperatures around the $T_m$ value of the extended duplex.

The extended duplex has higher $T_m$ value than the hybrid between the uncleaved PTO and the CTO. Therefore, the extended duplex and the hybrid exhibit different melting patterns from each other. Such different melting patterns permit to discriminate a target signal from non-target signals. The different melting pattern or melting temperature generates the target signal together with a suitable labeling system.

The melting may be carried out by conventional technologies, including, but not limited to, heating, alkali, formamide, urea and glycoxal treatment, enzymatic methods (e.g., helicase action), and binding proteins. For instance, the melting can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The suitable labeling systems used in this invention are various in terms of their types, locations and signal generation fashion.

The labeling systems useful in this invention will be described in detail as follows:

(i) Label Linked to the Fragment and/or the CTO

According to a preferred embodiment, the target signal is provided by at least one label linked to the fragment and/or the CTO. As the extended duplex is formed between the PTO fragment and CTO, either the label on the PTO fragment or on the CTO is present on the extended duplex, providing the target signal in the melting step.

The label includes an interactive dual label and a single label.

(i-1) Interactive Dual Label

The interactive label system is a signal generating system in which energy is passed non-radioactively between a donor molecule and an acceptor molecule. As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively.

Preferably, the signal indicative of the presence of the extended duplex (i.e., the presence of the target nucleic acid sequence) is generated by interactive label systems, more preferably the FRET label system (i.e., interactive dual label system).

First Embodiment (Intrastrand Interactive-Dual Label)

In a first embodiment of an interactive dual label system, the fragment or the CTO has an interactive dual label comprising a reporter molecule and a quencher molecule; wherein the melting of the extended duplex in the step (e) induces change of a signal from the interactive dual label to give the target signal in the step (e). The first embodiment of the interactive dual label system is illustrated in FIGS. 2, 6 and 9. The first embodiment is named as an intrastrand interactive-dual label.

First Embodiment in FIG. 2 (Intrastrand Interactive-Dual Label)

The exemplified embodiment is described with referring to FIG. 2. The templating portion of the CTO has a reporter molecule and a quencher molecule. The PTO hybridized with the target nucleic acid sequence is digested to release the fragment and the fragment is hybridized with the capturing portion of the CTO and extended to form the extended duplex.

When the extended duplex is formed in the step (d), the reporter molecule and the quencher molecule on the CTO are conformationally separated to allow the quencher molecule to unquench the signal from the reporter molecule; wherein when the extended duplex is melted in the step (e), the reporter molecule and the quencher molecule are conformationally adjacent to each other to allow the quencher molecule to quench the signal from the reporter molecule, such that the target signal is given to indicate the presence of the extended duplex in the step (e).

The expression used herein "the reporter molecule and the quencher molecule are conformationally adjacent" means that the reporter molecule and the quencher molecule are three-dimensionally adjacent to each other by a conformational structure of the fragment or CTO such as random coil and hairpin structure.

The expression used herein "the reporter molecule and the quencher molecule are conformationally separated" means that the reporter molecule and the quencher molecule are three-dimensionally separated by change of a conformational structure of the fragment or CTO upon the formation of a double strand.

Preferably, the target signal given in the step (e) includes melting curve, a melting pattern or a $T_m$ value that is obtained by measuring change of the fluorescent signal generated in the step (d).

According to a preferred embodiment, the reporter molecule and the quencher molecule may be located at any site on the CTO, so long as the signal from the reporter molecule is quenched and unquenched depending on melting of the extended duplex.

According to a preferred embodiment, the reporter molecule and the quencher molecule both are linked to the templating portion or to the capturing portion of the CTO.

According to a preferred embodiment, the reporter molecule and the quencher molecule are positioned at 5'-end and 3'-end of CTO.

According to a preferred embodiment, one of the reporter molecule and the quencher molecule on the CTO is located at its 5'-end or at 1-5 nucleotides apart from its 5'-end and the other is located to quench and unquench the signal from the reporter molecule depending on conformation of CTO According to the preferred embodiment, one of the reporter molecule and the quencher molecule on the CTO is located at its 3'-end or at 1-5 nucleotides apart from its 3'-end and the other is located to quench and unquench the signal from the reporter molecule depending on conformation of CTO.

According to a preferred embodiment, the reporter molecule and the quencher molecule are positioned at no more than 80 nucleotides, more preferably no more than 60 nucleotides, still more preferably no more than 30 nucleotides, still much more preferably no more than 25 nucleotides apart from each other. According to a preferred embodiment, the reporter molecule and the quencher molecule are separated by at least 4 nucleotides, more preferably at least 6 nucleotides, still more preferably at least 10 nucleotides, still much more preferably at least 15 nucleotides.

In the present invention, a hybrid between the uncleaved PTO and the CTO may be formed.

Where the templating portion of the CTO is labeled with an interactive dual label as shown in FIG. 2, a signal change from the label on the hybrid between the uncleaved PTO and the CTO is not induced. Therefore, the hybrid does not provide a non-target signal.

Where the capturing portion of the CTO is labeled with an interactive dual label, the hybrid between the uncleaved PTO and the CTO provides a non-target signal in the melting step. In this case, the difference in $T_m$ values of the extended duplex and the hybrid permits to discriminate the target signal of the extended duplex from the non-target signal of the hybrid.

First Embodiment in FIG. 6 (Intrastrand Interactive-Dual Label)

The exemplified embodiment is described with referring to FIG. 6. The 5'-tagging portion of the PTO has a reporter molecule and a quencher molecule. The PTO hybridized with the target nucleic acid sequence is digested to release the fragment comprising the 5'-tagging portion with the reporter molecule and the quencher molecule. The fragment is hybridized with the capturing portion of the CTO.

When the extended duplex is formed in the step (d), the reporter molecule and the quencher molecule on the fragment are conformationally separated to allow the quencher molecule to unquench the signal from the reporter molecule; wherein when the extended duplex is melted in the step (e), the reporter molecule and the quencher molecule are conformationally adjacent to each other to allow the quencher molecule to quench the signal from the reporter molecule, such that the target signal is given to indicate the presence of the extended duplex in the step (e).

According to a preferred embodiment, the reporter molecule and the quencher molecule may be located at any site on the fragment, so long as the signal from the reporter molecule is quenched and unquenched depending on melting of the extended duplex.

According to a preferred embodiment, one of the reporter molecule and the quencher molecule on the fragment is located at its 5'-end or at 1-5 nucleotides apart from its 5'-end and the other is located to quench and unquench the signal from the reporter molecule depending on conformation of the fragment.

According to a preferred embodiment, the reporter molecule and the quencher molecule are positioned at no more than 50 nucleotides, more preferably no more than 40 nucleotides, still more preferably no more than 30 nucleotides, still much more preferably no more than 20 nucleotides apart from each other. According to a preferred embodiment, the reporter molecule and the quencher molecule are separated by at least 4 nucleotides, more preferably at least 6 nucleotides, still more preferably at least 10 nucleotides, still much more preferably at least 15 nucleotides.

As represented in FIG. 6, the hybrid between uncleaved PTO and the CTO provides a non-target signal in the melting step. In this case, the difference in $T_m$ values of the extended duplex and the hybrid permits to discriminate the target signal of the extended duplex from the non-target signal of the hybrid.

Second Embodiment (Interstrand Interactive-Dual Label)

In the second embodiment of the interactive label system, the fragment has one of an interactive dual label comprising a reporter molecule and a quencher molecule and the CTO has the other of the interactive dual label; wherein the melting of the extended duplex in the step (e) induces change of a signal from the interactive dual label to give the target signal in the step (e).

The exemplified embodiment is described with referring to FIG. 8.

When the extended duplex is formed in the step (d), the signal from the reporter molecule linked to the CTO is quenched by the quencher molecule linked to the PTO. When the extended duplex is melted in the step (e), the reporter molecule and the quencher molecule are separated to allow the quencher molecule to unquench the signal from the reporter molecule, such that the target signal is given to indicate the presence of the extended duplex in the step (e).

Preferably, the target signal given in the step (e) includes a melting curve, a melting pattern or a $T_m$ value that is obtained by measuring change of the fluorescent signal from the interactive dual label.

The reporter molecule and the quencher molecule may be located at any site of the PTO fragment and the CTO, so long as the signal from the reporter molecule is quenched by the quencher molecule in the extended duplex.

According to a preferred embodiment, the reporter molecule or the quencher molecule on the PTO fragment is located at the 5'-end of the 5'-tagging portion.

According to a preferred embodiment, the reporter molecule or the quencher molecule on the CTO is located at its 3'-end.

As represented in FIG. 8, the hybrid between the uncleaved PTO and the CTO provides a non-target signal in the melting step. In this case, the difference in $T_m$ values of the extended duplex and the hybrid permits to discriminate the target signal of the extended duplex from the non-target signal of the hybrid.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™

(590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention. Examples of those are BHQ and DABCYL.

In the FRET label adopted to the CTO, the reporter encompasses a donor of FRET and the quencher encompasses the other partner (acceptor) of FRET. For example, a fluorescein dye is used as the reporter and a rhodamine dye as the quencher.

(i-2) Single Label

The present invention is also excellently executed using single label systems for providing signals indicating the presence of target nucleic acid sequences.

According to a preferred embodiment, the fragment or the CTO has a single label, and the melting of the extended duplex in the step (e) induces change of a signal from the single label to give the target signal in the step (e).

First Embodiment in FIG. 3 (Single Label System)

The exemplified embodiment is described with referring to FIG. 3. The templating portion of the CTO has a single fluorescent label. The PTO hybridized with the target nucleic acid sequence is digested to release the fragment. The fragment is hybridized with the capturing portion of the CTO and extended to form the extended duplex. By the formation of the extended duplex, the fluorescent intensity from the single fluorescent label becomes increased. When the extended duplex is melted in the step (e), the fluorescent intensity from the single fluorescent label becomes decreased, such that the target signal is given to indicate the presence of the extended duplex in the step (e).

According to a preferred embodiment, the single label may be located at any site on the CTO, so long as the signal level from the single label is changed depending on melting of the extended duplex.

According to a preferred embodiment, the single label is linked to the templating portion or to the capturing portion of the CTO.

Where the templating portion of the CTO is labeled with a single label as shown in FIG. 3, a signal change from the label on the hybrid between the uncleaved PTO and the CTO is not induced. Therefore, the hybrid does not provide a non-target signal.

Where the capturing portion of the CTO is labeled with a single label, the hybrid between the uncleaved PTO and the CTO provides a non-target signal in the melting step. In this case, the difference in $T_m$ values of the extended duplex and the hybrid permits to discriminate the target signal of the extended duplex from the non-target signal of the hybrid.

Second Embodiment in FIG. 7 (Single Label System)

The exemplified embodiment is described with reference to FIG. 7. The 5'-tagging portion of the PTO has a single fluorescent label. The PTO hybridized with the target nucleic acid sequence is digested to release the fragment comprising the 5'-tagging portion with the single fluorescent label. By the hybridization, the signal intensity from the single fluorescent label on the 5'-tagging portion is increased. When the extended duplex is melted in the step (e), the signal intensity from the single fluorescent label becomes decreased, such that the target signal is given to indicate the presence of the extended duplex in the step (e).

According to a preferred embodiment, the single label may be located at any site on the PTO fragment, so long as the signal level from the single label is changed depending on melting of the extended duplex.

As represented in FIG. 7, the hybrid between the uncleaved PTO and the CTO provides a non-target signal in the melting step. In this case, the difference in $T_m$ values of the extended duplex and the hybrid permits to discriminate the target signal of the extended duplex from the non-target signal of the hybrid.

The single label used herein has to be capable of providing a different signal depending on its presence on a double strand or single strand. The single label includes a fluorescent label, a luminescent label, a chemiluminescent label, an electrochemical label and a metal label. Preferably, the single label includes a fluorescent label.

The types and preferable binding sites of single fluorescent labels used in this invention are disclosed U.S. Pat. Nos. 7,537,886 and 7,348,141, the teachings of which are incorporated herein by reference in their entity. Preferably, the single fluorescent label includes JOE, FAM, TAMRA, ROX and fluorescein-based label. The labeled nucleotide residue is preferably positioned at internal nucleotide residue within the oligonucleotide rather than at the 5'-end or the 3'-end.

The single fluorescent label useful in the present invention may be described with reference to descriptions for reporter and quencher molecules as indicated above.

In particular, where the present invention on a solid phase is performed using a single label, it can utilize a general fluorescent label and does not require a specific fluorescent label capable of providing a fluorescent signal with different intensities depending on its presence on double strand or single strand. The target signal provided on the solid substrate is measured. The embodiment of the single label system with immobilized CTO is illustrated in FIG. 12.

When the CTO immobilized onto a solid substrate is used, chemical labels (e.g. biotin) or enzymatic labels (e.g. alkaline phosphatase, peroxidase, β-galactosidase and β-glucosidase) may be used.

In the labeling system using "label linked to the fragment and/or the CTO", the labels may be positioned to the extent that when a hybrid between an uncleaved PTO and the CTO is formed, the hybrid does not give a non-target signal in the step (e). Alternatively, the labels may be positioned to the extent that when a hybrid between an uncleaved PTO and the CTO is formed, the hybrid gives a non-target signal in the step (e); wherein the $T_m$ value of the extended duplex is higher than that of the hybrid between the uncleaved PTO and the CTO.

Particularly, where the labels are positioned to the extent that a hybrid between an uncleaved PTO and the CTO does not give a non-target signal, the range including $T_m$ value of the hybrid can be utilized to select $T_m$ value of the extended duplex for detecting a target nucleic acid sequence.

(ii) Label Incorporated into the Extended Duplex

The present invention may employ a label incorporated into the extended duplex during the extension reaction for providing the target signal indicative of the presence of the extended duplex.

Although the PTO fragment or CTO has no label, a label incorporated into the extended duplex during the extension reaction is successfully used to allow the extended duplex to be labeled. FIGS. 10 and 11 illustrate an embodiment in which a single-labeled nucleotide is incorporated into the extended duplex during the extension reaction (see C and D of FIGS. 10 and 11). This embodiment is also applicable to other embodiments using a melting analysis.

According to a preferred embodiment, the target signal is provided by a single label incorporated into the extended duplex during the extension reaction; wherein the incorporated single label is linked to a nucleotide incorporated during the extension reaction; wherein the melting of the extended duplex in the step (e) induces change of a signal from the single label to give the target signal in the step (e).

The exemplified embodiment is described with reference to FIG. 10. The PTO hybridized with the target nucleic acid sequence is digested to release the fragment. The fragment is hybridized with the capturing portion of the CTO immobilized on a solid substrate and extended in the presence of nucleotides labeled with the single fluorescent label to form the extended duplex. The fluorescent signal from the extended duplex may be detected on spot of the solid substrate with immobilized CTO. When the extended duplex is melted, a strand having a fluorescent label is released and the fluorescent signal is no longer detected on the spot (not shown in FIG. 10). Therefore, a signal change can be provided on the spot by melting of the extended duplex. In this regard, the target signal is given to indicate the presence of the extended duplex in the step (e).

The target signal given in the step (e) includes a melting curve, a melting pattern or a $T_m$ value that is obtained by measuring change of the fluorescent intensity on the CTO-immobilized spot.

According to a preferred embodiment, a nucleotide incorporated during the extension reaction has a first non-natural base and the CTO has a nucleotide having a second non-natural base with a specific binding affinity to the first non-natural base, as illustrated in FIG. 11. The nucleotide having the second non-natural base is preferably located at any site on the templating portion of the CTO.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432, 272, 5,965,364, 6,001,983, and 6,037,120. The base pairing between non-natural bases involves two or three hydrogen bonds as natural bases. The base pairing between non-natural bases is also formed in a specific manner.

Specific examples of non-natural bases include the following bases in base pair combinations: iso-C/iso-G, iso-dC/iso-dG, K/X, H/J, and M/N (see U.S. Pat. No. 7,422, 850).

The exemplified embodiment is described with reference to FIG. 11. The fragment is hybridized with the CTO with a nucleotide having a second non-natural base (e.g., iso-dC) with a specific binding affinity to a first non-natural base (e.g., iso-dG). The extension is carried out in the presence of a nucleotide having the first non-natural base labeled with a single fluorescent label, forming the extended duplex. In the extension reaction, the nucleotide having the first non-natural base is incorporated at an opposition site to the nucleotide having the second non-natural base.

The fluorescent signal from the extended duplex may be detected on spot of a solid substrate with immobilized CTO. When the extended duplex is melted, a strand having a fluorescent label is released and the fluorescent signal is no longer detected on the spot (not shown in FIG. 11). Therefore, a signal change can be provided on the spot by melting of the extended duplex. In this regard, the target signal is given to indicate the presence of the extended duplex in the step (e).

Where the label incorporated into the extended duplex during the extension reaction is employed, the label is not incorporated into the hybrid between the uncleaved PTO and the CTO because the hybrid is not extended. Therefore, the hybrid does not provide a non-target signal.

The types and characteristics of the single labels used may be described with reference to descriptions for the labeling system using "label linked to the fragment and/or the CTO" as indicated hereinabove.

(iii) Label Incorporated into the Extended Duplex and Label Linked to the Fragment or the CTO The present invention may employ a labeling system using cooperation of a label incorporated into the extended duplex during the extension reaction and a label linked to the fragment and/or the CTO, as illustrated in FIGS. 4 and 5.

According to a preferred embodiment, the target signal is provided by a label incorporated into the extended duplex during the extension reaction and a label linked to the fragment and/or the CTO, and the incorporated label is linked to a nucleotide incorporated during the extension reaction; wherein the two labels are an interactive dual label of a reporter molecule and a quencher molecule; wherein the melting of the extended duplex in the step (e) induces change of a signal from the interactive dual label to give the target signal in the step (e).

More preferably, the nucleotide incorporated during extension reaction has a first non-natural base and the CTO has a nucleotide having a second non-natural base with a specific binding affinity to the first non-natural.

The exemplified embodiment is described with reference to FIG. 4. The fragment is hybridized with the CTO comprising a reporter or quencher molecule and a nucleotide having a second non-natural base (e.g., iso-dC) which is a specific binding affinity to a first non-natural base (e.g., iso-dG). The extension is carried out in the presence of a nucleotide having the first non-natural base labeled with a quencher or reporter molecule, forming the extended duplex in which the signal from the reporter molecule is quenched by the quencher molecule. In the extension reaction, the nucleotide having the first non-natural base is incorporated at an opposition site to the nucleotide having the second non-natural base.

When the extended duplex is melted in the step (e), the reporter molecule and the quencher molecule are separated to allow the quencher molecule to unquench the signal from the reporter molecule, such that the target signal is given to indicate the presence of the extended duplex in the step (e).

Preferably, the target signal given in the step (e) includes a melting curve, a melting pattern or a $T_m$ value that is obtained by measuring change of the signal from the interactive dual label.

The site of the label on the CTO and the incorporation site of the label incorporated are determined to the extent that the two labels are acted as an interactive dual label for inducing signal change in the melting step.

Still more preferably, the templating portion of the CTO has a reporter or quencher molecule and a nucleotide having a second non-natural base. The extension reaction in the step (d) is performed in the presence of a nucleotide having a quencher or reporter molecule and a first non-natural base with a specific binding affinity to the second non-natural base in the CTO. The two non-natural bases in the extended duplex in the step (d) form a base-pairing to quench a signal from the reporter molecule by the quencher molecule and to induce change of a signal, whereby the target signal is provided. Alternatively, the fragment has a reporter or quencher molecule and the templating portion of the CTO has a nucleotide having a second non-natural base. The extension reaction in the step (d) is performed in the presence of a nucleotide having a quencher or reporter molecule and a first non-natural base with a specific binding affinity to the second non-natural base in the CTO. The two non-natural bases in the extended duplex in the step (d) form a base-pairing to induce change a signal from the reporter molecule by quenching, whereby the target signal is provided.

Another exemplified embodiment is described with reference to FIG. 5. In this embodiment, the fragment having a reporter or quencher molecule is hybridized with the CTO comprising a nucleotide having a second non-natural base (e.g., iso-dC) which is a specific binding affinity to a first non-natural base (e.g., iso-dG). The extension is carried out in the presence of a nucleotide having the first non-natural base labeled with a quencher or reporter molecule, forming the extended duplex in which the signal from the reporter molecule is quenched by the quencher molecule. In the extension reaction, the nucleotide having the first non-natural base is incorporated at an opposition site to the nucleotide having the second non-natural base.

When the extended duplex is formed in the step (d), the reporter molecule and the quencher molecule are conformationally separated to allow the quencher molecule to unquench the signal from the reporter molecule; wherein when the extended duplex is melted in the step (e), the reporter molecule and the quencher molecule are conformationally adjacent to each other to allow the quencher molecule to quench the signal from the reporter molecule, such that the target signal is given to indicate the presence of the extended duplex in the step (e).

Preferably, the target signal given in the step (e) includes a melting curve, a melting pattern or a $T_m$ value that is obtained by measuring change of the signal from the interactive dual label.

The site of the label on the PTO and the incorporation site of the label incorporated are determined to the extent that the two labels are acted as an interactive dual label for inducing signal change in the melting step.

Where the label incorporated into the extended duplex during the extension reaction is employed, the label is not incorporated into the hybrid between the uncleaved PTO and the CTO because the hybrid is not extended. Therefore, the hybrid does not provide a non-target signal in the melting step.

(iv) Intercalating Label

The present invention may employ an intercalating label for providing the target signal indicative of the presence of the extended duplex. The intercalating label is more useful on a solid phase reaction using immobilized CTOs because double-stranded nucleic acid molecules present in samples can generate signals.

Exemplified intercalating dyes useful in this invention include SYBR™ Green I, PO-PRO™-1, BO-PRO™-1, SYTO™ 43, SYTO™ 44, SYTO™ 45, SYTOX™ Blue, POPO™_1, POPO™-3, BOBO™-1, BOBO™-3, LO-PRO™-1, JO-PRO™-1, YO-PRO™ I, TO-PRO™ 1, SYTO™ I1, SYTO™ 13, SYTO™ I15, SYTO™ 16, SYTO™ 20, SYTO™ 23, TOTO™-3, YOYO™ 3, GelStar™ and thiazole orange. The intercalating dyes intercalate specifically into double-stranded nucleic acid molecules to generate signals.

FIG. 13 illustrates an embodiment in which intercalating dyes intercalate between base-pairs of the extended duplex (C and D in FIG. 13). The embodiment is also applicable to another embodiment using a melting analysis.

The exemplified embodiment is described with reference to FIG. 13. The fragment is hybridized with the capturing portion of the CTO immobilized on a solid substrate. The extension is carried out in the presence of an intercalating dye (e.g., SYBR™ Green) and produces the extended duplex with intercalating dyes. The fluorescent signal from the extended duplex on spot of the solid substrate with immobilized CTO may be detected using intercalating fluorescent dyes. When the extended duplex is melted, intercalating fluorescent dyes are released and the fluorescent signal is no longer detected on the spot (not shown in FIG. 13). In this regard, the target signal is given to indicate the presence of the extended duplex in the step (e).

The hybrid between the uncleaved PTO and the CTO provides a non-target signal in the melting step. In this case, the difference in $T_m$ values of the extended duplex and the hybrid permits to discriminate the target signal of the extended duplex from the non-target signal of the hybrid (not shown in FIG. 13).

Preferably, the target signal given in the step (e) includes a melting curve, a melting pattern or a $T_m$ value that is obtained by measuring change of the fluorescent signal generated in the step (d).

Step (f): Detection of Target Signal

Finally, the extended duplex is detected by measuring the target signal given in the step (e), whereby the presence of the extended duplex indicates the presence of the target nucleic acid sequence.

The detection may be carried out in various manners depending on the types of the target signal.

According to a preferred embodiment, the detection of the target signal is carried out by a melting analysis.

The term used herein "melting analysis" means a method in which a target signal indicative of the presence of the extended duplex is obtained by melting of the extended duplex, including a method to measure signals at two different temperatures, melting curve analysis, melting pattern analysis and melting peak analysis. Preferably, the melting analysis is a melting curve analysis.

According to a preferred embodiment, the melting of the step (e) is followed by hybridization to give the target signal indicative of the presence of the extended duplex. In that case, the presence of the extended duplex is detected by hybridization curve analysis.

The melting curve or hybridization curve may be obtained by conventional technologies, for example, as described in U.S. Pat. Nos. 6,174,670 and 5,789,167, Drobyshev et al, *Gene* 188: 45(1997); Kochinsky and Mirzabekov *Human Mutation* 19:343(2002); Livehits et al *J. Biomol. Structure Dynam.* 11:783(1994); and Howell et al *Nature Biotechnology* 17:87(1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

The PTO and CTO may be comprised of naturally occurring dNMPs. Alternatively, the PTO and CTO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PTO and CTO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

As described above, the PTO may be cleaved at a site located in a 3'-direction apart from the 3'-end of the 5'-tagging portion of the PTO. The cleavage site may be located at the 5'-end part of the 3'-targeting portion of the PTO. Where the PTO fragment comprises the 5'-end part of the 3'-targeting portion of the PTO, a site of the CTO hybridized with the 5'-end part of the 3'-targeting portion may comprise a universal base, degenerate sequence or their combination. For instance, if the PTO is cleaved at a site located one nucleotide in a 3'-direction apart from the 3'-end of the 5'-tagging portion of the PTO, it is advantageous that the 5'-end part of the capturing portion of the CTO comprises a universal base for hybridization with the nucleotide. If the PTO is cleaved at a site located two nucleotides in a 3'-direction apart from the 3'-end of the 5'-tagging portion of the PTO, it is advantageous that the 5'-end of the capturing portion of the CTO comprises a degenerate sequence and its 3'-direction-adjacent nucleotide comprises a universal base. As such, where the cleavage of the PTO occurs at various sites of the 5'-end part of the 3'-targeting portion, the utilization of universal bases and degenerate sequences in the CTO is useful. In addition, where the PTOs having the same 5'-tagging portion are used for screening multiple target nucleic acid sequences under upstream primer extension-dependent cleavage induction, the PTO fragments having different 5'-end parts of the 3'-targeting portion may be generated. In such cases, universal bases and degenerate sequences are usefully employed in the CTO. The strategies using universal bases and degenerate sequences in the CTO ensure to use one type or minimal types of the CTO for screening multiple target nucleic acid sequences.

According to a preferred embodiment, the method further comprises repeating the steps (a)-(b), (a)-(d) or (a)-(f) with denaturation between repeating cycles preferably, with a downstream primer. This repetition permits to amplify the target nucleic acid sequence and/or the target signal.

According to a preferred embodiment, the steps (a)-(f) are performed in a reaction vessel or in separate reaction vessels. For example, the steps (a)-(b), (c)-(d) or (e)-(f) may be performed in separate reaction vessels.

According to a preferred embodiment, the steps (a)-(b) and (c)-(f) may be simultaneously or separately even in a reaction vessel depending on reaction conditions (particularly, temperature).

The present invention does not require that target nucleic acid sequences to be detected and/or amplified have any particular sequence or length, including any DNA (gDNA and cDNA) and RNA molecules.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligonucleotide dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The present invention is also useful in detection of a nucleotide variation. Preferably, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic acid sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence.

According to a preferred embodiment, the 3'-end of the upstream primer has a complementary sequence to the nucleotide variation in a target nucleic acid sequence. The 3'-end of the upstream primer having a complementary sequence to the nucleotide variation in the target nucleic acid sequence is annealed to the matching template and extended to induce cleavage of the PTO. The resultant PTO fragment is hybridized with the CTO to provide the target signal. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no generation of the target signal.

Alternatively, it is possible to use PTO cleavage depending on the hybridization of PTO having a complementary sequence to a nucleotide variation in a target nucleic acid sequence. For example, under controlled conditions, a PTO having a complementary sequence to the nucleotide variation in the target nucleic acid sequence is hybridized with the matching template and then cleaved. The resultant PTO fragment is hybridized with the CTO to provide the target signal. While, under the controlled conditions, the PTO is not hybridized with a mismatching template having noncomplementary sequence in the nucleotide variation position and not cleaved. Preferably, in this case, the complementary sequence to the nucleotide variation in the PTO is positioned at its middle of the 3'-targeting portion of the PTO.

Alternatively, it is preferable that the 5'-end part of the 3'-targeting portion of the PTO is positioned to a nucleotide variation in a target nucleic acid sequence for the detection of the nucleotide variation and the 5'-end part of the 3'-targeting portion of the PTO has a complementary sequence to the nucleotide variation in a target nucleic acid sequence.

In an embodiment for the detection of a single nucleotide variation, the 5'-end of the 3'-targeting portion of the PTO has a complementary sequence to the single nucleotide variation in a target nucleic acid sequence. As described above, the cleavage of the PTO hybridized with a matching template may be induced at a site immediately adjacent in a 3'-direction to the 5'-end of the 3'-targeting portion of the PTO, for example, under upstream primer extension-dependent cleavage induction. The 3'-end of the PTO fragment has the complementary nucleotide to the single nucleotide variation. The PTO fragment is hybridized with a CTO having a capturing portion comprising a sequence corresponding to the nucleotide variation and then extended to form the extended duplex, providing the target signal. If the same PTO is hybridized with a mismatching template having the identical sequence to the matching template except for the single nucleotide variation, the cleavage of the PTO may occur at a site two nucleotides apart in a 3'-direction from the 5'-end of the 3'-targeting portion of the PTO. The 3'-end of the PTO fragment has the further cleaved nucleotide than the complementary nucleotide to the single nucleotide variation. Where the site of the CTO hybridized with the additional-cleaved nucleotide is designed to have a non-complementary sequence to the further cleaved nucleotide, the 3'-end of the PTO fragment is not hybridized with the CTO, resulting in no extension of the PTO fragment in a controlled condition. Even if the PTO fragment is extended to form the extended duplex, the duplex has a different $T_m$ value from the duplex derived from hybridization between the PTO and the mismatching template.

According to a preferred embodiment, a cleavage site of the PTO having a complementary sequence to the nucleotide variation at its 5'-end part of the 3'-targeting portion is different depending on hybridization with a matching template or with a mismatching template, such that the PTO fragment released from either hybridization event has different sequence preferably, in its 3'-end part, more preferably, in its 3'-end.

According to a preferred embodiment, the selection of the nucleotide sequence of CTO in consideration of the difference in 3'-end parts of the PTO fragments allows to discriminate the matching template from the mismatching template.

According to a preferred embodiment, the target nucleic acid sequence used in the present invention is a pre-amplified nucleic acid sequence. The utilization of the pre-amplified nucleic acid sequence permits to significantly increase the sensitivity and specificity of target detection of the present invention.

According to a preferred embodiment, the method is performed in the presence of a downstream primer.

The advantages of the present invention may be highlighted in the simultaneous (multiplex) detection of at least two target nucleic acid sequences.

According to a preferred embodiment, the method is performed to detect at least two types (more preferably, at least three types, still more preferably at least five types) of target nucleic acid sequences.

According to a preferred embodiment, the method is performed to detect at least two types (more preferably, at least three types, still more preferably at least five types) of target nucleic acid sequences; wherein the upstream oligonucleotide comprises at least two types (more preferably at least three types, still more preferably at least five types) of oligonucleotides, the PTO comprises at least two types (more preferably at least three types, still more preferably at least five types) of the PTOs and the CTO comprises at least one type (preferably at least two types, more preferably at least three types, still more preferably at least five types) of the CTO; wherein when at least two types of the target nucleic acid sequences are present, the method provides at least two types of the target signals corresponding to the at least two types of the target nucleic acid sequences.

The 5'-tagging portions of the at least two PTOs may have an identical sequence to each other. For instance, where the present invention is carried out for screening target nucleic acid sequences, the 5'-tagging portions of PTOs may have the identical sequence.

Furthermore, a single type of the CTO may used for detection of a plurality of target nucleic acid sequences. For example, where the PTOs having an identical sequence in their 5'-tagging portions are employed for screening target nucleic acid sequences, a single type of the CTO may used.

According to a preferred embodiment, the extended duplexes corresponding to the at least two types of the target nucleic acid sequences have different $T_m$ values from each other.

According to a preferred embodiment, the at least two types of the target signals corresponding to the at least two types of the target nucleic acid sequences are provided from different types of labels from each other.

According to a preferred embodiment, the at least two types of the target signals corresponding to the at least two types of the target nucleic acid sequences are provided from the same type of labels.

According to a preferred embodiment, the at least two type of the target signals corresponding to the at least two types of the target nucleic acid sequences are provided from the same type of labels; wherein the extended duplexes corresponding to the at least two types of the target nucleic acid sequences have different $T_m$ values from each other.

The term used herein "different types of labels" refers to labels with different characteristics of detectable signals. For example, FAM and TAMRA as fluorescent reporter labels are considered as different types of labels because their excitation and emission wavelengths are different from each other.

Where the present invention is performed to simultaneously detect at least two types of the target nucleic acid sequences by melting curve analysis and the extended duplexes corresponding to the at least two types of the target nucleic acid sequences have different $T_m$ values from each other, it is possible to detect at least two types of the target nucleic acid sequences even using a single type of a label (e.g. FAM).

Target Detection Using Immobilized CTO on a Solid Phase

The prominent advantage of the present invention is to be effective in detection of target nucleic acid sequences even on a solid phase such as microarray.

According to a preferred embodiment, the present invention is performed on the solid phase and the CTO is immobilized through its 5'-end or 3'-end onto a solid substrate. In solid phase, the target signal provided on the solid substrate is measured.

Where the immobilized CTO is used, the melting analysis using labeling systems as described above is applicable to the solid phase reaction of the present invention.

According to a preferred embodiment, the target signal is provided by a single label linked to the fragment or by a single label incorporated into the extended duplex during the extension reaction. In particular, where the present invention on a solid phase is performed using a single label, it can utilize a general fluorescent label and does not require a specific fluorescent label capable of providing a fluorescent signal with different intensities depending on its presence on double strand or single strand.

When the CTO immobilized onto a solid substrate is used, chemical labels (e.g. biotin) or enzymatic labels (e.g. alkaline phosphatase, peroxidase, β-galactosidase and β-glucosidase) may be used.

For the solid phase reaction, the CTO is immobilized directly or indirectly (preferably indirectly) through its 5'-end or 3'-end (preferably the 3'-end) onto the surface of the solid substrate. Furthermore, the CTO may be immobilized on the surface of the solid substrate in a covalent or non-covalent manner. Where the immobilized CTOs are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for CTO immobilization. In addition, poly (T) tail or poly (A) tail may serve as linkers.

According to a preferred embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized CTOs on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, Si/SiO$_2$ wafer, germanium, gallium arsenide, carbon, carbon nanotube, polymers (e.g., polystyrene, polyethylene, polypropylene and polyacrylamide), sepharose, agarose and colloids. A plurality of immobilized CTOs in this invention may be immobilized on an addressable region or two or more addressable regions on a solid substrate that may comprise 2-1,000,000 addressable regions. Immobilized CTOs may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because the labels on the CTOs immobilized are physically separated. In this regard, the number of target nucleic acid sequences to be detected by the present invention on the solid phase is not limited.

II. Preferable Embodiment with Amplification of a Target Nucleic Acid Sequence

Preferably, the present invention is carried out simultaneously with amplification of a target nucleic acid sequence using a primer pair composed of an upstream primer and a downstream primer capable of synthesizing the target nucleic acid sequence.

In another aspect of this invention, there is provided a method for detecting a target nucleic acid sequences from a DNA or a mixture of nucleic acids by a PTOCE (PTO Cleavage and Extension) assay, comprising:

(a) hybridizing the target nucleic acid sequences with a primer pair comprising an upstream primer and a downstream primer and a PTO (Probing and Tagging Oligonucleotide); wherein each of the upstream primer and the downstream primer comprise a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the PTO is located between the upstream primer and the downstream primer; wherein the PTO is blocked at its 3'-end to prohibit its extension;

(b) contacting the resultant of the step (a) to a template-dependent nucleic acid polymerase having a 5' nuclease activity under conditions for extension of the primers and for cleavage of the PTO; wherein when the PTO is hybridized with the target nucleic acid sequences, the upstream primer is extended and the extended strand induces cleavage of the PTO by the template-dependent nucleic acid polymerase having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion; wherein the fragment released from the PTO is hybridized with the capturing portions of the CTO;

(d) performing an extension reaction using the resultant of the step (c) and the template-dependent nucleic acid polymerase; wherein the fragment hybridized with the capturing portion of the CTO is extended and an extended duplex is formed; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO;

(e) melting the extended duplex over a range of temperatures to give a target signal indicative of the presence of the extended duplex; wherein the target signal is provided by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) intercalating label; and (f) detecting the extended duplex by measuring the target signal; whereby the presence of the extended duplex indicates the presence of the target nucleic acid sequence.

Since the preferable embodiment of the present invention follows the steps of the present method described above, the common descriptions between them are omitted in order to avoid undue redundancy leading to the complexity of this specification.

According to a preferred embodiment, the method further comprise repeating the steps (a)-(b), (a)-(d) or (a)-(f) with denaturation between repeating cycles. The reaction repetition is accompanied with amplification of the target nucleic acid sequence. Preferably, the amplification is performed in accordance with PCR (polymerase chain reaction) which is disclosed in U.S. Pat. Nos. 4,683,195, 4,683,202, and 4,800,159.

According to a preferred embodiment, the method is performed to detect at least two types of target nucleic acid sequences.

According to a preferred embodiment, the at least two type of the target signals corresponding to the at least two types of the target nucleic acid sequences are provided from the same type of labels; wherein the extended duplexes corresponding to the at least two types of the target nucleic acid sequences have different $T_m$ values from each other.

III. Target Detection Process by PTOCE Comprising Detection at a Pre-Determined Temperature The present invention can be modified to utilize a target signal generated in association with the formation of the extended duplex.

In still another aspect of this invention, there is provided a method for detecting a target nucleic acid sequence from a DNA or a mixture of nucleic acids by a PTOCE (PTO Cleavage and Extension) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to form an extended duplex; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO; wherein the extended duplex provides a target signal by (i) at least one label linked to the fragment and/or CTO, (ii) a label incorporated into the extended duplex during the extension reaction, (iii) at least one label linked to the fragment and/or CTO and a label incorporated into the extended duplex during the extension reaction or (iv) intercalating label; and (e) detecting the extended duplex by measuring the target signal at a predetermined temperature that the extended duplex maintains its double-stranded form, whereby the presence of the extended duplex indicates the presence of the target nucleic acid sequence.

Since the preferable embodiment of the present invention follows the steps of the present method above-described except for the melting step, the common descriptions between them are omitted in order to avoid undue redundancy leading to the complexity of this specification.

The present invention using a melting analysis described hereinabove requires detection of signals from labels at not less than two different temperatures because the target signal is given by measuring signal change provided in melting of the extended duplex.

Unlikely, in this aspect of this invention, the extended duplex per se gives signal capable of discriminating formation from no-formation of the extended duplex and the signal is detected at a predetermined temperature that the extended duplex maintains its double-stranded form, whereby the presence of a target nucleic acid sequence is determined.

The present invention is to measure a target signal in association with the formation of the extended duplex, for detection of the presence of the target nucleic acid sequence.

In the present invention, the extended duplex has a label such that the extended duplex provides a target signal.

Preferably, the target signal includes a signal (signal generation or signal extinguishment) from the label on the extended duplex at a pre-determined temperature.

The labeling in the present invention may be executed in the same manner as that for the method using a melting analysis described above. FIGS. 2-13 may illustrate this aspect of the present invention with a little modification for detection at a pre-determined temperature.

The working principle underlying a target signal from the extended duplex is as follows: (i) the extension of the fragment induces change of a signal from a label to give the target signal; or (ii) the hybridization of the fragment and the CTO induces change of a signal from a label to give the target signal and the extended duplex maintains the target signal.

The exemplified embodiment of the working principle (i) may be described with referring to FIG. 9. Where immobilized CTOs are used, the present invention detects a plurality of target nucleic acid sequences in much more effective manner. The templating portion of the immobilized CTO has a reporter molecule and a quencher molecule. The reporter molecule and the quencher molecule are conformationally adjacent to each other to allow the quencher molecule to quench a signal from the reporter molecule. When the fragment is hybridized with the capturing portion of the CTO, the quencher molecule quenches the signal from the reporter molecule. By the formation of the extended duplex, the reporter molecule and the quencher molecule are conformationally separated to allow the quencher molecule to unquench the signal from the reporter molecule. The target signal is given in the extension step (C and D in FIG. 9).

In FIG. 9, the hybrid between the uncleaved PTO and CTO does not form an extended duplex. Therefore, the quencher molecule is allowed to still quench a signal from the reporter molecule. The hybrid does not provide non-target signal.

The exemplified embodiment for the working principle (ii) may be described with referring to FIG. 6. The figure illustrates the present aspect as well as the method using melting analysis. The 5'-tagging portion of the PTO has a reporter molecule and a quencher molecule. The reporter molecule and the quencher molecule are conformationally adjacent to each other to allow the quencher molecule to quench a signal from the reporter molecule. The PTO hybridized with the target nucleic acid sequence is digested to release the fragment comprising the 5'-tagging portion with the reporter molecule and the quencher molecule, and the fragment is hybridized with the capturing portion of the CTO. By the hybridization, the reporter molecule and the quencher molecule are conformationally separated to allow the quencher molecule to unquench the signal from the reporter molecule. The target signal is given in the fragment hybridization step and the extended duplex maintains the target signal (C and D in FIG. 6).

In FIG. 6, the hybrid between the uncleaved PTO and the CTO provides non-target signal (C and D in FIG. 6) and it is necessary to dissociate the hybrid to remove the non-target signal. Therefore, the temperature for measuring the target signal is determined to dissociate the hybrid. According to a preferred embodiment, the temperature is further determined in consideration of hybrid's $T_m$ value.

According to a preferred embodiment, the extended duplex may be detected at temperatures that the hybrid is partially dissociated.

The predetermined temperature is higher than the hybrid's $T_m$ value minus 10° C., preferably, higher than the hybrid's $T_m$ value minus 5° C., more preferably, higher than the hybrid's $T_m$ value and still more preferably, higher than the hybrid's $T_m$ value plus 5° C.

According to a preferred embodiment, the target signal provided by the extended duplex is given during the extension of the step (d); wherein a hybrid between an uncleaved PTO and the CTO does not provides a non-target signal, as represented in FIGS. 2-4 and 9-11.

According to a preferred embodiment, the target signal provided by the extended duplex is given by the hybridization of the fragment and the CTO in the step (c) and the formation of the extended duplex maintains the target signal in the step (d); wherein a hybrid between an uncleaved PTO and the CTO provides a non-target signal; wherein the predetermined temperature is higher than the hybrid's $T_m$ value, as represented in FIGS. 5-8 and 12-13.

When the hybrid between the uncleaved PTO and CTO provides non-target signal (Panel D in FIG. 6), it is necessary to dissociate the hybrid to remove the non-target signal. Therefore, the temperature for measuring target signal is determined to dissociate the hybrid.

The labeling systems useful in this invention will be described as follows:
(i) Label Linked to the Fragment and/or the CTO
(i-1) Interactive Dual Label In an embodiment of an interactive dual label system, the CTO has an interactive dual label comprising a reporter molecule and a quencher molecule; wherein the extension of the fragment in the step (d) induces change of a signal from the interactive dual label to give the target signal. The first embodiment of the interactive dual label system is illustrated in FIG. 2. The target signal is given with extension-synchronized signal generation.

According to a preferred embodiment, the reporter molecule and the quencher molecule may be located at the templating portion of the CTO.

According to a preferred embodiment, one of the reporter molecule and the quencher molecule on the CTO is located at its 5'-end or at 1-5 nucleotides apart from its 5'-end and the other is located to quench and unquench the signal from the reporter molecule depending on conformation of CTO In an embodiment of an interactive dual label system, the CTO has an interactive dual label comprising a reporter molecule and a quencher molecule; wherein the hybridization of the fragment and the CTO in the step (c) induces change of a signal from the interactive dual label to give the target signal and the extended duplex maintains the target signal.

According to the preferred embodiment, the reporter molecule and the quencher molecule may be located at the capturing portion of the CTO.

According to the preferred embodiment, one the reporter molecule and the quencher molecule on the CTO is located at its 3'-end or at 1-5 nucleotides apart from its 3'-end and the other is located to quench and unquench the signal from the reporter molecule depending on conformation of CTO.

In this embodiment, the hybrid between the uncleaved PTO and the CTO provides non-target signal; wherein the temperature for measuring the target signal is determined with consideration of the $T_m$ value of the hybrid.

In an embodiment of an interactive dual label system, the fragment has an interactive dual label comprising a reporter molecule and a quencher molecule; wherein the hybridization of the fragment and the CTO in the step (c) induces change of a signal from the interactive dual label to give the target signal and the extended duplex maintains the target signal. The first embodiment of the interactive dual label system is illustrated in FIG. 6.

According to the preferred embodiment, one of the reporter molecule and the quencher molecule on the fragment is located at its 5'-end or at 1-5 nucleotides apart from the 5'-end of the fragment and the other is located to quench the signal from the reporter molecule depending on conformation of the fragment.

In this embodiment, the hybrid between the uncleaved PTO and the CTO provides non-target signal; wherein the temperature for measuring the target signal is determined with consideration of the $T_m$ value of the hybrid.

In an embodiment of the interactive label system, wherein the fragment has one of an interactive dual label comprising a reporter molecule and a quencher molecule and the CTO has the other of the interactive dual label; wherein the hybridization of the fragment and the CTO in the step (c) induces change of a signal from the interactive dual label to give the target signal and the extended duplex maintains the target signal. The embodiment of the interactive dual label system is illustrated in FIG. 8.

The reporter molecule and the quencher molecule may be located at any site of the PTO fragment and the CTO, so long as the signal from the reporter molecule is quenched by the quencher molecule.

According to the embodiment, the reporter molecule or the quencher molecule on the PTO fragment is located, preferably, at its 5'-end.

According to the embodiment, the reporter molecule or the quencher molecule on the CTO is located, preferably, at its 5'-end.

In this embodiment, the hybrid between the uncleaved PTO and the CTO provides non-target signal; wherein the temperature for measuring the target signal is determined with consideration of the $T_m$ value of the hybrid.
(i-2) Single Label In an embodiment of a single label system, the CTO has a single label and the extension of the fragment in the step (d) induces change of a signal from the single label to give the target signal. The embodiment of the single label system is illustrated in FIG. 3. The target signal is given with extension-synchronized signal generation.

According to the embodiment, the templating portion of the CTO is labeled with the single label.

In an embodiment of a single label system, the CTO has a single label and the hybridization of the fragment and the CTO in the step (c) induces change of a signal from the interactive dual label to give the target signal and the extended duplex maintains the target signal.

According to the embodiment, the capturing portion of the CTO is labeled with the single label.

In this embodiment, the hybrid between the uncleaved PTO and the CTO provides non-target signal; wherein the temperature for measuring the target signal is determined with consideration of the $T_m$ value of the hybrid.

In an embodiment of a single label system, the fragment has a single label and the hybridization of the fragment and the CTO in the step (c) induces change of a signal from the interactive dual label to give the target signal and the extended duplex maintains the target signal. The embodiment of the single label system is illustrated in FIG. 12.

In this embodiment, the hybrid between the uncleaved PTO and the CTO provides non-target signal; wherein the temperature for measuring the target signal is determined with consideration of the $T_m$ value of the hybrid.

The single label used herein has to be capable of providing a different signal depending on its presence on double strand or single strand. The single label includes a fluorescent label, a luminescent label, a chemiluminescent label, an electrochemical label and a metal label. Preferably, the single label includes a fluorescent label. The types and preferable binding sites of single fluorescent labels used in this invention are disclosed U.S. Pat. Nos. 7,537,886 and 7,348,141, the teachings of which are incorporated herein by reference in their entity. Preferably, the single fluorescent label includes JOE, FAM, TAMRA, ROX and fluorescein-based label. The labeled nucleotide residue is preferably positioned internal nucleotide residue within the oligonucleotide rather than at the 5'-end or the 3'-end.

The single fluorescent label useful in the present invention may be described with reference to descriptions for reporter and quencher molecules as indicated above.

In particular, where the present invention on a solid phase is performed using a single label, it can utilize a general fluorescent label and does not require a specific fluorescent label capable of providing a fluorescent signal with different intensities depending on its presence on double strand or single strand.

When the CTO immobilized onto a solid substrate is used, chemical labels (e.g. biotin) or enzymatic labels (e.g. alkaline phosphatase, peroxidase, β-galactosidase and β-glucosidase) may be used.

In a preferred embodiment, the labels linked to the fragment and/or the CTO are positioned to the extent that when a hybrid between an uncleaved PTO and the CTO is formed, the hybrid does not give a non-target signal in the step (d), as represented in FIGS. 2-3 and 9.

Alternatively, the labels may be positioned to the extent that when a hybrid between an uncleaved PTO and the CTO is formed, the hybrid gives a non-target signal in the step (d); wherein the $T_m$ value of the extended duplex is higher than that of the hybrid between the uncleaved PTO and the CTO as represented in FIGS. 6-8 and 12.

(ii) Label Incorporated into the Extended Duplex

In particular, where the present invention is carried out in a solid phase using an immobilized CTO, this label system becomes more useful to provide the target signal as illustrated in FIGS. 10 and 11.

According to a preferred embodiment, the target signal is provided by a single label incorporated into the extended duplex during the extension reaction; wherein the incorporated single label is linked to a nucleotide incorporated during the extension reaction; wherein the extension of the fragment in the step (d) induces change of a signal from the single label to give the target signal in the step (d).

According to a preferred embodiment, the nucleotide incorporated during the extension reaction has a first non-natural base and the CTO has a nucleotide having a second non-natural base with a specific binding affinity to the first non-natural base, as illustrated in FIG. 11. The nucleotide having the second non-natural base is preferably located at any site on the templating portion of the CTO.

Where the label incorporated into the extended duplex during the extension reaction is employed, the label is not incorporated into the hybrid between the uncleaved PTO and the CTO because the hybrid is not extended. Therefore, the hybrid does not provide a non-target signal.

(iii) Label Incorporated into the Extended Duplex and Label Linked to the Fragment or the CTO The present invention may employ a labeling system using cooperation of a label incorporated into the extended duplex during the extension reaction and a label linked to the fragment and/or the CTO, as illustrated in FIGS. 4 and 5.

According to a preferred embodiment, the target signal is provided by a label incorporated into the extended duplex during the extension reaction and a label linked to the fragment and/or the CTO; wherein the label incorporated is linked to a nucleotide incorporated during the extension reaction; wherein the two labels are an interactive dual label of a reporter molecule and a quencher molecule; wherein the extension of the fragment in the step (d) induces change of a signal from the interactive dual label to give the target signal.

More preferably, the nucleotide incorporated during the extension reaction has a first non-natural base and the CTO has a nucleotide having a second non-natural base with a specific binding affinity to the first non-natural.

Preferably, the target signal given in the step (e) is a signal from the interactive dual label in the step (d).

Where the label incorporated into the extended duplex during the extension reaction is employed, the label is not incorporated into the hybrid between the uncleaved PTO and the CTO because the hybrid is not extended. Therefore, the hybrid does not provide a non-target signal.

(iv) Intercalating Label

The present invention may employ an intercalating label for providing the target signal indicative of the presence of the extended duplex. The intercalating label is more useful on a solid phase reaction using immobilized CTOs because double-stranded nucleic acid molecules present in samples can generate signals.

The exemplified embodiment is described with reference to FIG. 13. The PTO hybridized with the target nucleic acid sequence is digested to release the fragment. The fragment is hybridized with the CTO. The extension is carried out in the presence of an intercalating dye (e.g., SYBR™ Green) and forms the extended duplex with intercalating dyes.

In FIG. 13, the hybrid between the uncleaved PTO and the CTO provides non-target signal (C and D in FIG. 13) and it is necessary to dissociate the hybrid to remove the non-target signal. Therefore, the temperature for measuring the target signal is determined with consideration of the $T_m$ value of the hybrid.

Preferably, the target signal given in the step (e) is a signal from the intercalated dye.

According to a preferred embodiment, the PTO and/or CTO is blocked at its 3'-end to prohibit its extension.

According to a preferred embodiment, the upstream oligonucleotide is an upstream primer or an upstream probe.

According to a preferred embodiment, the upstream oligonucleotide is located adjacently to the PTO to the extent that the upstream oligonucleotide induces cleavage of the PTO by the enzyme having the 5' nuclease activity.

According to a preferred embodiment, the upstream primer induces through its extended strand the cleavage of the PTO by the enzyme having the 5' nuclease activity.

According to a preferred embodiment, the method further comprises repeating the steps (a)-(b), (a)-(d) or (a)-(e) with denaturation between repeating cycles.

According to a preferred embodiment, the steps (a)-(b) and (c)-(e) are performed in a reaction vessel or in separate reaction vessels.

According to a preferred embodiment, the method is performed to detect at least two types of target nucleic acid sequences; wherein the upstream oligonucleotide comprises at least two types of oligonucleotides, the PTO comprises at least two types of the PTOs, and the CTO comprises at least one type of the CTOs; wherein when at least two types of the target nucleic acid sequences are present, the method provides at least two types of the target signals corresponding to the at least two types of the target nucleic acid sequences.

According to a preferred embodiment, the upstream oligonucleotide is an upstream primer and the step (b) uses a template-dependent nucleic acid polymerase for the extension of the upstream primer.

According to a preferred embodiment, the CTO is immobilized through its 5'-end or 3'-end onto a solid substrate and the target signal provided on the solid substrate is measured.

According to a preferred embodiment, the target signal is provided by a single label linked to the fragment or by a sing label incorporated into the extended duplex during the extension reaction.

According to a preferred embodiment, the method is performed in the presence of a downstream primer.

The detection of the step (e) may be performed in a real-time manner, an end-point manner, or a predetermined time interval manner. Where the present invention further comprises repeating the steps (a)-(b), (a)-(d) or (a)-(e), it is preferred that the signal detection is performed for each cycle of the repetition at a predetermined temperature (i.e. real-time manner), at the end of the repetition at a predetermined temperature (i.e. end-point manner) or at each of predetermined time intervals during the repetition at a predetermined temperature. Preferably, the detection may be performed for each cycle of the repetition in a real-time manner to improve the detection accuracy and quantification.

IV. Kits for Target Detection

In further aspect of this invention, there is provided a kit for detecting a target nucleic acid sequence from a DNA or a mixture of nucleic acids by a PTOCE (PTO Cleavage and Extension) assay, comprising:

(a) an upstream oligonucleotide comprising a hybridizing nucleotide sequence complementary to the target nucleic acid sequence;

(b) a PTO (Probing and Tagging Oligonucleotide) comprising (i) a 3'-targeting portion comprising a hybridizing nucleotide sequence complementary to the target nucleic acid sequence and (ii) a 5'-tagging portion comprising a nucleotide sequence non-complementary to the target nucleic acid sequence, wherein the 3'-targeting portion is hybridized with the target nucleic acid sequence and the 5'-tagging portion is not hybridized with the target nucleic acid sequence; the upstream oligonucleotide is located upstream of the PTO; wherein the upstream oligonucleotide or its extended strand induces cleavage of the PTO by an enzyme having a 5' nuclease activity such that the cleavage releases a fragment comprising the 5'-tagging portion or a part of the 5'-tagging portion of the PTO; and (c) a CTO (Capturing and Templating Oligonucleotide) comprising in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO; and the fragment hybridized with the capturing portion of the CTO is extended by a template-dependent nucleic acid polymerase to form an extended duplex.

Since the kit of this invention is constructed to perform the detection method of the present invention described above, the common descriptions between them are omitted in order to avoid undue redundancy leading to the complexity of this specification.

According to a preferred embodiment, the kit further comprises an enzyme having a 5' nuclease activity.

According to a preferred embodiment, the kit further comprises a template-dependent nucleic acid polymerase.

According to a preferred embodiment, the PTO and/or the CTO has at least one label.

According to a preferred embodiment, the kit further comprises a label to be incorporated into the extended duplex during the extension reaction.

According to a preferred embodiment, the kit further comprises a label to be incorporated into the extended duplex during the extension reaction and the PTO and/or the CTO has at least one label.

According to a preferred embodiment, the kit further comprises an intercalating label.

According to a preferred embodiment, the label is a single label or interactive dual label.

According to a preferred embodiment, the kit is used for detection of at least two types of nucleic acid sequences, the upstream oligonucleotide comprises at least two types of oligonucleotides, the PTO comprises at least two types of the PTO and the CTO comprises at least two types of the CTO.

According to a preferred embodiment, the CTO is immobilized through its 5'-end or 3'-end onto a solid substrate.

According to a preferred embodiment, the kit further comprises a downstream primer.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

The features and advantages of this invention will be summarized as follows:

(a) The present invention provides a target-dependent extended duplex in which PTO (Probing and Tagging Oligonucleotide) hybridized with a target nucleic acid sequence is cleaved to release a fragment and the fragment is hybridized with CTO (Capturing and Templating Oligonucleotide) to form an extended duplex. The extended duplex provides a signal (signal generation or extinguishment) or a signal change (signal increase or decrease) indicating the presence of a target nucleic acid sequence.

(b) The presence of the extended duplex is determined by a variety of methods or processes such as melting curve analysis and detection at a pre-determined temperature (e.g. a real-time manner and end-point manner).

(c) The present invention allows to simultaneously detect at least two types of target nucleic acid sequences by melting curve analysis even using a single type of a label (e.g. FAM). In contrast, the conventional multiplex real-time method performed in a liquid phase is seriously suffering from limitation associated with the number of detectable fluorescence labels. The present invention permits to successfully overcome such shortcomings and widen the application of multiplex real-time detection.

(d) The present invention can be performed using a multitude of labeling systems. For example, the labels linked to any site of PTO and/or CTO can be utilized for providing the target signal indicating the extended duplex. Also, labels incorporated into the extended duplex during the extension reaction can be used in the present invention. In addition to this, a combination of such labels can be used. The versatile labeling systems applicable to the present invention allow us to choose a proper labeling system depending on experimental conditions or objectives.

(e) The present invention provides a target-dependent extended duplex which has a pre-determined $T_m$ value adjustable by (i) a sequence and/or length of the fragment, (ii) a sequence and/or length of the CTO or (iii) the sequence and/or length of the fragment and the sequence and/or length of the CTO.

(f) Conventional melting curve analysis using an amplified product depends on the sequence of the amplified product such that it is difficult to obtain a desired $T_m$ value of amplified product. In contrast, the present invention depends on the sequence of an extended duplex not the sequence of an amplified product, permitting to select a desired $T_m$ value of extended duplex. Therefore, the present invention is easily adoptable for the detection of multiple target sequences.

(g) Conventional melting curve analysis using a direct hybridization between labeled probes and target nucleic acid sequences is very likely to generate false positive signals due to non-specific hybridization of probes. In contrast, the present invention employs not only PTO hybridization but also enzymatic cleavage and extension, which overcomes completely problems of false positive signals.

(h) $T_m$ value of conventional melting curve analysis is affected by a sequence variation on the target nucleic acid sequences. However, an extended duplex in the present invention provides a constant $T_m$ value regardless of a sequence variation on the target nucleic acid sequences, permitting to ensure excellent accuracy in melting curve analysis.

(i) It is noteworthy that the sequence of the 5'-tagging portion of PTO and the sequence of CTO can be selected with no consideration of target nucleic acid sequences. This makes it possible to pre-design a pool of sequences for the 5'-tagging portion of PTO and CTO. Although the 3'-targeting portion of the PTO has to be prepared with considering target nucleic acid sequences, the CTO can be prepared in a ready-made fashion with no consideration or knowledge of target nucleic acid sequences. Such features provide prominent advantages in multiple target detection, inter alia, on a microarray assay using CTOs immobilized onto a solid substrate.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of Probing and Tagging Oligonucleotide Cleavage & Extension (PTOCE) Assay A New assay, Probing and Tagging Oligonucleotide Cleavage & Extension (PTOCE) assay, was evaluated whether an extended duplex can provide a target signal for the detection of a target nucleic acid sequence.

For this evaluation, PTOCE assay detecting the presence of an extended duplex by melting analysis was performed (PTOCE assay comprising melting analysis). We used Taq DNA polymerase having a 5' nuclease activity for the extension of upstream primer, the cleavage of PTO and the extension of PTO fragment.

The extended duplex formed during the assay was designed to have an interactive dual label. The interactive dual label in the extended duplex was provided by (i) CTO labeled with a reporter molecule and a quencher molecule (dual-labeled CTO) or (ii) PTO having a quencher molecule and CTO having a reporter molecule (a quencher-labeled PTO and a reporter-labeled CTO). PTO and CTO are blocked with a carbon spacer at their 3'-ends. The synthetic oligonucleotide for *Neisseria gonorrhoeae* (NG) gene was used as a target template.

1-1. PTOCE Assay Using a Dual-Labeled CTO

PTO has no label. CTO has a quencher molecule (BHQ-1) and a fluorescent reporter molecule (FAM) in its templating portion. The sequences of synthetic template, upstream primer, PTO and CTO used in this Example are:

```
NG-T
                                    (SEQ ID NO: 1)
5'-AAATATGCGAAACACGCCAATGAGGGGCATGATGCTTTCTTTT

TGTTCTTGCTCGGCAGAGCGAGTGATACCGATCCATTGAAAAA-3'

NG-R
                                    (SEQ ID NO: 2)
5'-CAATGGATCGGTATCACTCGC-3'

NG-PTO-1
                                    (SEQ ID NO: 3)
5'-ACGACGGCTTGGCTGCCCCTCATTGGCGTGTTTC

G[C3 spacer]-3'

NG-CTO-1
                                    (SEQ ID NO: 4)
5'-[BHQ-1]CCTCCTCCTCCTCCTCCTCC[T(FAM)]CCAGTAAAG

CCAAGCCGTCGT[C3 Spacer]-3'
(Underlined letters indicate the 5'-tagging
portion of PTO)
```

The reaction was conducted in the final volume of 20 μl containing 2 pmole of synthetic template (SEQ ID NO: 1) for NG gene, 10 pmole of upstream primer (SEQ ID NO: 2), 5 pmole of PTO (SEQ ID NO: 3), 2 pmole of CTO (SEQ ID NO: 4) and 10 μl of 2× Master Mix containing 2.5 mM $MgCl_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C. After the reaction, melting curve was obtained by cooling the reaction mixture to 35° C., holding at for 35° C. for 30 sec, and heating slowly at 35° C. to 90° C. The fluorescence was measured continuously during the temperature rise to monitor dissociation of double-stranded DNAs. Melting peak was derived from the melting curve data.

As shown FIG. 14, a peak at 76.5° C. corresponding to the expected Tm value of the extended duplex was detected in the presence of the template. No peak was detected in the absence of the template. Since the hybrid of uncleaved PTO and CTO does not give any signal in this labeling method, there was no peak corresponding to the hybrid of uncleaved PTO and CTO. In case of no PTO or no CTO, any peak was not observed.

1-2. PTOCE Assay Using a Quencher-Labeled PTO and a Reporter-Labeled CTO

PTO is labeled with a quencher molecule (BHQ-1) at its 5'-end. CTO is labeled with a fluorescent reporter molecule (FAM) at its 3'-end.

The sequences of synthetic template, upstream primer, PTO and CTO used in this Example are:

```
NG-T
                                    (SEQ ID NO: 1)
5'-AAATATGCGAAACACGCCAATGAGGGGCATGATGCTTTCTTTT

TGTTCTTGCTCGGCAGAGCGAGTGATACCGATCCATTGAAAAA-3'

NG-R
                                    (SEQ ID NO: 2)
5'-CAATGGATCGGTATCACTCGC-3'

NG-PTO-2
                                    (SEQ ID NO: 5)
5'-[BHQ-1]ACGACGGCTTGGCTTTACTGCCCCTCATTGGCGTG

TTTCG[C3 spacer]-3'

NG-CTO-2
                                    (SEQ ID NO: 6)
5'-CCTCCTCCTCCTCCTCCTCCTCCAGTAAAGCCAAGCCGT

CGT[FAM]-3'
(Underlined letters indicate the 5'-tagging
portion of PTO)
```

The reaction was conducted in the final volume of 20 μl containing 2 pmole of synthetic template (SEQ ID NO: 1) for NG gene, 10 pmole of upstream primer (SEQ ID NO: 2), 5 pmole of PTO (SEQ ID NO: 5), 2 pmole of CTO (SEQ ID NO: 6) and 10 μl of 2× Master Mix containing 2.5 mM MgCl$_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C., 30 sec at 72° C. After the reaction, melting curve was obtained by cooling the reaction mixture to 35° C., holding at for 35° C. for 30 sec, and heating slowly at 35° C. to 90° C. The fluorescence was measured continuously during the temperature rise to monitor dissociation of double-stranded DNAs. Melting peak was derived from the melting curve data.

As shown FIG. 15, a peak at 77.0° C. corresponding to the expected Tm value of the extended duplex was detected in the presence of the template. Since the hybrid of uncleaved PTO and CTO does give a non-target signal in this labeling method, there was a peak at 64.0° C.-64.5° C. corresponding to the expected Tm value of the hybrid of uncleaved PTO and CTO. In case of no PTO or no CTO, any peak was not observed.

These results indicate that a target-dependent extended duplex is produced and the extended duplex provides the target signal indicating the presence of the target nucleic acid sequence.

Example 2: Adjustability of Tm Value of an Extended Duplex

We further examined whether the Tm value of an extended duplex is adjustable by the sequence of CTO in PTOCE assay.

For the examination, we used three types of CTOs having different sequences at their templating portions. PTO has no label. The three types of CTOs have a quencher molecule (BHQ-1) and a fluorescent reporter molecule (FAM) in their templating portions. PTO and CTO are blocked with a carbon spacer at their 3'-ends.

PTOCE assay comprising melting analysis was performed with each of the three types of CTOs.

The sequences of synthetic template, upstream primer, PTO and CTOs used in this Example are:

```
NG-T
                                    (SEQ ID NO: 1)
5'-AAATATGCGAAACACGCCAATGAGGGGCATGATGCTTTCTTTTTGT

TCTTGCTCGGCAGAGCGAGTGATACCGATCCATTGAAAAA-3'

NG-R
                                    (SEQ ID NO: 2)
5'-CAATGGATCGGTATCACTCGC-3'

NG-PTO-3
                                    (SEQ ID NO: 7)
5'-ACGACGGCTTGGCCCCTCATTGGCGTGTTTCG[C3 spacer]-3'

NG-CTO-1
                                    (SEQ ID NO: 4)
5'-[BHQ-1]CCTCCTCCTCCTCCTCCTCC[T(FAM)]

CCAGTAAAGCCAAGCCGTCGT[C3 Spacer]-3'

NG-CTO-3
                                    (SEQ ID NO: 8)
5'-[BHQ-1]TTTTTTTTTTCCTCCTCCTCCTCC[T(FAM)]

AAAGCCAAGCCGTCGT[C3 Spacer]-3'

NG-CTO-4
                                    (SEQ ID NO: 9)
5'-[BHQ-1]TTTTTTTTTTTTTTTTTTAG[T(FAM)]AAAG

CCAAGCCGTCGT[C3 Spacer]-3'
(Underlined letters indicate the 5'-tagging
portion of PTO)
```

The reaction was conducted in the final volume of 20 μl containing 2 pmole of synthetic template (SEQ ID NO: 1) for NG gene, 10 pmole of upstream primer (SEQ ID NO: 2), 5 pmole of PTO (SEQ ID NO: 7), 2 pmole of CTO (SEQ ID NOs: 4, 8, or 9), and 10 μl of 2× Master Mix containing 2.5 mM MgCl$_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C. After the reaction, melting curve was obtained by cooling the reaction mixture to 35° C., holding at for 35° C. for 30 sec, and heating slowly at 35° C. to 90° C. The fluorescence was measured continuously during the temperature rise to monitor dissociation of double-stranded DNAs. Melting peak was derived from the melting curve data.

As shown in FIG. 16, a peak was detected at 76.0° C., 69.0° C. or 64.5° C. in the presence of the template. Each peak corresponds to the expected Tm of the extended duplex generated from the examined CTO. No peak was detected in the absence of the template.

These results indicate that the Tm value of the extended duplex is adjustable by the sequence of CTO.

Example 3: Detection of a Target Nucleic Acid Sequence Using PTOCE Assay Comprising Real-Time Detection or Melting Analysis We further examined whether the PTOCE assay can detect a target nucleic acid sequence in real-time PCR manner (i) or post-PCR melting analysis manner (ii): (i) Cleavage of PTO and extension of PTO fragment were accompanied with the amplification of a target nucleic acid by PCR process and the presence of the extended duplex was detected at a pre-determined temperature in each cycle (PTOCE assay comprising real-time detection at a pre-determined temperature) or; (ii) Cleavage of PTO and extension of PTO fragment were accompanied with the amplification of a target nucleic acid by PCR process and the presence of the extended duplex was detected by post-PCR melting analysis (PTOCE assay comprising melting analysis).

Upstream primer is involved in the PTO cleavage by an enzyme having a 5' nuclease activity and also involved in amplification of the target acid sequence with downstream primer by PCR process. Taq DNA polymerase having a 5' nuclease activity was used for the extension of upstream primer and downstream primer, the cleavage of PTO and the extension of PTO fragment.

The extended duplex was designed to have an interactive dual label. The interactive dual label in the extended duplex was provided by (i) CTO labeled with a reporter molecule and a quencher molecule, (ii) a quencher-iso-dGTP incorporated during extension reaction and CTO having a reporter molecule and an iso-dC residue or (iii) PTO having a quencher molecule and CTO having a reporter molecule. PTO and CTO are blocked with a carbon spacer at their 3'-ends.

Genomic DNA of *Neisseria gonorrhoeae* (NG) was used as a target nucleic acid.

3-1. PTOCE Assay Using a Dual-Labeled CTO

PTO has no label and CTO is labeled with a quencher molecule (BHQ-1) and a fluorescent reporter molecule (FAM) in its templating portion.

The sequences of upstream primer, downstream primer, PTO and CTO used in this Example are:

```
NG-F
                               (SEQ ID NO: 10)
5'-TACGCCTGCTACTTTCACGCT-3'

NG-R
                               (SEQ ID NO: 2)
5'-CAATGGATCGGTATCACTCGC-3'

NG-PTO-3
                               (SEQ ID NO: 7)
5'-ACGACGGCTTGGCCCCTCATTGGCGTGTTTCG[C3 spacer]-3'

NG-CTO-1
                               (SEQ ID NO: 4)
5'-[BHQ-1]CCTCCTCCTCCTCCTCCTCC[T(FAM)]CCAGTAAAG

CCAAGCCGTCGT[C3 Spacer]-3'
(Underlined letters indicate the 5'-tagging
portion of PTO)
```

3-1-1. PTOCE Assay Comprising Real-Time Detection at a Pre-Determined Temperature The reaction was conducted in the final volume of 20 µl containing 100 pg of genomic DNA of NG, 10 pmole of downstream primer (SEQ ID NO: 10), 10 pmole of upstream primer (SEQ ID NO: 2), 5 pmole of PTO (SEQ ID NO: 7), 2 pmole of CTO (SEQ ID NO: 4), and 10 µl of 2× Master Mix containing 2.5 mM $MgCl_2$, 200 µM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 60 cycles of 30 sec at 95° C., 60 sec at 60° C., 30 sec at 72° C. Detection of the signal was performed at 60° C. of each cycle. The detection temperature was determined to the extent that the extended duplex maintains a double-stranded form.

As shown in FIG. 17A, the target signal (Ct 31.36) was detected in the presence of the template. No signal was detected in the absence of the template.

3-1-2. PTOCE Assay Comprising Melting Analysis

After the reaction in Example 3-1-1, melting curve was obtained by cooling the reaction mixture to 35° C., holding at for 35° C. for 30 sec, and heating slowly at 35° C. to 90° C. The fluorescence was measured continuously during the temperature rise to monitor dissociation of double-stranded DNAs. Melting peak was derived from the melting curve data.

Figure 17B:
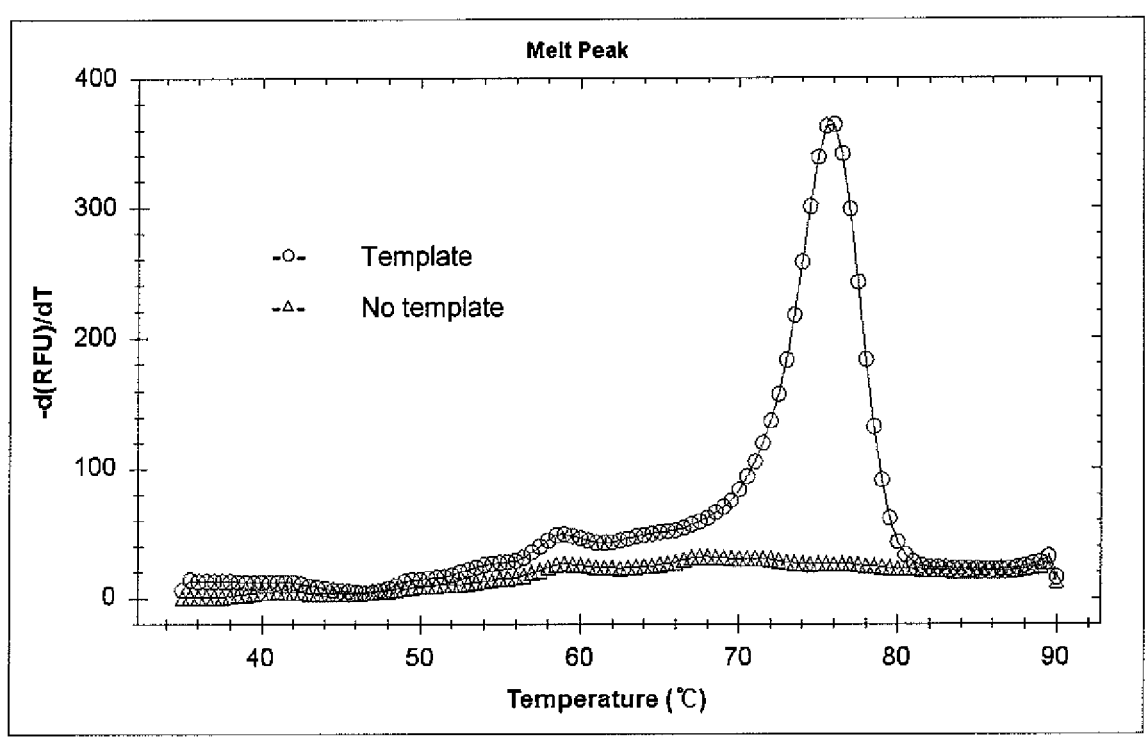

As shown FIG. 17B, a peak at 76.0° C. corresponding to the expected Tm value of the extended duplex was detected in the presence of the template. No peak was detected in the absence of the template. Since the hybrid of uncleaved PTO and CTO does not give any signal in this labeling method, there was no peak corresponding to the hybrid of uncleaved PTO and CTO.

3-2. PTOCE Assay Using a Quencher-Iso-dGTP and a Reporter-Labeled CTO Having an Iso-dC Residue PTO has no label. CTO has a reporter molecule (FAM) and an iso-dC residue at its 5'-end. During extension reaction of PTO fragment, an iso-dGTP labeled with a quencher molecule (dabcyl) is incorporated at the position complementary to the iso-dC residue.

The sequences of upstream primer, downstream primer, PTO and CTO used in this Example are:

```
NG-F
                               (SEQ ID NO: 10)
5'-TACGCCTGCTACTTTCACGCT-3'

NG-R
                               (SEQ ID NO: 2)
5'-CAATGGATCGGTATCACTCGC-3'

NG-PTO-1
                               (SEQ ID NO: 3)
5'-ACGACGGCTTGGCTGCCCCTCATTGGCGTGTTTC

G[C3 spacer]-3'

NG-CTO-5
                               (SEQ ID NO: 11)
5'-[FAM][Iso-dC]CTCCTCCAGTAAAGCCAAGCC

GTCGT[C3 spacer]-3'
(Underlined letters indicate the
5'-tagging portion of PTO)
```

3-2-1. PTOCE Assay Comprising Real-Time Detection at a Pre-Determined Temperature The reaction was conducted in the final volume of 20 µl containing 100 pg of genomic DNA of NG, 10 pmole of downstream primer (SEQ ID NO: 10), 10 pmole of upstream primer (SEQ ID NO: 2), 5 pmole of PTO (SEQ ID NO: 3), 2 pmole of CTO (SEQ ID NO: 11), and 10 µl of 2× Plexor® Master Mix (Cat. No. A4100, Promega, USA); the tube containing the reaction mixture was placed in the real-time thermocycler (CFX96, Bio-Rad); the reaction mixture was denatured for 15 min at 95° C. and subjected to 60 cycles of 30 sec at 95° C., 60 sec at 60° C., 30 sec at 72° C. and 5 cycles of 30 sec at 72° C., 30 sec at 55° C. Detection of the signal was performed at 60° C. of each cycle. The detection temperature was determined to the extent that the extended duplex maintains a double-stranded form.

DNA polymerase having 5' nuclease in the Plexor® Master Mix was used for the extension of upstream primer and downstream primer, the cleavage of PTO and the extension of PTO fragment.

Figure 18A:
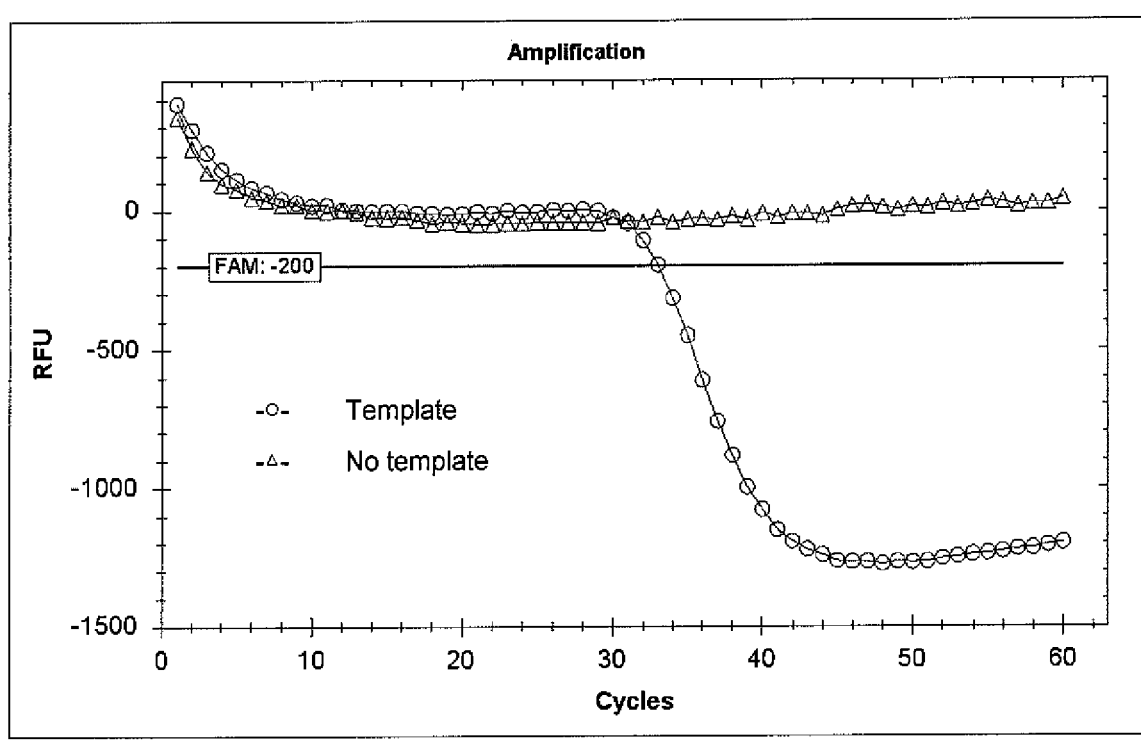
FIG. 18A and FIG. 18B show the results of the detection of *Neisseria gonorrhoeae* gene by PTOCE assay with PCR amplification. CTO has an iso-dC residue and a reporter molecule at its 5'-end. Quencher-iso-dGTP is incorporated into the extended duplex during extension reaction.

As shown in FIG. 18A, the target signal (Ct 33.03) was detected in the presence of the template. No signal was detected in the absence of the template.

3-2-2. PTOCE Assay Comprising Melting Analysis

After the reaction in Example 3-2-1, melting curve was obtained by cooling the reaction mixture to 35° C., holding at for 35° C. for 30 sec, and heating slowly at 35° C. to 90° C. The fluorescence was measured continuously during the temperature rise to monitor dissociation of double-stranded DNAs. Melting peak was derived from the melting curve data.

Figure 18B:
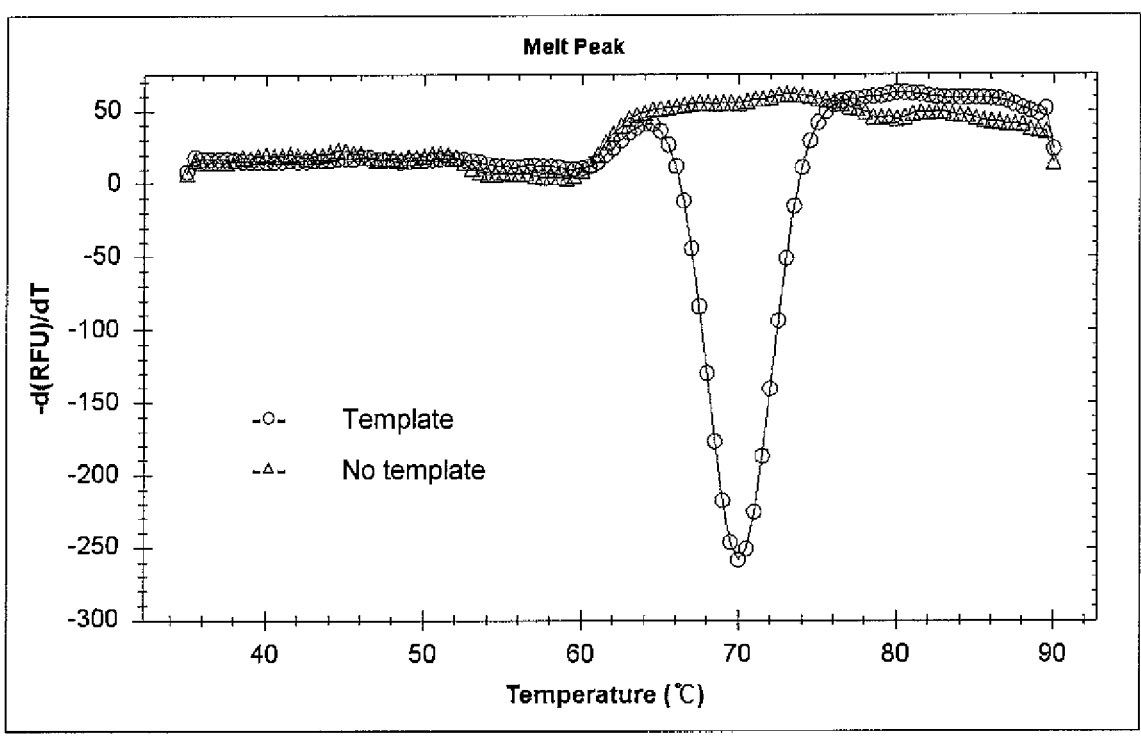

As shown FIG. 18B, a peak at 70.0° C. corresponding to the expected Tm value of the extended duplex was detected in the presence of the template. No peak was detected in the absence of the template. Since the hybrid of uncleaved PTO and CTO does not give any signal in this labeling method, there was no peak corresponding to the hybrid of uncleaved PTO and CTO.

3-3. PTOCE Assay Using a Quencher-Labeled PTO and a Reporter-Labeled CTO

PTO is labeled with a quencher molecule (BHQ-1) at its 5'-end. CTO is labeled with a fluorescent reporter molecule (FAM) at its 3'-end.

The sequences of upstream primer, downstream primer, PTO and CTO used in this Example are:

```
NG-F
                                    (SEQ ID NO: 10)
5'-TACGCCTGCTACTTTCACGCT-3'

NG-R
                                    (SEQ ID NO: 2)
5'-CAATGGATCGGTATCACTCGC-3'

NG-PTO-4
                                    (SEQ ID NO: 12)
5'-[BHQ-1]ACGACGGCTTGCCCCTCATTGGCGTGTTTCG[C3
spacer]-3'

NG-CTO-2
                                    (SEQ ID NO: 6)
5'-CCTCCTCCTCCTCCTCCTCCTCCAGTAAAGCCAAGCCGTC
GT[FAM]-3'
(Underlined letters indicate the 5'-tagging
portion of PTO)
```

3-3-1. PTOCE Assay Comprising Real-Time Detection at a Pre-Determined Temperature The reaction was conducted in the final volume of 20 μl containing 100 pg of NG genomic DNA, 10 pmole of downstream primer (SEQ ID NO: 10), 10 pmole of upstream primer (SEQ ID NO: 2), 5 pmole of PTO (SEQ ID NO: 12), 2 pmole of CTO (SEQ ID NO: 6) and 10 μl of 2× Master Mix containing 2.5 mM MgCl$_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 60 cycles of 30 sec at 95° C., 60 sec at 60° C., 30 sec at 72° C. Detection of the signal was performed at 60° C. of each cycle. The detection temperature was determined to the extent that the extended duplex maintains a double-stranded form and the temperature is higher than the T$_m$ value of a hybrid between uncleaved PTO and CTO.

Figure 19A:
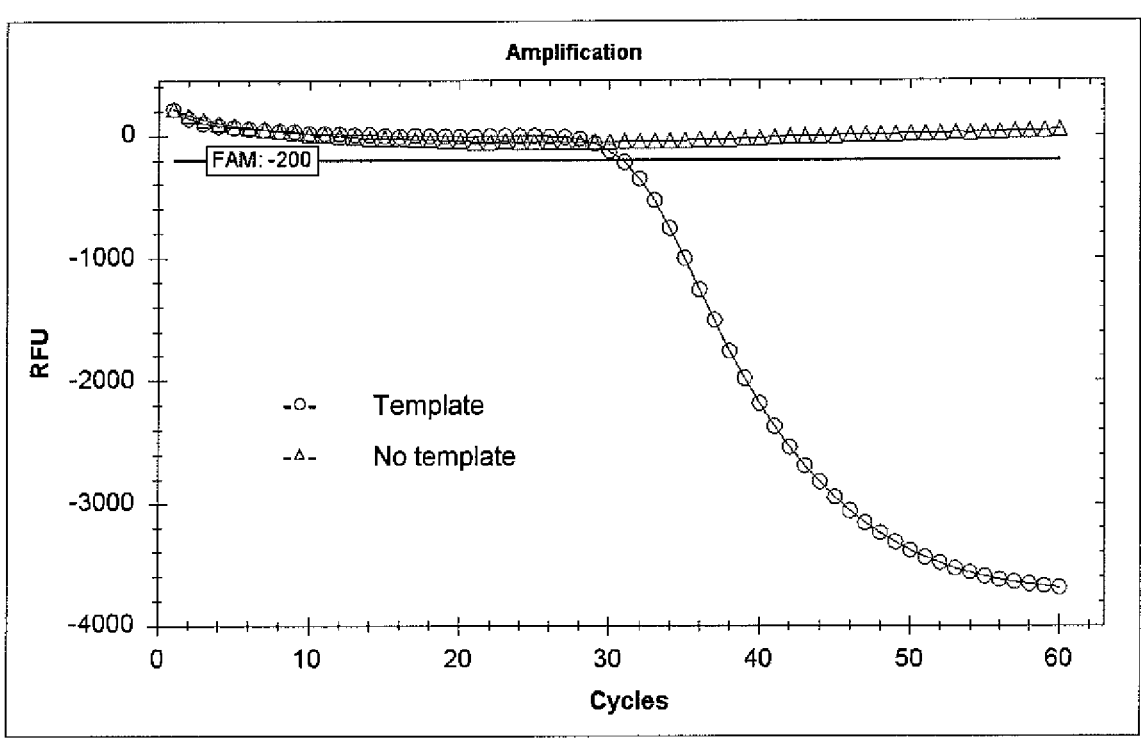

As shown in FIG. 19A, the target signal (Ct 29.79) was detected in the presence of the template. No signal was detected in the absence of the template.

3-3-2. PTOCE Assay Comprising Melting Analysis

After the reaction in Example 3-3-1, melting curve was obtained by cooling the reaction mixture to 35° C., holding at for 35° C. for 30 sec, and heating slowly at 35° C. to 90° C. The fluorescence was measured continuously during the temperature rise to monitor dissociation of double-stranded DNAs. Melting peak was derived from the melting curve data.

As shown FIG. 19B, a peak at 76.5° C. corresponding to the expected Tm value of the extended duplex was detected in the presence of the template. Since the hybrid of uncleaved PTO and CTO does give a non-target signal in this labeling method, the peak corresponding to the Tm value of the hybrid of uncleaved PTO and CTO was detected at 48.0° C. in the absence of the template.

These results indicate that a target nucleic acid sequence can be detected by PTOCE assay comprising real-time detection or melting analysis.

Example 4: Detection of Multiple Target Nucleic Acid Sequences by PTOCE Assay Comprising Melting Analysis We also examined whether the PTOCE assay comprising melting analysis can detect multiple target nucleic acid sequences using the same type of a reporter molecule.

Cleavage of PTOs and extension of PTO fragments were accompanied with the amplification of target nucleic acid sequences by PCR process and the presence of the extended duplexes was detected by post-PCR melting analysis (PTOCE assay comprising melting analysis).

The extended duplexes formed during the assay were designed to have an interactive dual label. The interactive dual label in extended duplex was provided by CTO labeled with a reporter molecule and a quencher molecule in its templating portion. The CTOs have the same type of a fluorescent reporter molecule (FAM) but have different sequences to generate the different Tm values of the extended duplexes. PTO and CTO are blocked with a carbon spacer at their 3'-ends.

Genomic DNAs of *Neisseria gonorrhoeae* (NG) and *Staphylococcus aureus* (SA) were used as target nucleic acids.

The sequences of upstream primer, downstream primer, PTOs and CTOs used in this Example are:

```
NG-F
                                    (SEQ ID NO: 10)
5'-TACGCCTGCTACTTTCACGCT-3'

NG-R
                                    (SEQ ID NO: 2)
5'-CAATGGATCGGTATCACTCGC-3'

NG-PTO-3
                                    (SEQ ID NO: 7)
5'-ACGACGGCTTGGCCCCTCATTGGCGTGTTTCG[C3 spacer]-3'
```

-continued

NG-CTO-1

(SEQ ID NO: 4)

5'-[BHQ-1]CCTCCTCCTCCTCCTCCTCC[T(FAM)]]

CCAGTAAAGCCAAGCCGTCGT[C3 Spacer]-3'

SA-F (SEQ ID NO: 13)

5'-TGTTAGAATTTGAACAAGGATTTAATC-3'

SA-R (SEQ ID NO: 14)

5'-GATAAGTTTAAAGCTTGACCGTCTG-3'

SA-PTO-1

(SEQ ID NO: 15)

5'-AATCCGACCACGCATTCCGTGGTCAATCATTCGGTTTAC

G[C3 spacer]-3'

SA-CTO-1

(SEQ ID NO: 16)

5'-[BHQ-1]TTTTTTTTTTTTTTTTTGCA[T(FAM)]AGCGTGGTCG

GATT[C3 spacer]-3'

(Underlined letters indicate the 5'-tagging portion of PTO)

The reaction was conducted in the final volume of 20 μl containing 100 pg of genomic DNA of NG, 100 pg of genomic DNA of SA, 10 pmole of each downstream primer (SEQ ID NOs: 10 and 13), 10 pmole of each upstream primer (SEQ ID NOs: 2 and 14), 5 pmole of each PTO (SEQ ID NOs: 7 and 15), 2 pmole of each CTO (SEQ ID NOs: 4 and 16), and 10 μl of 2× Master Mix containing 2.5 mM $MgCl_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 60 cycles of 30 sec at 95° C., 60 sec at 60° C., 30 sec at 72° C. After the reaction, melting curve was obtained by cooling the reaction mixture to 35° C., holding at for 35° C. for 30 sec, and heating slowly at 35° C. to 90° C. The fluorescence was measured continuously during the temperature rise to monitor dissociation of double-stranded DNAs. Melting peak was derived from the melting curve data.

As shown in FIG. 20, multiple target signals (NG's Tm: 75.5° C. and SA's Tm: 63.5° C.) were detected in the presence of the templates. No signal was detected in the absence of the templates.

These results indicate that PTOCE assay comprising melting analysis allows us to detect multiple target nucleic acids by using the same type of a reporter molecule (e.g. FAM) in the condition that the extended duplexes corresponding to the target nucleic acids have different $T_m$ values.

Example 5: Evaluation of PTOCE Assay Comprising Melting Analysis on Microarray We further examined PTOCE assay comprising melting analysis on microarray. PTO cleavage was conducted in a separate vessel and an aliquot of the resultant was taken into a microarray where CTO was immobilized. After the extension reaction, the presence of the extended duplex was detected by melting analysis.

Taq DNA polymerase having 5' nuclease activity was used for the extension of upstream primer, the cleavage of PTO and the extension of PTO fragment. The extended duplex formed during the assay was designed to have a single label. The single label in the extended duplex was provided by PTO labeled with Quasar570 as a fluorescent reporter molecule at its 5'-end. PTO and CTO are blocked with a carbon spacer at their 3'-ends. The CTO has poly(T)$_5$ as a linker arm and was immobilized on the surface of a glass slide by using an amino group (AminnoC7) at its 5'-end. A marker probe having a fluorescent reporter molecule (Quasar570) at its 5'-end was immobilized on the surface of the glass slide by using an amino group at its 3'-end.

The sequences of synthetic template, upstream primer, PTO, CTO and marker used in this Example are:

NG-T (SEQ ID NO: 1)

5'-AAATATGCGAAACACGCCAATGAGGGGCATGATGCTTTCTTTTTGTT

CTTGCTCGGCAGAGCGAGTGATACCGATCCATTGAAAAA-3'

NG-R (SEQ ID NO: 2)

5'-CAATGGATCGGTATCACTCGC-3'

NG-PTO-5

(SEQ ID NO: 17)

5'-[Quasar570]ACGACGGCTTGGCTTTACTGCCCCTCATTGGCGTGT

TTCG[C3 spacer]-3'

NG-CTO-S1

(SEQ ID NO: 18)

5'-[AminoC7TTTTTCCTCCTCCTCCTCCTCCTCCTCCAGTAAAGCCAA

GCCGTCGT [C3 Spacer]-3'

Marker (SEQ ID NO: 19)

5'-[Quasar570]ATATATATAT[AminoC7]-3'

(Underlined letters indicate the 5'-tagging portion of PTO)

NSB9 NHS slides (NSBPOSTECH, Korea) were used for fabrication of the CTO and marker (SEQ ID NOs: 18 and 19). The CTO and marker dissolved in NSB spotting buffer at the final concentration of 10 μM were printed on the NSB9 NHS slides with PersonalArrayer™ 16 Microarray Spotter (CapitalBio, China). The CTO and marker were spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound CTO and marker and rinsed with distilled water. Then, the DNA-functionalized slides were dried using a slide centrifuge and stored in dark at 4° C. until use.

The cleavage reaction was conducted in the final volume of 50 μl containing 2 pmole of synthetic template (SEQ ID NO: 1) for NG gene, 10 pmole of upstream primer (SEQ ID NO: 2), 1 pmole of PTO (SEQ ID NO: 17), and 25 μl of 2× Master Mix containing 2.5 mM $MgCl_2$, 200 μM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 63° C.

The 30 μl of the resulting mixture was applied to a chamber assembled on the surface of NSB glass slide on which the CTO (SEQ ID NO: 18) was cross-linked. The slide was placed on in situ block in a thermocycler (GenePro B4I, China). Six same slides were prepared for melting analysis. The extension reaction was allowed for 20 min at 55° C. Then, the resulting slides were incubated for 1 min at room temperature. Finally each slide was washed in distilled water for 1 min at 44° C., 52° C., 60°, 68°, 76° or 84°. The image acquisition was carried out by the use of Confocal Laser Scanner, Axon GenePix4100A (Molecular Device, US) with scanning at 5 μm pixel resolution. The fluorescence intensity was analyzed by the use of quantitative microarray analysis software, GenePix pro6.0 software (Molecular Device, US). The fluorescence intensity was expressed as spot-medians after local background subtractions. Each spot was duplicated for the test of reproducibility. The fluorescence intensity indicates the average value of the duplicated spots.

Figure 21A:
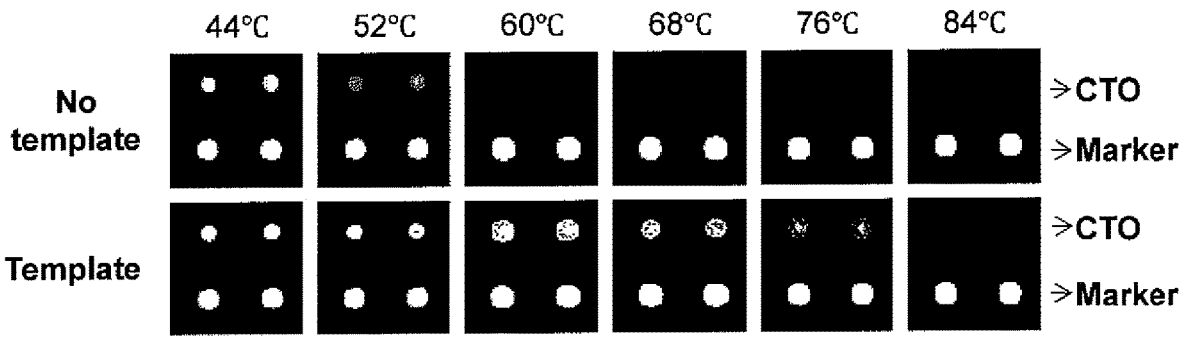

As shown in FIGS. 21A and 21B, melting curve was obtained by measuring the fluorescent intensity from the spots prepared by different washing temperatures. The presence of the extended duplex was determined from the melting curve data.

Example 6: Evaluation of PTOCE Assay Comprising Real-Time Detection on Microarray We further examined PTOCE assay comprising real-time detection at a pre-determined temperature on microarray.

Cleavage of PTO and extension of PTO fragment were repeated on a microarray where CTO was immobilized. The presence of the extended duplex was detected at a pre-determined temperature in several determined cycles.

Taq DNA polymerase having 5' nuclease activity was used for the extension of upstream primer, the cleavage of PTO and the extension of PTO fragment.

The extended duplex formed during the assay was designed to have a single label or an interactive dual label. The single label in the extended duplex was provided by PTO labeled with a reporter molecule (reporter-labeled PTO). The interactive dual label in the extended duplex was provided by CTO labeled with a reporter molecule and a quencher molecule (dual-labeled CTO). PTO and CTO are blocked with a carbon spacer at their 3'-ends.

The CTO has poly(T) as a linker arm. The CTO was immobilized on a glass slide by using an amino group (AminnoC7) at its 5'-end or its 3'-end. A marker probe having a fluorescent reporter molecule (Quasar570) at its 5'-end was immobilized on the glass slide by using an amino group at its 3'-end. A fluorescent intensity on the glass slide was measured at a pre-determined temperature. The detection temperature was determined to the extent that the extended duplex maintains a double-stranded form. Synthetic oligonucleotide for *Neisseria gonorrhoeae* (NG) was used as templates.

6-1. PTOCE Assay Using a Reporter-Labeled PTO

PTO has Quasar570 as a fluorescent reporter molecule at its 5'-end. The CTO was immobilized through its 5'-end. In this labeling method, the detection temperature was determined to the extent that the extended duplex maintains a double-stranded form and the temperature is higher than the $T_m$ value of a hybrid between uncleaved PTO and CTO.

The sequences of synthetic template, upstream primer, PTO, CTO and marker used in this Example are:

```
NG-T
                                    (SEQ ID NO: 1)
5'-AAATATGCGAAACACGCCAATGAGGGGCATGATGCTTTCTTTTTGTT

CTTGCTCGGCAGAGCGAGTGATACCGATCCATTGAAAAA-3'
```

-continued
```
NG-R
                                    (SEQ ID NO: 2)
5'-CAATGGATCGGTATCACTCGC-3'

NG-PTO-5
                                    (SEQ ID NO: 17)
5'-[Quasar570]ACGACGGCTTGGCTTTACTGCCCCTCATTGGCGTGT TTCG[C3 spacer]-3'

NG-CTO-S1
                                    (SEQ ID NO: 18)
5'-[AminoC7]TTTTTCCTCCTCCTCCTCCTCCTCCTCCAGTAAAGCCA AGCCGTCGT[C3 Spacer]-3'

Marker
                                    (SEQ ID NO: 19)
5'-[Quasar570]ATATATATAT[AminoC7]-3'
(Underlined letters indicate the 5'-tagging
portion of PTO)
```

Slide preparation was conducted as the same protocol used in Example 5.

The PTOCE reaction was conducted in the final volume of 30 μl containing 2 pmole of synthetic template (SEQ ID NO: 1) for NG gene, 10 pmole of upstream primer (SEQ ID NO: 2), 1 pmole of PTO (SEQ ID NO: 17), and 15 μl of 2× Master Mix containing 2.5 mM MgCl₂, 200 μM of dNTPs, and 2.4 units of H-Taq DNA polymerase (Solgent, Korea); the whole mixture was applied to a chamber assembled on the surface of NSB glass slide on which the CTO (SEQ ID NO: 18) was cross-linked. The slide was placed on in situ block in a thermocycler (GenePro B4I, China). Five same slides were prepared for cycling analysis. The PTOCE reaction was carried out as follows: 15 min denaturation at 95° and 0, 5, 10, 20 or 30 cycles of 30 sec at 95°, 60 sec at 60°, 60 sec at 55°. After the reaction of the corresponding cycle number, the slides were washed in distilled water at 64° for 1 min. The image acquisition was carried out after each washing by the use of Confocal Laser Scanner, Axon GenePix4100A (Molecular Device, US) with scanning at 5-μm pixel resolution. The fluorescence intensity was analyzed by the use of quantitative microarray analysis software, GenePix pro6.0 software (Molecular Device, US). The fluorescence intensity was expressed as spot-medians after local background subtractions. Each spot was duplicated for the test of reproducibility. The fluorescence intensity indicates the average value of the duplicated spots.

Figure 22A:
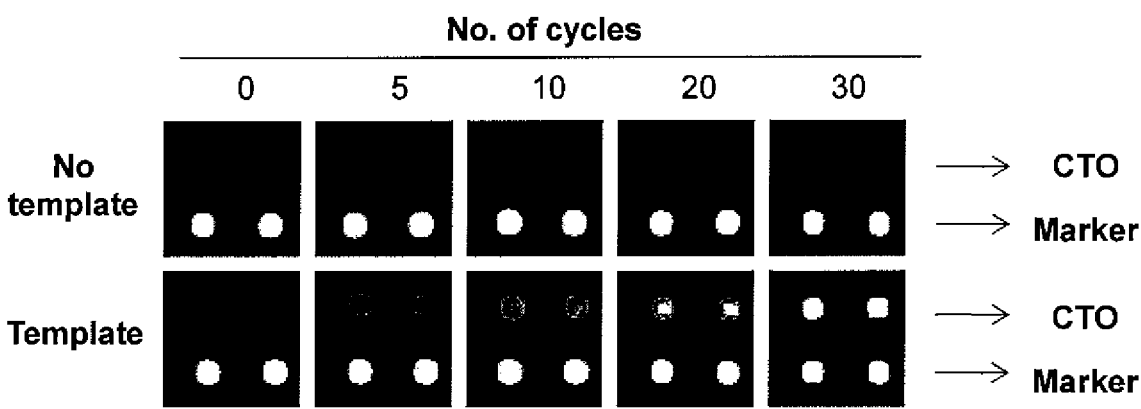

As shown in FIGS. 22A and 22B, the fluorescent intensity for the target nucleic acid sequence was increased depending on cycle numbers (0 cycle_RFU: 1,304±0.7; 5 cycles_RFU: 18,939±1,342.1; 10 cycles_RFU: 30,619±285.0; 20 cycles_RFU: 56,248±2,208.3; and 30 cycles_RFU: 64,645±1,110.2) in the presence of the template. There was no change of the fluorescent intensity depending on cycle numbers in the absence of the template.

6-2. PTOCE Assay Using a Dual-Labeled CTO

The CTO was immobilized through its 3'-end and has a quencher molecule (BHQ-2) and a fluorescent reporter molecule (Quasar570) in its templating portion.

The sequences of synthetic template, upstream primer, PTO, CTO and marker used in this Example are:

```
NG-T
                                    (SEQ ID NO: 1)
5'-AAATATGCGAAACACGCCAATGAGGGGCATGATGCTTTCTTT

TTGTTCTTGCTCGGCAGAGCGAGTGATACCGATCCATTGAAAAA-

3'

NG-R
                                    (SEQ ID NO: 2)
5'-CAATGGATCGGTATCACTCGC-3'

NG-PTO-6
                                    (SEQ ID NO: 20)
5'-ACGACGGCTTGGCTTTACTGCCCCTCATTGGCGTGTTT

CG [C3 spacer]-3'

NG-CTO-52
                                    (SEQ ID NO: 21)
5'-[BHQ-2]CCTCCTCCTCCTCCTCCTCC[T(Quasar570)]

CCAGTAAAGCCAAGCCGTCGTTTTTTTTTTT[AminoC7]-3'

Marker
                                    (SEQ ID NO: 19)
5'-[Quasar570]ATATATATAT[AminoC7]-3'
(Underlined letters indicate the 5'-tagging
portion of PTO)
```

Slide preparation was conducted as the same protocol used in Example 5.

The PTOCE reaction was conducted in the final volume of 30 µl containing 2 pmole of synthetic template (SEQ ID NO: 1) for NG gene, 10 pmole of upstream primer (SEQ ID NO: 2), 1 pmole of PTO (SEQ ID NO: 20), and 15 µl of 2× Master Mix containing 2.5 mM $MgCl_2$, 200 µM of dNTPs, and 2.4 units of H-Taq DNA polymerase (Solgent, Korea); the whole mixture was applied to a chamber assembled on the surface of NSB glass slide on which the CTO was cross-linked (SEQ ID NO: 21). The slide was placed on in situ block in a thermocycler (GenePro B4I, China). Five same slides were prepared for cycling analysis. The PTOCE reaction was carried out as follows: 15 min denaturation at 95° C. and 0, 5, 10, 20 or 30 cycles of 30 sec at 95° C., 60 sec at 60° C., 60 sec at 50° C. After the reaction of the corresponding cycle number, the image acquisition was carried out by the use of Confocal Laser Scanner, Axon GenePix4100A (Molecular Device, US) with scanning at 5 µm pixel resolution. The fluorescence intensity was analyzed by the use of quantitative microarray analysis software, GenePix pro6.0 software (Molecular Device, US). The fluorescence intensity was expressed as spot-medians after local background subtractions. Each spot was duplicated for the test of reproducibility. The fluorescence intensity indicates the average value of the duplicated spots.

Figure 23A:
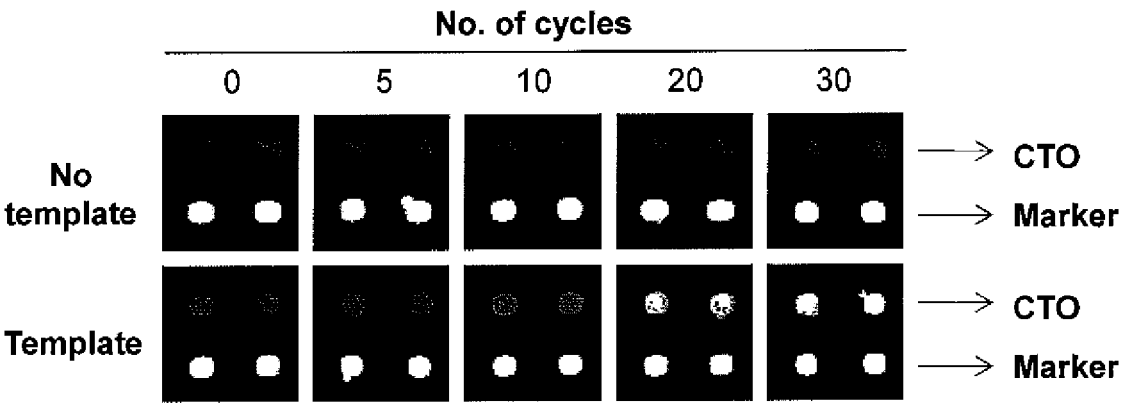

As shown in FIGS. 23A and 23B, the fluorescent intensity for the target nucleic acid sequence was increased depending on cycle numbers (0 cycle_RFU: 28,078±460.3; 5 cycles_RFU: 35,967±555.1; 10 cycles_RFU: 44,674±186.0; 20 cycles_RFU: 65,423±2.1; and 30 cycles_RFU: 65,426±2.8) in the presence of template. There was no change of the fluorescent intensity depending on cycle numbers in the absence of the template.

Example 7: Detection of Multiple Target Nucleic Acid Sequences by PTOCE Assay Comprising End-Point Detection at a Pre-Determined Temperature on Microarray We further examined multiple target detection by PTOCE assay comprising end-point detection at a pre-determined temperature on microarray.

PTO cleavage was conducted in a separate vessel with PCR process and an aliquot of the resultant was taken into a microarray where CTO was immobilized. After extension reaction, the presence of the extended duplex was detected by end-point detection at a pre-determined temperature.

Taq DNA polymerase having 5' nuclease activity was used for the extension of upstream primer and downstream primer, the cleavage of PTO and the extension of PTO fragment.

The extended duplex formed during the assay was designed to have a single label. The single label in the extended duplex was provided by PTO labeled with Quasar570 as a fluorescent reporter molecule at the 5'-end of the PTO. PTO and CTO are blocked with a carbon spacer at their 3'-ends.

The CTO has poly(T)$_5$ as a linker arm and was immobilized on a glass slide by using an amino group (AminnoC7) at its 5'-end. A marker probe having a fluorescent reporter molecule (Quasar570) at its 5'-end was immobilized on the glass slide by using an amino group at its 3'-end.

A fluorescent intensity on the glass slide was measured at a pre-determined temperature. The detection temperature was determined to the extent that the extended duplex maintains a double-stranded form and the temperature is higher than the $T_m$ value of a hybrid between uncleaved PTO and CTO. Genomic DNAs of *Staphylococcus aureus* (SA) and *Neisseria gonorrhoeae* (NG) were used.

The sequences of upstream primer, downstream primer, PTO, CTO and marker used in this Example are:

```
NG-F
                                    (SEQ ID NO: 10)
5'-TACGCCTGCTACTTTCACGCT-3'

NG-R
                                    (SEQ ID NO: 2)
5'-CAATGGATCGGTATCACTCGC-3'

NG-PTO-5
                                    (SEQ ID NO: 17)
5'-[Quasar570]ACGACGGCTTGGCTTTACTGCCCCTCATTGGCGTGT TTCG[C3 spacer]-3'

NG-CTO-S1
                                    (SEQ ID NO: 18)
5'-[AminoC7]TTTTTCCTCCTCCTCCTCCTCCTCCTCCAGTAAAGCCA AGCCGTCGT[C3 Spacer]-3'

SA-F
                                    (SEQ ID NO: 13)
5'-TGTTAGAATTTGAACAAGGATTTAATC-3'

SA-R2
                                    (SEQ ID NO: 22)
5'-TTAGCTCCTGCTCCTAAACCA-3'

SA-PTO-2
                                    (SEQ ID NO: 23)
5'-[Quasar570]AATCCGACCACGCTATGCTCATTCCGTGGTCAATCA TTCGGTTTACG[C3 spacer]-3'
```

-continued

SA_CTO-S1

(SEQ ID NO: 24)

5'-[AminoC7]TTTTTCTTCTTCTTCTTCTTCTTCTTCTTCCCCCAGCA

TAGCGTGGTCGGATT [C3 Spacer]-3'

Marker (SEQ ID NO: 19)

5'-[Quasar570]ATATATATAT[AminoC7]-3'
(Underlined letters indicate the 5'-tagging
portion of PTO)

Slide preparation was conducted as the same protocol used in Example 5.

The cleavage reaction was conducted in the final volume of 50 µl containing each 100 pg genomic DNA of SA and/or NG, each 10 pmole of downstream primer (SEQ ID NOs: 10 and/or 13), each 10 pmole of upstream primer (SEQ ID NOs: 2 and/or 22), each 1 pmole of PTO (SEQ ID NOs: 17 and/or 23), and 25 µl of 2× Master Mix containing 2.5 mM MgCl$_2$, 200 µM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° and subjected to 60 cycles of 30 sec at 95°, 60 sec at 63°. The 30 µl of the resulting mixture was applied to a chamber assembled on the surface of NSB glass slide on which the CTOs (SEQ ID NOs: 18 and 24) were cross-linked. The slide was placed on in situ block in a thermocycler (GenePro B4I, China). The extension reaction was allowed for 20 min at 55°. Then the slides were washed in distilled water at 64° C. for 1 min. The image acquisition was carried out after each washing by the use of Confocal Laser Scanner, Axon GenePix4100A (Molecular Device, US) with scanning at 10 µm pixel resolution. The fluorescence intensity was analyzed by the use of quantitative microarray analysis software, GenePix pro6.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 24, the target signal for SA (RFU: 65,192±198.7) was detected in the presence of SA template. The target signal for NG (RFU: 65,332±1.4) was detected in the presence of NG template. Both target signals for SA (RFU: 65,302±0.7) and NG (RFU 65,302±0.7) were detected in the presence of both templates.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A kit for detecting a target nucleic acid sequence from a DNA or a mixture of nucleic acids, comprising:

(a) a PTO (Probing and Tagging Oligonucleotide) comprising (i) a 3'-targeting portion comprising a hybridizing nucleotide sequence complementary to a target nucleic acid sequence, and (ii) the 5'-tagging portion comprising a nucleotide sequence non-complementary to the target nucleic acid sequence;

(b) a CTO (Capturing and Templating Oligonucleotide) comprising in a 3' to 5' direction (i) a capturing portion comprising a nucleotide sequence complementary to a 5'-tagging portion or a part of the 5'-tagging portion of the PTO, and (ii) a templating portion comprising a nucleotide sequence non-complementary to the 5'-tagging portion and the 3'-targeting portion of the PTO; said 5'-tagging portion having a 5' end; and (c) an enzyme having a 5' nuclease activity;

wherein the CTO does not have a hairpin structure and has an interactive dual label comprising a reporter molecule and a quencher molecule;

wherein one of the reporter molecule and the quencher molecule on the CTO is located at the 5'-end and the other is located at least 10 nucleotides apart from the 5'-end;

and wherein the kit does not contain any additional oligonucleotides that are immobilized on a solid substrate.

2. The kit of claim 1, wherein the capturing portion of the CTO is 5-60 nucleotides in length.

3. The kit of claim 1, wherein the templating portion of the CTO is 2-300 nucleotides in length.

4. The kit of claim 1, wherein the quencher molecule is a non-fluorescent black quencher molecule.

*    *    *    *    *

SEQUENCE LISTING

```
<160> NUMBER OF SEQ ID NOS: 24

<210> SEQ ID NO 1
<211> LENGTH: 86
<212> TYPE: DNA
<213> ORGANISM: Artificial Sequence
<220> FEATURE:
<223> OTHER INFORMATION: Synthetic construct; NG-T

<400> SEQUENCE: 1
aaatatgcga aacacgccaa tgaggggcat gatgctttct ttttgttctt gctcggcaga      60
gcgagtgata ccgatccatt gaaaaa      86

<210> SEQ ID NO 2
<211> LENGTH: 21
<212> TYPE: DNA
<213> ORGANISM: Artificial Sequence
<220> FEATURE:
<223> OTHER INFORMATION: Synthetic construct; NG-R

<400> SEQUENCE: 2
caatggatcg gtatcactcg c      21

<210> SEQ ID NO 3
<211> LENGTH: 35
<212> TYPE: DNA
<213> ORGANISM: Artificial Sequence
<220> FEATURE:
<223> OTHER INFORMATION: Synthetic construct; NG-PTO-1

<400> SEQUENCE: 3
acgacggctt ggctgccct cattggcgtg tttcg      35

<210> SEQ ID NO 4
<211> LENGTH: 42
<212> TYPE: DNA
```

-continued

```
<213> ORGANISM: Artificial Sequence
<220> FEATURE:
<223> OTHER INFORMATION: Synthetic construct; NG-CTO-1

<400> SEQUENCE: 4
cctcctcctc ctcctcctcc tccagtaaag ccaagccgtc gt                        42

<210> SEQ ID NO 5
<211> LENGTH: 40
<212> TYPE: DNA
<213> ORGANISM: Artificial Sequence
<220> FEATURE:
<223> OTHER INFORMATION: Synthetic construct; NG-PTO-2

<400> SEQUENCE: 5
acgacggctt ggctttactg cccctcattg gcgtgtttcg                           40

<210> SEQ ID NO 6
<211> LENGTH: 42
<212> TYPE: DNA
<213> ORGANISM: Artificial Sequence
<220> FEATURE:
<223> OTHER INFORMATION: Synthetic construct; NG-CTO-2

<400> SEQUENCE: 6
cctcctcctc ctcctcctcc tccagtaaag ccaagccgtc gt                        42

<210> SEQ ID NO 7
<211> LENGTH: 32
<212> TYPE: DNA
<213> ORGANISM: Artificial Sequence
<220> FEATURE:
<223> OTHER INFORMATION: Synthetic construct; NG-PTO-3

<400> SEQUENCE: 7
acgacggctt ggcccctcat tggcgtgttt cg                                   32

<210> SEQ ID NO 8
<211> LENGTH: 37
<212> TYPE: DNA
<213> ORGANISM: Artificial Sequence
<220> FEATURE:
<223> OTHER INFORMATION: Synthetic construct; NG-CTO-3

<400> SEQUENCE: 8
tttttttttt cctcctccag taaagccaag ccgtcgt                             37

<210> SEQ ID NO 9
<211> LENGTH: 37
<212> TYPE: DNA
<213> ORGANISM: Artificial Sequence
<220> FEATURE:
<223> OTHER INFORMATION: Synthetic construct; NG-CTO-4

<400> SEQUENCE: 9
tttttttttt ttttttttag taaagccaag ccgtcgt                             37

<210> SEQ ID NO 10
<211> LENGTH: 21
<212> TYPE: DNA
<213> ORGANISM: Artificial Sequence
<220> FEATURE:
<223> OTHER INFORMATION: Synthetic construct; NG-F

<400> SEQUENCE: 10
tacgcctgct actttcacgc t                                               21
```

```
<210> SEQ ID NO 11
<211> LENGTH: 27
<212> TYPE: DNA
<213> ORGANISM: Artificial Sequence
<220> FEATURE:
<223> OTHER INFORMATION: Synthetic construct; NG-CTO-5

<400> SEQUENCE: 11
cctcctccag taaagccaag ccgtcgt                                          27

<210> SEQ ID NO 12
<211> LENGTH: 31
<212> TYPE: DNA
<213> ORGANISM: Artificial Sequence
<220> FEATURE:
<223> OTHER INFORMATION: Synthetic construct; NG-PTO-4

<400> SEQUENCE: 12
acgacggctt gcccctcatt ggcgtgtttc g                                     31

<210> SEQ ID NO 13
<211> LENGTH: 27
<212> TYPE: DNA
<213> ORGANISM: Artificial Sequence
<220> FEATURE:
<223> OTHER INFORMATION: Synthetic construct; SA-F

<400> SEQUENCE: 13
tgttagaatt tgaacaagga tttaatc                                          27

<210> SEQ ID NO 14
<211> LENGTH: 25
<212> TYPE: DNA
<213> ORGANISM: Artificial Sequence
<220> FEATURE:
<223> OTHER INFORMATION: Synthetic construct; SA-R

<400> SEQUENCE: 14
gataagttta aagcttgacc gtctg                                            25

<210> SEQ ID NO 15
<211> LENGTH: 40
<212> TYPE: DNA
<213> ORGANISM: Artificial Sequence
<220> FEATURE:
<223> OTHER INFORMATION: Synthetic construct; SA-PTO-1

<400> SEQUENCE: 15
aatccgacca cgcattccgt ggtcaatcat tcggtttacg                            40

<210> SEQ ID NO 16
<211> LENGTH: 35
<212> TYPE: DNA
<213> ORGANISM: Artificial Sequence
<220> FEATURE:
<223> OTHER INFORMATION: Synthetic construct; SA-CTO-1

<400> SEQUENCE: 16
tttttttttt tttttttgca tagcgtggtc ggatt                                 35

<210> SEQ ID NO 17
<211> LENGTH: 40
<212> TYPE: DNA
<213> ORGANISM: Artificial Sequence
<220> FEATURE:
```

<223> OTHER INFORMATION: Synthetic construct; NG-PTO-5

<400> SEQUENCE: 17
acgacggctt ggctttactg cccctcattg gcgtgtttcg                              40

<210> SEQ ID NO 18
<211> LENGTH: 47
<212> TYPE: DNA
<213> ORGANISM: Artificial Sequence
<220> FEATURE:
<223> OTHER INFORMATION: Synthetic construct; NG-CTO-S1

<400> SEQUENCE: 18
tttttcctcc tcctcctcct cctcctccag taaagccaag ccgtcgt                     47

<210> SEQ ID NO 19
<211> LENGTH: 10
<212> TYPE: DNA
<213> ORGANISM: Artificial Sequence
<220> FEATURE:
<223> OTHER INFORMATION: Synthetic construct; Marker

<400> SEQUENCE: 19
atatatatat                                                              10

<210> SEQ ID NO 20
<211> LENGTH: 40
<212> TYPE: DNA
<213> ORGANISM: Artificial Sequence
<220> FEATURE:
<223> OTHER INFORMATION: Synthetic construct; NG-PTO-6

<400> SEQUENCE: 20
acgacggctt ggctttactg cccctcattg gcgtgtttcg                              40

<210> SEQ ID NO 21
<211> LENGTH: 52
<212> TYPE: DNA
<213> ORGANISM: Artificial Sequence
<220> FEATURE:
<223> OTHER INFORMATION: Synthetic construct; NG-CTO-S2

<400> SEQUENCE: 21
cctcctcctc ctcctcctcc tccagtaaag ccaagccgtc gttttttttt tt               52

<210> SEQ ID NO 22
<211> LENGTH: 21
<212> TYPE: DNA
<213> ORGANISM: Artificial Sequence
<220> FEATURE:
<223> OTHER INFORMATION: Synthetic construct; SA-R2

<400> SEQUENCE: 22
ttagctcctg ctcctaaacc a                                                 21

<210> SEQ ID NO 23
<211> LENGTH: 47
<212> TYPE: DNA
<213> ORGANISM: Artificial Sequence
<220> FEATURE:
<223> OTHER INFORMATION: Synthetic construct; SA-PTO-2

<400> SEQUENCE: 23
aatccgacca cgctatgctc attccgtggt caatcattcg gtttacg                     47

-continued

```
<210> SEQ ID NO 24
<211> LENGTH: 53
<212> TYPE: DNA
<213> ORGANISM: Artificial Sequence
<220> FEATURE:
<223> OTHER INFORMATION: Synthetic construct; SA_CTO-S1

<400> SEQUENCE: 24
tttttcttct tcttcttctt cttcttcttc ccccagcata gcgtggtcgg att          53
```